US009938542B2

(12) United States Patent
Tracy et al.

(10) Patent No.: US 9,938,542 B2
(45) Date of Patent: Apr. 10, 2018

(54) MIXOTROPHIC FERMENTATION METHOD FOR MAKING ACETONE, ISOPROPANOL, BUTYRIC ACID AND OTHER BIOPRODUCTS, AND MIXTURES THEREOF

(71) Applicant: White Dog Labs, Inc., New Castle, DE (US)

(72) Inventors: Bryan P. Tracy, Wilmington, DE (US); Shawn William Jones, Bear, DE (US); Aharon M. Eyal, Jerusalem (IL)

(73) Assignee: WHITE DOG LABS, INC., New Castle, DE (US)

( * ) Notice: Subject to any disclaimer, the term of this patent is extended or adjusted under 35 U.S.C. 154(b) by 0 days.

(21) Appl. No.: 15/055,045

(22) Filed: Feb. 26, 2016

(65) Prior Publication Data
US 2016/0251683 A1 Sep. 1, 2016

Related U.S. Application Data

(60) Provisional application No. 62/265,239, filed on Dec. 9, 2015, provisional application No. 62/209,133, filed on Aug. 24, 2015, provisional application No. 62/199,548, filed on Jul. 31, 2015, provisional application No. 62/183,034, filed on Jun. 22, 2015, provisional application No. 62/121,871, filed on Feb. 27, 2015.

(51) Int. Cl.
C12P 7/56 (2006.01)
C12P 7/54 (2006.01)
C12P 7/52 (2006.01)
C12P 7/26 (2006.01)
C12P 7/28 (2006.01)
C12P 7/16 (2006.01)
C12P 7/06 (2006.01)
C12N 1/20 (2006.01)
C12P 7/04 (2006.01)
C12P 7/24 (2006.01)
C12P 7/18 (2006.01)
C12P 7/40 (2006.01)

(52) U.S. Cl.
CPC .... C12P 7/28 (2013.01); C12P 7/04 (2013.01); C12P 7/06 (2013.01); C12P 7/065 (2013.01); C12P 7/16 (2013.01); C12P 7/18 (2013.01); C12P 7/24 (2013.01); C12P 7/40 (2013.01); C12P 7/54 (2013.01); C12P 7/56 (2013.01); Y02E 50/10 (2013.01); Y02E 50/17 (2013.01)

(58) Field of Classification Search
CPC ...... C12P 7/04; C12P 7/06; C12P 7/16; C12P 7/24; C12P 7/28; C12P 7/56; C12P 7/065; C12P 7/18; C12P 7/40; C12P 7/54; Y02E 50/17; Y02E 50/10
USPC ....... 435/139, 140, 141, 148, 150, 160, 161, 435/252.3, 252.7
See application file for complete search history.

(56) References Cited

U.S. PATENT DOCUMENTS

| 5,173,429 | A | * | 12/1992 | Gaddy | .................. C12P 7/10 435/135 |
|---|---|---|---|---|---|
| 7,749,494 | B2 | | 7/2010 | Renaud et al. | |
| 7,803,589 | B2 | | 9/2010 | Burk et al. | |
| 7,858,350 | B2 | | 12/2010 | Burk et al. | |
| 8,048,661 | B2 | | 11/2011 | Burgard et al. | |
| 8,129,155 | B2 | | 3/2012 | Trawick et al. | |
| 8,129,156 | B2 | | 3/2012 | Burk et al. | |
| 8,129,169 | B2 | | 3/2012 | Van Dien et al. | |
| 8,178,327 | B2 | | 5/2012 | Burk et al. | |
| 8,268,607 | B2 | | 9/2012 | Burgard et al. | |
| 8,293,509 | B2 | | 10/2012 | Simpson et al. | |
| 8,309,323 | B2 | | 11/2012 | Martin et al. | |
| 8,323,950 | B2 | | 12/2012 | Burk et al. | |
| 8,377,666 | B2 | | 2/2013 | Haselbeck et al. | |
| 8,377,667 | B2 | | 2/2013 | Haselbeck et al. | |

(Continued)

FOREIGN PATENT DOCUMENTS

| WO | 2006/108532 | 10/2006 |
|---|---|---|
| WO | 2009/103026 | 8/2009 |

(Continued)

OTHER PUBLICATIONS

Blair et al., Carbon isoptopic fractionation in heterotrophic microbial metabolism. Appl. Environ. Microbiol., 1985, vol. 50(4): 996-1001.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*

(Continued)

Primary Examiner — Ganapathirama Raghu
(74) Attorney, Agent, or Firm — Greenblum & Bernstein, P.L.C.

(57) ABSTRACT

Mixotrophic fermentation method performed to make one or more bioproducts such as alcohols, organic acids of less than 7 carbons, acetone, 2,3-butanediol and mixtures thereof with a microorganism. The mixotrophic fermentation method includes providing an isolated organism and providing a first feedstock and a second feedstock for use in a fermentation medium. The first feedstock includes a carbon source that is metabolized by the native form of the organism at a rate of less than 0.01 g/hr/g cell mass, and the second feedstock includes CO, $CO_2$, carbonate, bicarbonate, $H_2$, glycerol, methanol, formate, urea or mixtures thereof. The mixotrophic fermentation method also includes culturing the organism in the fermentation medium, whereby both feedstocks are metabolized and a fermentation broth is formed, the broth having at least one bioproduct. Optionally, the bioproduct may be separated from the broth.

24 Claims, 5 Drawing Sheets

(56) References Cited

U.S. PATENT DOCUMENTS

| | | | |
|---|---|---|---|
| 8,426,173 B2 | 4/2013 | Bramucci et al. | |
| 8,426,174 B2 | 4/2013 | Bramucci et al. | |
| 8,445,244 B2 | 5/2013 | Burgard et al. | |
| 8,580,543 B2 | 11/2013 | Burk et al. | |
| 8,637,286 B2 | 1/2014 | Burgard et al. | |
| 8,691,553 B2 | 4/2014 | Burk et al. | |
| 8,697,421 B2 | 4/2014 | Burk et al. | |
| 8,715,957 B2 | 5/2014 | Osterhout et al. | |
| 8,715,971 B2 | 5/2014 | Pharkya et al. | |
| 8,759,070 B2* | 6/2014 | Papoutsakis | C12N 15/52 |
| | | | 148/243 |
| 8,940,509 B2 | 1/2015 | Burgard et al. | |
| 9,051,552 B2 | 6/2015 | Burk et al. | |
| 9,133,487 B2 | 9/2015 | Burk et al. | |
| 9,175,297 B2 | 11/2015 | Burk et al. | |
| 9,200,297 B2 | 12/2015 | Chen et al. | |
| 2003/0147858 A1 | 8/2003 | Renaud et al. | |
| 2008/0274522 A1 | 11/2008 | Bramucci et al. | |
| 2008/0274524 A1 | 11/2008 | Bramucci et al. | |
| 2008/0274525 A1 | 11/2008 | Bramucci et al. | |
| 2008/0274526 A1 | 11/2008 | Bramucci et al. | |
| 2009/0156779 A1 | 6/2009 | Murase et al. | |
| 2009/0191593 A1 | 7/2009 | Burk et al. | |
| 2010/0105115 A1 | 4/2010 | Simpson et al. | |
| 2010/0316617 A1 | 12/2010 | Renaud et al. | |
| 2011/0003344 A1 | 1/2011 | Burk et al. | |
| 2011/0124063 A1 | 5/2011 | Lynch | |
| 2011/0125118 A1 | 5/2011 | Lynch | |
| 2011/0129899 A1 | 6/2011 | Haselbeck et al. | |
| 2011/0160501 A1 | 6/2011 | Martin et al. | |
| 2011/0195461 A1 | 8/2011 | Butk et al. | |
| 2011/0201068 A1 | 8/2011 | Pharkya et al. | |
| 2011/0201089 A1 | 8/2011 | Burgard et al. | |
| 2011/0207189 A1 | 8/2011 | Burgard et al. | |
| 2011/0212507 A1 | 9/2011 | Burgard et al. | |
| 2011/0229946 A1 | 9/2011 | Haselbeck et al. | |
| 2012/0021478 A1 | 1/2012 | Osterhout et al. | |
| 2012/0322078 A1 | 12/2012 | Mcbride et al. | |
| 2012/0329111 A1 | 12/2012 | Burgard et al. | |
| 2012/0329113 A1 | 12/2012 | Burgard et al. | |
| 2013/0011891 A1 | 1/2013 | Burk et al. | |
| 2013/0029381 A1 | 1/2013 | Haselbeck et al. | |
| 2013/0034884 A1 | 2/2013 | Burgard et al. | |
| 2013/0065279 A1 | 3/2013 | Burk et al. | |
| 2013/0071883 A1 | 3/2013 | Burk et al. | |
| 2013/0122541 A1 | 5/2013 | Lynch et al. | |
| 2013/0189751 A1 | 7/2013 | Haselbeck et al. | |
| 2013/0217060 A1 | 8/2013 | Bramucci et al. | |
| 2013/0217084 A1 | 8/2013 | Wen | |
| 2013/0252294 A1 | 9/2013 | Koppisch et al. | |
| 2013/0267006 A1 | 10/2013 | Koepke et al. | |
| 2013/0337517 A1 | 12/2013 | Razavi-Shirazi et al. | |
| 2014/0011249 A1 | 1/2014 | Burgard et al. | |
| 2014/0030779 A1 | 1/2014 | Pharkya et al. | |
| 2014/0039143 A1 | 2/2014 | Vermeiren | |
| 2014/0088317 A1 | 3/2014 | Wen | |
| 2014/0120591 A1 | 5/2014 | Chen et al. | |
| 2014/0193871 A1 | 7/2014 | Chen et al. | |
| 2014/0256009 A1 | 9/2014 | Marliere | |
| 2015/0050708 A1* | 2/2015 | Burgard | C12P 5/026 |
| | | | 435/158 |
| 2015/0056651 A1 | 2/2015 | Lynch et al. | |
| 2015/0064750 A1 | 3/2015 | Osterhout et al. | |
| 2015/0111266 A1* | 4/2015 | Tizard | C12P 7/18 |
| | | | 435/139 |
| 2015/0148513 A1 | 5/2015 | Pharkya et al. | |
| 2015/0152439 A2 | 6/2015 | Garcez Lopes et al. | |
| 2015/0152445 A1* | 6/2015 | Koepke | C12P 7/28 |
| | | | 435/150 |
| 2015/0275242 A1 | 10/2015 | Osterhout et al. | |
| 2015/0284692 A9* | 10/2015 | Koepke | C12N 9/0006 |
| | | | 435/252.3 |
| 2015/0368680 A1 | 12/2015 | Fontana et al. | |

FOREIGN PATENT DOCUMENTS

| | | |
|---|---|---|
| WO | 2012/080421 | 6/2012 |
| WO | 2012/177599 | 12/2012 |
| WO | 2012/177601 | 12/2012 |
| WO | 2012/177721 | 12/2012 |
| WO | 2013/012975 | 1/2013 |
| WO | 2013/152236 | 10/2013 |
| WO | 2013/181647 | 12/2013 |
| WO | 2014/193473 | 12/2014 |

OTHER PUBLICATIONS

Kisselev L., Polypeptide release factors in prokaryotes and eukaryotes: same function, different structure. Structure, 2002, vol. 10: 8-9.*

Nagarajan et al., Characterizing acetogenic metabolism using a genome-scale metabolic reconstruction of Clostridium Ijungdahlii. Microbial Cell Factories, 2013, vol. 12:118, pp. 1-13.*

Seffernick et al., Melamine deaminase and Atrazine chlorohydrolase: 98 percent identical but functionally different. J. Bacteriol., 2001, vol. 183 (8): 2405-2410.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

Banerjee et al., Lactose-inducible system for metabolic engineering of Clostridium Ijungdahlii. Appl. Environ. Microbiol., 2014, vol. 80(8): 2410-2416.*

Gobner et al., Carbon metabolism of the moderately acid-tolerant acetogen Clostridium drakei isolated from peat. FEMS Microbiol. Lett., 2008, vol. 287: 236-242.*

Sillers et al., Aldehyde-Alcohol dehydrogenase and/or Thiolase overexpression coupled with CoA transferase downregulation lead to higher alcohol titers and selectivity in Clostridium acetobutylicum fermentations. Biotechnol. Bioeng., 2009, vol. 102(1): 38-49.*

Ueki et al., Converting carbon dioxide to butyrate with an engineered strain of Clostridium Ijungdahlii. mBio, 2014, vol. 5(5) e01636-14, pp. 1-10.*

U.S. Appl. No. 62/209,133 to Bryan Tracy et al., filed Aug. 24, 2015.

U.S. Appl. No. 62/121,871 to Bryan Tracy et al., filed Feb. 27, 2015.

U.S. Appl. No. 62/183,034 to Shawn Jones et al., filed Jun. 22, 2015.

U.S. Appl. No. 62/199,548 to Shawn Jones et al., filed Jul. 31, 2015.

U.S. Appl. No. 62/265,239 to Bryan Tracy et al., filed Dec. 9, 2015.

International Search Report issued in PCT/US2016/019760, dated May 17, 2016.

Written Opinion of the International Searching Authority in PCT/US2016/019760, dated May 17, 2016.

Fast et al., "Acetogenic mixotrophy: novel options for yield improvement in biofuels and biochemicals production"*Current Opinion on Biotechnology*, vol. 33, pp. 60-72, 2015.

Ragsdale et al., "Acetogenesis and the Wood-Ljungdahl pathway of $CO_2$ fixation" *Biochimica et Biophysica Acta*, vol. 1784, pp. 1873-1898, 2008.

Tracy et al., "Clostridia: the importance of their exceptional substrate and metabolite diversity for biofuel and biorefinery application" *Current Opinion in Biotechnology*, vol. 23, pp. 364-381, 2012.

Fast et al., "Stoichiometric and energetic analyses of non-photosynthetic $CO_2$-fixation pathways to support synthetic biology strategies for production of fuels and chemicals" *Current Opinion in Chemical Engineering*, vol. 1, pp. 1-16, 2012.

International Search Report and Written Opinion of the ISA issued in PCT/US16/48197, dated Feb. 23, 2017.

* cited by examiner

SEQUENCE LISTING

```
<160> NUMBER OF SEQ ID NOS: 38

<210> SEQ ID NO 1
<211> LENGTH: 1056
<212> TYPE: DNA
<213> ORGANISM: Clostridium ljungdahlii

<400> SEQUENCE: 1
atgaaaggtt ttgcaatgtt aggtattaac aaattaggat ggattgaaaa gaaaaaccca      60
gtgccaggtc cttatgatgc gattgtacat cctctagctg tatccccatg tacatcagat     120
atacatacgg tttttgaagg agcacttggt aataggaaa atatgatttt aggccatgaa      180
gctgtaggtg aaatagccga agttggcagc gaagttaaag attttaaagt tggcgataga     240
gttatcgtac catgcacaac acctgactgg agatctttag aagtccaagc tggttttcag     300
cagcattcaa acggtatgct tgcaggatgg aagttttcca attttaaaga tggtgtattt     360
gcagattact ttcatgtaaa cgatgcagat atgaatcttg ccatactccc agatgaaata     420
cctttagaaa gtgcagttat gatgacagac atgatgacta ctggttttca tggagcagaa     480
cttgcagaca taaaaatggg ctccagcgtt gtagtaattg gtataggagc tgttggatta     540
atgggaatag ccggttccaa acttcgagga gcaggcagaa ttatcggtgt tggaagcaga     600
cctgtttgtg ttgaaacagc taaattttat ggagcaactg atattgtaaa ttataaaaat     660
ggtgatatag ttgaacaaat catggactta actcatggta aaggtgtaga ccgtgtaatc     720
atggcaggcg gtggtgctga aacactagca caagcagtaa ctatggttaa acctggcggc     780
gtaatttcta acatcaacta ccatggaagc ggtgatactt taccaatacc tcgtgttcaa     840
tggggctgcg gcatggctca caaaactata agaggaggat tatgcccggg cggacgtctt     900
agaatggaaa tgctaagaga tcttgttcta tataaacgtg ttgatttgag taaacttgtt     960
actcatgtat ttgatggtgc agaaaatatt gaaaaggccc ttttgcttat gaaaaataag    1020
ccaaaagatt taattaaatc agtagttaca ttctaa                              1056
```

<210> SEQ ID NO 2
<211> LENGTH: 351
<212> TYPE: PRT
<213> ORGANISM: Clostridium ljungdahlii

<400> SEQUENCE: 2

```
Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350
```

<210> SEQ ID NO 3
<211> LENGTH: 1074
<212> TYPE: DNA

<213> ORGANISM: Clostridium ljungdahlii

<400> SEQUENCE: 3

```
atgaaagctg tattgtggta tgataaaaaa gatgtaagag tagaggaaat tgaggaacct      60
aaggtaaaag aaaatgctgt aaaaattaaa gtgaaatggt gtggtatatg tggttctgac     120
ttgcatgagt atttaggagg acctatattt attccagtag gtacgccaca tcctttaagc     180
aagagtactg caccagtagt tttaggacat gagttttcag agaagtagt agaaatagga      240
agcaaggtta caaaatttaa agcaggagat agagttattg tagaacctat agttgcctgt     300
ggaaagtgtc ctgcttgtct tgaaggaaaa tataatttat gtgaagcttt gggatttcat     360
ggactttgtg aagcggcgg cggatttgct gaatacacag tatttcctga agattttgtc     420
cataagatac cagatactat ggactatgag caggctgcac ttgttgagcc tatggcagtt     480
gcccttcatt ctctaagagt tggaaacttt actacaggaa atactgcttt ggttttaggt     540
gcaggaccta taggcttgc aactattcag tgtttaaagg catcagggc aagaattgta      600
attgtatttc agagaaaatc tgtaagacag gaatatgcta gaaatttgg agcagatgta      660
gttttagatc caaatgaggt agatgtaatt gaagaaatta aaaaacttac aggcggcgta     720
ggcgtggata tcttttga acaacaggt gcaaatgtag gattaatac ggcaattcaa        780
gctttaaaat atgaaggtac tgcggtaata accagcgtat gggagaaaaa tgcagaaatc    840
aatccaaatg atcttgtatt tacagaaaag aaggtagttg gtactcttgc ctacagacat    900
gaatttcctt ctacaatagc acttatgaat gatggaagaa taaagacaga cggatatatt    960
acaaagagaa tagcacttga ggacattgta aagaaggat ttgaaacact tacaggacct    1020
gaaaagaaaa acatgtaaa aataattgta actcctgaca aatccttatt gtaa          1074
```

<210> SEQ ID NO 4
<211> LENGTH: 357
<212> TYPE: PRT
<213> ORGANISM: Clostridium ljungdahlii

<400> SEQUENCE: 4

```
Met Lys Ala Val Leu Trp Tyr Asp Lys Lys Asp Val Arg Val Glu Glu
1               5                   10                  15

Ile Glu Glu Pro Lys Val Lys Glu Asn Ala Val Lys Ile Lys Val Lys
                20                  25                  30

Trp Cys Gly Ile Cys Gly Ser Asp Leu His Glu Tyr Leu Gly Gly Pro
            35                  40                  45

Ile Phe Ile Pro Val Gly Thr Pro His Pro Leu Ser Lys Ser Thr Ala
        50                  55                  60

Pro Val Val Leu Gly His Glu Phe Ser Gly Glu Val Val Glu Ile Gly
65                  70                  75                  80

Ser Lys Val Thr Lys Phe Lys Ala Gly Asp Arg Val Ile Val Glu Pro
                85                  90                  95

Ile Val Ala Cys Gly Lys Cys Pro Ala Cys Leu Glu Gly Lys Tyr Asn
            100                 105                 110

Leu Cys Glu Ala Leu Gly Phe His Gly Leu Cys Gly Ser Gly Gly Gly
        115                 120                 125

Phe Ala Glu Tyr Thr Val Phe Pro Glu Asp Phe Val His Lys Ile Pro
    130                 135                 140

Asp Thr Met Asp Tyr Glu Gln Ala Ala Leu Val Glu Pro Met Ala Val
145                 150                 155                 160

Ala Leu His Ser Leu Arg Val Gly Asn Phe Thr Thr Gly Asn Thr Ala
```

```
                165                 170                 175
Leu Val Leu Gly Ala Gly Pro Ile Gly Leu Ala Thr Ile Gln Cys Leu
            180                 185                 190

Lys Ala Ser Gly Ala Arg Ile Val Ile Val Phe Gln Arg Lys Ser Val
            195                 200                 205

Arg Gln Glu Tyr Ala Lys Lys Phe Gly Ala Asp Val Val Leu Asp Pro
            210                 215                 220

Asn Glu Val Asp Val Ile Glu Ile Lys Lys Leu Thr Gly Val
225                 230                 235                 240

Gly Val Asp Thr Ser Phe Glu Thr Thr Gly Ala Asn Val Gly Ile Asn
                245                 250                 255

Thr Ala Ile Gln Ala Leu Lys Tyr Glu Gly Thr Ala Val Ile Thr Ser
            260                 265                 270

Val Trp Glu Lys Asn Ala Glu Ile Asn Pro Asn Asp Leu Val Phe Thr
            275                 280                 285

Glu Lys Lys Val Val Gly Thr Leu Ala Tyr Arg His Glu Phe Pro Ser
            290                 295                 300

Thr Ile Ala Leu Met Asn Asp Gly Arg Ile Lys Thr Asp Gly Tyr Ile
305                 310                 315                 320

Thr Lys Arg Ile Ala Leu Glu Asp Ile Val Lys Glu Gly Phe Glu Thr
                325                 330                 335

Leu Thr Gly Pro Glu Lys Lys Lys His Val Lys Ile Ile Val Thr Pro
            340                 345                 350

Asp Lys Ser Leu Leu
        355

<210> SEQ ID NO 5
<211> LENGTH: 1317
<212> TYPE: DNA
<213> ORGANISM: Clostridium acetobutylicum

<400> SEQUENCE: 5
atgccattat taattgttgt tattggcgtc gcattactat tactacttat gattaaattc    60
aaagtaaacg gattcatatc cctaattctt gtagctttgg ttgttggtat cgccgaaggt   120
atgaatcctg caaaagctgt ttcttcaatt caaaacggtg ttggaagcac cttaagcagt   180
ttggcactaa ttttaggttt tggtgctatg tttggaaaat aatagctga ttctggtgct   240 gctcaaagga tttctagaag tttaattaat aaatttggtg taaaaaaaat tcaatgggct   300
gttgtattaa cgggtttcat agttggcatt gctatgttct atgaggtagg ttttgttcta   360
cttatacctc ttgttttttac tattgctgaa ttcacagaac ttcctctttt atacataggc   420
gttcctatgg ctgcagcttt atctgtcact cacggatttt tacctcctca ccctggacct   480
gttgcaatag ctacaatata tggtgcaagc attagcatga ctcttgtata tggaattgta   540
atagctatac ctacagtaat agttgcagga cctgttttga ctaagttttt aaaacgtttt   600
gatcataaat cttcaaaaaa ccttttttaaa actaaggtct tgatgaaga tgaaatgcca   660 agtttctcat taagcgtatt aactgctatt gttcctccta ttcttatggc cttttcagct   720
gtttgtgaaa tcacactacc aaaaacatct cctataagac attttgcaga attcgttgga   780
agtcctatga tggcaatgtt tatatcaatc attgtagcta tctttactct tggtataatg   840
cgcggaaaga aaatggaaga ataatgaga actttagctg aagccgcaag ttccattgca   900
atgatccttt taatagtagc tggaggtggt gccttcaagc aagtactaat agacagtggt   960 gttggaaaaat atatcgcttc tattatggtt ggaagtaata tatctcctct aatcttggct  1020
```

```
tgggcgattg cagcaatttt aagattatct cttggttctg ccactgtttc tgctatgact    1080
actgccggta tagtacttcc tcttattcct tcaacccatg caaacccagc attaatggtt    1140
ttagcaactg gcgcaggtag tcttattttc tctcatgtaa acgatccagg tttctggatg    1200
ttcaaagaat attttggact tagcatagga gaaacaatgg cttcatggtc tactttagaa    1260
actataattt caattatggg gttaattggt gttttagctt taaatatggt tggatag       1317
```

<210> SEQ ID NO 6
<211> LENGTH: 438
<212> TYPE: PRT
<213> ORGANISM: Clostridium acetobutylicum

<400> SEQUENCE: 6

```
Met Pro Leu Leu Ile Val Val Gly Val Ala Leu Leu Leu Leu
1               5                   10                  15

Met Ile Lys Phe Lys Val Asn Gly Phe Ile Ser Leu Ile Leu Val Ala
            20                  25                  30

Leu Val Val Gly Ile Ala Glu Gly Met Asn Pro Ala Lys Ala Val Ser
        35                  40                  45

Ser Ile Gln Asn Gly Val Gly Ser Thr Leu Ser Leu Ala Leu Ile
    50                  55                  60

Leu Gly Phe Gly Ala Met Phe Gly Lys Leu Ile Ala Asp Ser Gly Ala
65                  70                  75                  80

Ala Gln Arg Ile Ser Arg Ser Leu Ile Asn Lys Phe Gly Val Lys Lys
                85                  90                  95

Ile Gln Trp Ala Val Val Leu Thr Gly Phe Ile Val Gly Ile Ala Met
            100                 105                 110

Phe Tyr Glu Val Gly Phe Val Leu Leu Ile Pro Leu Val Phe Thr Ile
        115                 120                 125

Ala Glu Phe Thr Glu Leu Pro Leu Leu Tyr Ile Gly Val Pro Met Ala
    130                 135                 140

Ala Ala Leu Ser Val Thr His Gly Phe Leu Pro Pro His Pro Gly Pro
145                 150                 155                 160

Val Ala Ile Ala Thr Ile Tyr Gly Ala Ser Ile Ser Met Thr Leu Val
                165                 170                 175

Tyr Gly Ile Val Ile Ala Ile Pro Thr Val Ile Ala Gly Pro Val
            180                 185                 190

Leu Thr Lys Phe Leu Lys Arg Phe Asp His Lys Ser Ser Lys Asn Leu
        195                 200                 205

Phe Lys Thr Lys Val Phe Asp Glu Asp Glu Met Pro Ser Phe Ser Leu
    210                 215                 220

Ser Val Leu Thr Ala Ile Val Pro Pro Ile Leu Met Ala Phe Ser Ala
225                 230                 235                 240

Val Cys Glu Ile Thr Leu Pro Lys Thr Ser Pro Ile Arg His Phe Ala
                245                 250                 255

Glu Phe Val Gly Ser Pro Met Met Ala Met Phe Ile Ser Ile Ile Val
            260                 265                 270

Ala Ile Phe Thr Leu Gly Ile Met Arg Gly Lys Lys Met Glu Glu Ile
        275                 280                 285

Met Arg Thr Leu Ala Glu Ala Ser Ser Ile Ala Met Ile Leu Leu
    290                 295                 300

Ile Val Ala Gly Gly Ala Phe Lys Gln Val Leu Ile Asp Ser Gly
305                 310                 315                 320
```

```
Val Gly Lys Tyr Ile Ala Ser Ile Met Val Gly Ser Asn Ile Ser Pro
            325                 330                 335

Leu Ile Leu Ala Trp Ala Ile Ala Ala Ile Leu Arg Leu Ser Leu Gly
            340                 345                 350

Ser Ala Thr Val Ser Ala Met Thr Thr Ala Gly Ile Val Leu Pro Leu
            355                 360                 365

Ile Pro Ser Thr His Ala Asn Pro Ala Leu Met Val Leu Ala Thr Gly
            370                 375                 380

Ala Gly Ser Leu Ile Phe Ser His Val Asn Asp Pro Gly Phe Trp Met
385                 390                 395                 400

Phe Lys Glu Tyr Phe Gly Leu Ser Ile Gly Glu Thr Met Ala Ser Trp
            405                 410                 415

Ser Thr Leu Glu Thr Ile Ile Ser Ile Met Gly Leu Ile Gly Val Leu
            420                 425                 430

Ala Leu Asn Met Val Gly
            435

<210> SEQ ID NO 7
<211> LENGTH: 1350
<212> TYPE: DNA
<213> ORGANISM: Clostridium acetobutylicum

<400> SEQUENCE: 7
```

| | | |
|---|---|---|
| atgaaaaagt taagcttaaa ggaaaaaatc tcttatggac ttggcgattt tggaaatggt | 60 |
| ttcatgtttg atttgggtca atcatatctg ttaaaattct atacagacgt cgtaggtata | 120 |
| gctgcaggag cggcgggagg aatattcttc ttcactaaaa tatttgatgc tttcatggat | 180 |
| cctatagctg gaacaataat agattcaagg aaaccaggta aaacggtaa attcaaacct | 240 |
| attatgttct tgcaagtat agtacttgct atattgacag taataacgtt tactaaccct | 300 |
| ggaaaaactg ctacatcaaa actattattt gcatatgcaa catatatgat atgggacttt | 360 |
| ggatactcat ttacaaatgt tccgtatgga tctcttggat cagttataac tcaagatgtt | 420 |
| caagaaagaa cttcgttggc gactttaga cagataggtt cttcaggagc tcttcttata | 480 |
| acaagtgtta tatttatgcc tcttgtttta gtatttcata cccagcaat aggttatcca | 540 |
| gtagttgcgg gtataatggg gttaatagga atattatcat tctacatgac atacaaaaat | 600 |
| actagagaag ttgttgcgcc agctgaaaac gttaagaagg aaaaaataac accaaagtca | 660 |
| attgcggtta caatatttac aaatagagca ttattaacat taatattaat gactatattc | 720 |
| tctatttcgg cttacaatat tagaagttca ttaattgttt attactgcca atataatctt | 780 |
| ggaaacgtta ctttattacc atatataaat ttcttcacta taggatgtgc tgttttaggt | 840 |
| gtttcttca tgccaaagct agttggtaga tttggtaaaa aagaactgc tatcatagga | 900 |
| tttttgataa gtgttattgc agatagtata aactttcttc ttccaggaaa tatatatact | 960 |
| ttcacaatat tattagcaat tggatttata ggtataagca ttcctaatgg aataacttgg | 1020 |
| gcttttgtat cagacagtat cgattatggt gagtggagaa caggaactag aagagaagga | 1080 |
| ataacttact ctgtatttaa tttcgcaaga aaacttgctc agtcaatagc tggattatta | 1140 |
| tcaggatggg gacttggatt tgttggttat gtagctaaca agaaacaaag tgcacatgca | 1200 |
| ttatttggaa taaaagcatt attgatggct tatccagcgg tagcgctttt agtagcagca | 1260 |
| ttaataattg gtttattgta caacctttca gataagaaat ttactgaaat aatagaagaa | 1320 |
| ttagacgcta gaaaaggtaa aacagtttaa | 1350 |

```
<210> SEQ ID NO 8
<211> LENGTH: 449
<212> TYPE: PRT
<213> ORGANISM: Clostridium acetobutylicum

<400> SEQUENCE: 8

Met Lys Lys Leu Ser Leu Lys Glu Lys Ile Ser Tyr Gly Leu Gly Asp
1               5                   10                  15

Phe Gly Asn Gly Phe Met Phe Asp Leu Gly Gln Ser Tyr Leu Leu Lys
            20                  25                  30

Phe Tyr Thr Asp Val Val Gly Ile Ala Ala Gly Ala Ala Gly Gly Ile
        35                  40                  45

Phe Phe Phe Thr Lys Ile Phe Asp Ala Phe Met Asp Pro Ile Ala Gly
    50                  55                  60

Thr Ile Ile Asp Ser Arg Lys Pro Gly Lys Asn Gly Lys Phe Lys Pro
65                  70                  75                  80

Ile Met Phe Phe Ala Ser Ile Val Leu Ala Ile Leu Thr Val Ile Thr
                85                  90                  95

Phe Thr Asn Pro Gly Lys Thr Ala Thr Ser Lys Leu Leu Phe Ala Tyr
            100                 105                 110

Ala Thr Tyr Met Ile Trp Gly Leu Gly Tyr Ser Phe Thr Asn Val Pro
        115                 120                 125

Tyr Gly Ser Leu Gly Ser Val Ile Thr Gln Asp Val Gln Glu Arg Thr
    130                 135                 140

Ser Leu Ala Thr Phe Arg Gln Ile Gly Ser Ser Gly Ala Leu Leu Ile
145                 150                 155                 160

Thr Ser Val Ile Phe Met Pro Leu Val Leu Val Phe His Asn Pro Ala
                165                 170                 175

Ile Gly Tyr Pro Val Val Ala Gly Ile Met Gly Leu Ile Gly Ile Leu
            180                 185                 190

Ser Phe Tyr Met Thr Tyr Lys Asn Thr Arg Glu Val Val Ala Pro Ala
        195                 200                 205

Glu Asn Val Lys Lys Glu Lys Ile Thr Pro Lys Ser Ile Ala Val Thr
    210                 215                 220

Ile Phe Thr Asn Arg Ala Leu Leu Thr Leu Ile Leu Met Thr Ile Phe
225                 230                 235                 240

Ser Ile Ser Ala Tyr Asn Ile Arg Ser Ser Leu Ile Val Tyr Tyr Cys
                245                 250                 255

Gln Tyr Asn Leu Gly Asn Val Thr Leu Leu Pro Tyr Ile Asn Phe Phe
            260                 265                 270

Thr Ile Gly Cys Ala Val Leu Gly Val Ser Phe Met Pro Lys Leu Val
        275                 280                 285

Gly Arg Phe Gly Lys Lys Arg Thr Ala Ile Ile Gly Phe Leu Ile Ser
    290                 295                 300

Val Ile Ala Asp Ser Ile Asn Phe Leu Leu Pro Gly Asn Ile Tyr Thr
305                 310                 315                 320

Phe Thr Ile Leu Leu Ala Ile Gly Phe Ile Gly Ile Ser Ile Pro Asn
                325                 330                 335

Gly Ile Thr Trp Ala Phe Val Ser Asp Ser Ile Asp Tyr Gly Glu Trp
            340                 345                 350

Arg Thr Gly Thr Arg Arg Glu Gly Ile Thr Tyr Ser Val Phe Asn Phe
        355                 360                 365

Ala Arg Lys Leu Ala Gln Ser Ile Ala Gly Leu Leu Ser Gly Trp Gly
    370                 375                 380
```

Leu Gly Phe Val Gly Tyr Val Ala Asn Lys Lys Gln Ser Ala His Ala
385                 390                 395                 400

Leu Phe Gly Ile Lys Ala Leu Leu Met Ala Tyr Pro Val Ala Leu
            405                 410                 415

Leu Val Ala Ala Leu Ile Ile Gly Leu Leu Tyr Asn Leu Ser Asp Lys
            420                 425                 430

Lys Phe Thr Glu Ile Ile Glu Glu Leu Asp Ala Arg Lys Gly Lys Thr
        435                 440                 445

Val

<210> SEQ ID NO 9
<211> LENGTH: 1317
<212> TYPE: DNA
<213> ORGANISM: Escherichia coli

<400> SEQUENCE: 9
atgggaaaca catcaataca aacgcagagt taccgtgcgg tagataaaga tgcagggcaa      60
agcagaagtt acattattcc attcgcgctg ctgtgctcac tgttttttct ttgggcggta     120
gccaataacc ttaacgacat tttattacct caattccagc aggcttttac gctgacaaat     180
ttccaggctg gcctgatcca atcggccttt tactttggtt atttcattat cccaatccct     240
gctgggatat tgatgaaaaa actcagttat aaagcaggga ttattaccgg ttatttttta     300
tatgccttgg gtgctgcatt attctggccc gccgcagaaa taatgaacta cccttgtttt     360
ttagttggcc tatttattat tgcagccgga ttaggttgtc tggaaactgc cgcaaaccct     420
tttgttacgg tatttagggcc ggaaagtagt ggtcacttcc gcttaaatct tgcgcaaaca     480
tttaactcgt ttggcgcaat tatcgcggtt gtctttgggc aaagtcttat tttgtctaac     540
gtgccacatc aatcgcaaga cgttctcgat aaaatgtctc cagagcaatt gagtgcgtat     600
aaacacagcc tggtattatc ggtacagaca ccttatatga tcatcgtggc tatcgtgtta     660
ctggtcgccc tgctgatcat gctgacgaaa ttccccggcat tgcagagtga taatcacagt     720
gacgccaaac aaggatcgtt ctccgcatcg ctttctcgcc tggcgcgtat tcgccactgg     780
cgctgggcgg tattagcgca attctgctat gtcggcgcac aaacggcctg ctggagctat     840
ttgattcgct acgctgtaga agaaattcca ggtatgactg caggctttgc cgctaactat     900 taaccggaa ccatggtgtg cttctttatt ggtcgtttca ccggtacctg gctcatcagt     960
cgcttcgcac cacacaaagt cctggccgcc tacgcattaa tcgctatggc actgtgcctg    1020
atctcagcct cgctggcgg tcatgtgggc ttaatagccc tgactttatg cagcgccttt    1080
atgtcgattc agtacccaac aatcttctcg ctgggcatta gaatctcgg ccaggacacc    1140 aaatatggtt cgtccttcat cgttatgacc attattggcg gcggtattgt cactccggtc    1200
atgggttttg tcagtgacgc ggcgggcaac atccccactg ctgaactgat ccccgcactc    1260
tgcttcgcgg tcatctttat ctttgcccgt tccgttctc aaacggcaac taactga       1317

<210> SEQ ID NO 10
<211> LENGTH: 438
<212> TYPE: PRT
<213> ORGANISM: Escherichia coli

<400> SEQUENCE: 10

Met Gly Asn Thr Ser Ile Gln Thr Gln Ser Tyr Arg Ala Val Asp Lys
1               5                   10                  15

Asp Ala Gly Gln Ser Arg Ser Tyr Ile Ile Pro Phe Ala Leu Leu Cys
            20                  25                  30

-continued

```
Ser Leu Phe Phe Leu Trp Ala Val Ala Asn Asn Leu Asn Asp Ile Leu
         35                  40                  45

Leu Pro Gln Phe Gln Gln Ala Phe Thr Leu Thr Asn Phe Gln Ala Gly
 50                  55                  60

Leu Ile Gln Ser Ala Phe Tyr Phe Gly Tyr Phe Ile Ile Pro Ile Pro
 65                  70                  75                  80

Ala Gly Ile Leu Met Lys Lys Leu Ser Tyr Lys Ala Gly Ile Ile Thr
                 85                  90                  95

Gly Leu Phe Leu Tyr Ala Leu Gly Ala Ala Leu Phe Trp Pro Ala Ala
                100                 105                 110

Glu Ile Met Asn Tyr Thr Leu Phe Leu Val Gly Leu Phe Ile Ile Ala
                115                 120                 125

Ala Gly Leu Gly Cys Leu Glu Thr Ala Ala Asn Pro Phe Val Thr Val
                130                 135                 140

Leu Gly Pro Glu Ser Ser Gly His Phe Arg Leu Asn Leu Ala Gln Thr
145                 150                 155                 160

Phe Asn Ser Phe Gly Ala Ile Ile Ala Val Val Phe Gly Gln Ser Leu
                165                 170                 175

Ile Leu Ser Asn Val Pro His Gln Ser Gln Asp Val Leu Asp Lys Met
                180                 185                 190

Ser Pro Glu Gln Leu Ser Ala Tyr Lys His Ser Leu Val Leu Ser Val
                195                 200                 205

Gln Thr Pro Tyr Met Ile Ile Val Ala Ile Val Leu Leu Val Ala Leu
                210                 215                 220

Leu Ile Met Leu Thr Lys Phe Pro Ala Leu Gln Ser Asp Asn His Ser
225                 230                 235                 240

Asp Ala Lys Gln Gly Ser Phe Ser Ala Ser Leu Ser Arg Leu Ala Arg
                245                 250                 255

Ile Arg His Trp Arg Trp Ala Val Leu Ala Gln Phe Cys Tyr Val Gly
                260                 265                 270

Ala Gln Thr Ala Cys Trp Ser Tyr Leu Ile Arg Tyr Ala Val Glu Glu
                275                 280                 285

Ile Pro Gly Met Thr Ala Gly Phe Ala Ala Asn Tyr Leu Thr Gly Thr
                290                 295                 300

Met Val Cys Phe Phe Ile Gly Arg Phe Thr Gly Thr Trp Leu Ile Ser
305                 310                 315                 320

Arg Phe Ala Pro His Lys Val Leu Ala Ala Tyr Ala Leu Ile Ala Met
                325                 330                 335

Ala Leu Cys Leu Ile Ser Ala Phe Ala Gly Gly His Val Gly Leu Ile
                340                 345                 350

Ala Leu Thr Leu Cys Ser Ala Phe Met Ser Ile Gln Tyr Pro Thr Ile
                355                 360                 365

Phe Ser Leu Gly Ile Lys Asn Leu Gly Gln Asp Thr Lys Tyr Gly Ser
370                 375                 380

Ser Phe Ile Val Met Thr Ile Ile Gly Gly Ile Val Thr Pro Val
385                 390                 395                 400

Met Gly Phe Val Ser Asp Ala Ala Gly Asn Ile Pro Thr Ala Glu Leu
                405                 410                 415

Ile Pro Ala Leu Cys Phe Ala Val Ile Phe Ile Phe Ala Arg Phe Arg
                420                 425                 430

Ser Gln Thr Ala Thr Asn
                435
```

<210> SEQ ID NO 11
<211> LENGTH: 1179
<212> TYPE: DNA
<213> ORGANISM: Clostridium acetobutylicum

<400> SEQUENCE: 11

| | | | | | |
|---|---|---|---|---|---|
| atgaaagaag | ttgtaatagc | tagtgcagta | agaacagcga | ttggatctta | tggaaagtct | 60 |
| cttaaggatg | taccagcagt | agatttagga | gctacagcta | aaaggaagc | agttaaaaaa | 120 |
| gcaggaataa | aaccagagga | tgttaatgaa | gtcattttag | gaaatgttct | tcaagcaggt | 180 |
| ttaggacaga | atccagcaag | acaggcatct | tttaaagcag | gattaccagt | tgaaattcca | 240 |
| gctatgacta | ttaataaggt | ttgtggttca | ggacttagaa | cagttagctt | agcagcacaa | 300 |
| attataaaag | caggagatgc | tgacgtaata | atagcaggtg | gtatggaaaa | tatgtctaga | 360 |
| gctcccttact | tagcgaataa | cgctagatgg | ggatatagaa | tgggaaacgc | taaatttgtt | 420 |
| gatgaaatga | tcactgacgg | attgtgggat | gcatttaatg | attaccacat | gggaataaca | 480 |
| gcagaaaaca | tagctgagag | atggaacatt | tcaagagaag | aacaagatga | gtttgctctt | 540 |
| gcatcacaaa | aaaagctga | agaagctata | aaatcaggtc | aatttaaaga | tgaaatagtt | 600 |
| cctgtagtaa | ttaaaggcag | aaagggagaa | actgtagttg | atacagatga | gcaccctaga | 660 |
| tttggatcaa | ctatagaagg | acttgcaaaa | ttaaaacctg | ccttcaaaaa | agatggaaca | 720 |
| gttacagctg | gtaatgcatc | aggattaaat | gactgtgcag | cagtacttgt | aatcatgagt | 780 |
| gcagaaaaag | ctaaagagct | tggagtaaaa | ccacttgcta | agatagttc | ttatggttca | 840 |
| gcaggagttg | acccagcaat | aatgggatat | ggacctttct | atgcaacaaa | agcagctatt | 900 |
| gaaaaagcag | gttggacagt | tgatgaatta | gatttaatag | aatcaaatga | agcttttgca | 960 |
| gctcaaagtt | tagcagtagc | aaaagattta | aaatttgata | tgaataaagt | aaatgtaaat | 1020 |
| ggaggagcta | ttgcccttgg | tcatccaatt | ggagcatcag | gtgcaagaat | actcgttact | 1080 |
| cttgtacacg | caatgcaaaa | aagagatgca | aaaaaaggct | tagcaacttt | atgtataggt | 1140 |
| ggcggacaag | gaacagcaat | attgctagaa | aagtgctag | | | 1179 |

<210> SEQ ID NO 12
<211> LENGTH: 392
<212> TYPE: PRT
<213> ORGANISM: Clostridium acetobutylicum

<400> SEQUENCE: 12

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
                180                 185                 190

Gly Gln Phe Lys Asp Glu Ile Val Pro Val Ile Lys Gly Arg Lys
        195                 200                 205

Gly Glu Thr Val Val Asp Thr Asp Glu His Pro Arg Phe Gly Ser Thr
        210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
                260                 265                 270

Ala Lys Ile Val Ser Tyr Gly Ser Ala Gly Val Asp Pro Ala Ile Met
            275                 280                 285

Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
                340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
        370                 375                 380

Thr Ala Ile Leu Leu Glu Lys Cys
385                 390

<210> SEQ ID NO 13
<211> LENGTH: 849
<212> TYPE: DNA
<213> ORGANISM: Clostridium acetobutylicum

<400> SEQUENCE: 13
atgaaaaagg tatgtgttat aggtgcaggt actatgggtt caggaattgc tcaggcattt    60
gcagctaaag gatttgaagt agtattaaga gatattaaag atgaatttgt tgatagagga   120 ttagattta tcaataaaaa tctttctaaa ttagttaaaa aggaaagat agaagaagct   180 actaaagttg aaatcttaac tagaatttcc ggaacagttg accttaatat ggcagctgat   240
tgcgatttag ttatagaagc agctgttgaa agaatggata ttaaaaagca gattttgct   300 gacttagaca atatatgcaa gccagaaaca attcttgcat caaatacatc atcacttca   360 ataacagaag tggcatcagc aactaaaga cctgataagg ttataggtat gcatttcttt   420
aatccagctc ctgttatgaa gcttgtagag gtaataagag gaatagctac atcacaagaa   480
acttttgatg cagttaaaga gacatctata gcaataggaa aagatcctgt agaagtagca   540
gaagcaccag gatttgttgt aaatagaata ttaatacca tgattaatga agcagttggt   600

```
atattagcag aaggaatagc ttcagtagaa gacatagata aagctatgaa acttggagct    660
aatcacccaa tgggaccatt agaattaggt gattttatag gtcttgatat atgtcttgct    720
ataatggatg ttttatactc agaaactgga gattctaagt atagaccaca tacattactt    780
aagaagtatg taagagcagg atggcttgga agaaaatcag gaaaaggttt ctacgattat    840
tcaaaataa                                                           849
```

<210> SEQ ID NO 14
<211> LENGTH: 282
<212> TYPE: PRT
<213> ORGANISM: Clostridium acetobutylicum

<400> SEQUENCE: 14

```
Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280
```

<210> SEQ ID NO 15
<211> LENGTH: 786
<212> TYPE: DNA
<213> ORGANISM: Clostridium acetobutylicum

<400> SEQUENCE: 15

```
atggaactaa acaatgtcat ccttgaaaag gaaggtaaag ttgctgtagt taccattaac    60
agacctaaag cattaaatgc gttaaatagt gatacactaa agaaatgga ttatgttata   120
ggtgaaattg aaaatgatag cgaagtactt gcagtaattt taactggagc aggagaaaaa   180
tcatttgtag caggagcaga tatttctgag atgaaggaaa tgaataccat tgaaggtaga   240
aaattcggga tacttggaaa taagtgtttt agaagattag aacttcttga aaagcctgta   300
atagcagctg ttaatggttt tgctttagga ggcggatgcg aaatagctat gtcttgtgat   360
ataagaatag cttcaagcaa cgcaagattt ggtcaaccag aagtaggtct cggaataaca   420
cctggttttg gtggtacaca agactttca agattagttg gaatgggcat ggcaaagcag   480
cttatattta ctgcacaaaa tataaaggca gatgaagcat taagaatcgg acttgtaaat   540
aaggtagtag aacctagtga attaatgaat acagcaaaag aaattgcaaa caaaattgtg   600
agcaatgctc cagtagctgt taagttaagc aaacaggcta ttaataggg aatgcagtgt   660
gatattgata ctgctttagc atttgaatca gaagcatttg agaatgcctt ttcaacagag   720
gatcaaaagg atgcaatgac agctttcata gagaaaagaa aaattgaagg cttcaaaaat   780
agatag                                                             786
```

<210> SEQ ID NO 16
<211> LENGTH: 261
<212> TYPE: PRT
<213> ORGANISM: Clostridium acetobutylicum

<400> SEQUENCE: 16

```
Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220
```

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
            245                 250                 255

Gly Phe Lys Asn Arg
        260

<210> SEQ ID NO 17
<211> LENGTH: 2589
<212> TYPE: DNA
<213> ORGANISM: Clostridium acetobutylicum

<400> SEQUENCE: 17

```
atgaaagtca caacagtaaa ggaattagat gaaaaactca aggtaattaa agaagctcaa      60
aaaaaattct cttgttactc gcaagaaatg gttgatgaaa tctttagaaa tgcagcaatg     120
gcagcaatcg acgcaaggat agagctagca aaagcagctg ttttggaaac cggtatgggc     180
ttagttgaag acaaggttat aaaaaatcat tttgcaggcg aatacatcta taacaaatat     240
aaggatgaaa aacctgcgg tataattgaa cgaaatgaac cctacggaat tacaaaaata     300
gcagaaccta taggagttgt agctgctata tccctgtaa caaacccac atcaacaaca     360 atatttaaat ccttaatatc ccttaaaact agaaatggaa ttttcttttc gcctcaccca     420
agggcaaaaa atccacaat actagcagct aaaacaatac ttgatgcagc cgttaagagt     480
ggtgccccgg aaaatataat aggttggata gatgaacctt caattgaact aactcaatat     540
ttaatgcaaa aagcagatat aacccttgca actggtggtc cctcactagt taaatctgct     600
tattcttccg gaaaaccagc aataggtgtt ggtccgggta acacccccagt aataattgat     660 gaatctgctc atataaaaat ggcagtaagt tcaattatat atccaaaac ctatgataat     720 ggtgttatat gtgcttctga acaatctgta atagtcttaa atccatata taacaaggta     780 aaagatgagt ccaagaaag aggagcttat ataataaaga aaacgaatt ggataaagtc     840 cgtgaagtga ttttaaaga tggatccgta aaccctaaaa tagtcggaca gtcagcttat     900
actatagcag ctatggctgg cataaaaagta cctaaaacca caagaatatt aataggagaa     960
gttacctcct taggtgaaga gaaccttttt gcccacgaaa aactatctcc tgttttggct    1020
atgtatgagg ctgacaattt tgatgatgct ttaaaaaaag cagtaactct aataaactta    1080
ggaggcctcg ccataccctc aggaatatat gcagatgaaa taaagcacg agataaaata    1140 gatagattta gtagtgccat gaaaaccgta agaaccttg taaatatccc aacctcacaa    1200
ggtgcaagtg agatctata taatttaga ataccacctt ctttcacgct tggctgcgga    1260
tttttgggag gaaattctgt ttccgagaat gttggtccaa acatctttt gaatattaaa    1320 accgtagctg aaaggagaga aaacatgctt tggtttagag ttccacataa agtatatttt    1380
aagttcggtt gtcttcaatt tgcttaaaa gatttaaaag atctaaagaa aaaagagcc    1440 tttatagtta ctgatagtga ccccctataat ttaaactatg ttgattcaat aataaaaata    1500
cttgagcacc tagatattga ttttaaagta tttaataagg ttggaagaga agctgatctt    1560
aaaaccataa aaaagcaac tgaagaaatg tcctccttta tgccagacac tataatagct    1620
ttaggtggta ccccctgaaat gagctctgca aagctaatgt gggtactata tgaacatcca    1680
gaagtaaaat ttgaagatct tgcaataaaa tttatggaca taagaaagag aatatatact    1740
ttcccaaaac tcggtaaaaa ggctatgtta gttgcaatta caacttctgc tggttccggt    1800
tctgaggtta ctccttttgc tttagtaact gacaataaca ctggaaataa gtacatgtta    1860
```

```
gcagattatg aaatgacacc aaatatggca attgtagatg cagaacttat gatgaaaatg    1920
ccaaagggat taaccgctta ttcaggtata gatgcactag taaatagtat agaagcatac    1980
acatccgtat atgcttcaga atacacaaac ggactagcac tagaggcaat acgattaata    2040
tttaaatatt tgcctgaggc ttacaaaaac ggaagaacca atgaaaaagc aagagagaaa    2100
atggctcacg cttcaactat ggcaggtatg gcatccgcta atgcatttct aggtctatgt    2160
cattccatgg caataaaatt aagttcagaa cacaatattc ctagtggcat tgccaatgca    2220
ttactaatag aagaagtaat aaaatttaac gcagttgata atcctgtaaa acaagcccct    2280
tgcccacaat ataagtatcc aaacaccata tttagatatg ctcgaattgc agattatata    2340
aagcttggag gaaatactga tgaggaaaag gtagatctct taattaacaa atacatgaa    2400 ctaaaaaaag ctttaaatat accaacttca ataaggatg caggtgtttt ggaggaaaac    2460
ttctattcct cccttgatag aatatctgaa cttgcactag atgatcaatg cacaggcgct    2520
aatcctagat ttcctcttac aagtgagata aagaaatgt atataaattg ttttaaaaaa    2580
caaccttaa                                                             2589

<210> SEQ ID NO 18
<211> LENGTH: 862
<212> TYPE: PRT
<213> ORGANISM: Clostridium acetobutylicum

<400> SEQUENCE: 18

Met Lys Val Thr Thr Val Lys Glu Leu Asp Glu Lys Leu Lys Val Ile
1               5                   10                  15

Lys Glu Ala Gln Lys Lys Phe Ser Cys Tyr Ser Gln Glu Met Val Asp
            20                  25                  30

Glu Ile Phe Arg Asn Ala Ala Met Ala Ala Ile Asp Ala Arg Ile Glu
        35                  40                  45

Leu Ala Lys Ala Ala Val Leu Glu Thr Gly Met Gly Leu Val Glu Asp
    50                  55                  60

Lys Val Ile Lys Asn His Phe Ala Gly Glu Tyr Ile Tyr Asn Lys Tyr
65                  70                  75                  80

Lys Asp Glu Lys Thr Cys Gly Ile Ile Glu Arg Asn Glu Pro Tyr Gly
                85                  90                  95

Ile Thr Lys Ile Ala Glu Pro Ile Gly Val Val Ala Ala Ile Ile Pro
            100                 105                 110

Val Thr Asn Pro Thr Ser Thr Thr Ile Phe Lys Ser Leu Ile Ser Leu
        115                 120                 125

Lys Thr Arg Asn Gly Ile Phe Phe Ser Pro His Pro Arg Ala Lys Lys
    130                 135                 140

Ser Thr Ile Leu Ala Ala Lys Thr Ile Leu Asp Ala Ala Val Lys Ser
145                 150                 155                 160

Gly Ala Pro Glu Asn Ile Ile Gly Trp Ile Asp Glu Pro Ser Ile Glu
                165                 170                 175

Leu Thr Gln Tyr Leu Met Gln Lys Ala Asp Ile Thr Leu Ala Thr Gly
            180                 185                 190

Gly Pro Ser Leu Val Lys Ser Ala Tyr Ser Ser Gly Lys Pro Ala Ile
        195                 200                 205

Gly Val Gly Pro Gly Asn Thr Pro Val Ile Ile Asp Glu Ser Ala His
    210                 215                 220

Ile Lys Met Ala Val Ser Ser Ile Ile Leu Ser Lys Thr Tyr Asp Asn
225                 230                 235                 240
```

-continued

Gly Val Ile Cys Ala Ser Glu Gln Ser Val Ile Val Leu Lys Ser Ile
                245                 250                 255

Tyr Asn Lys Val Lys Asp Glu Phe Gln Glu Arg Gly Ala Tyr Ile Ile
                260                 265                 270

Lys Lys Asn Glu Leu Asp Lys Val Arg Glu Val Ile Phe Lys Asp Gly
                275                 280                 285

Ser Val Asn Pro Lys Ile Val Gly Gln Ser Ala Tyr Thr Ile Ala Ala
                290                 295                 300

Met Ala Gly Ile Lys Val Pro Lys Thr Thr Arg Ile Leu Ile Gly Glu
305                 310                 315                 320

Val Thr Ser Leu Gly Glu Glu Pro Phe Ala His Glu Lys Leu Ser
                325                 330                 335

Pro Val Leu Ala Met Tyr Glu Ala Asp Asn Phe Asp Asp Ala Leu Lys
                340                 345                 350

Lys Ala Val Thr Leu Ile Asn Leu Gly Gly Leu Gly His Thr Ser Gly
                355                 360                 365

Ile Tyr Ala Asp Glu Ile Lys Ala Arg Asp Lys Ile Asp Arg Phe Ser
                370                 375                 380

Ser Ala Met Lys Thr Val Arg Thr Phe Val Asn Ile Pro Thr Ser Gln
385                 390                 395                 400

Gly Ala Ser Gly Asp Leu Tyr Asn Phe Arg Ile Pro Pro Ser Phe Thr
                405                 410                 415

Leu Gly Cys Gly Phe Trp Gly Gly Asn Ser Val Ser Glu Asn Val Gly
                420                 425                 430

Pro Lys His Leu Leu Asn Ile Lys Thr Val Ala Glu Arg Arg Glu Asn
                435                 440                 445

Met Leu Trp Phe Arg Val Pro His Lys Val Tyr Phe Lys Phe Gly Cys
450                 455                 460

Leu Gln Phe Ala Leu Lys Asp Leu Lys Asp Leu Lys Lys Arg Ala
465                 470                 475                 480

Phe Ile Val Thr Asp Ser Asp Pro Tyr Asn Leu Asn Tyr Val Asp Ser
                485                 490                 495

Ile Ile Lys Ile Leu Glu His Leu Asp Ile Asp Phe Lys Val Phe Asn
                500                 505                 510

Lys Val Gly Arg Glu Ala Asp Leu Lys Thr Ile Lys Lys Ala Thr Glu
                515                 520                 525

Glu Met Ser Ser Phe Met Pro Asp Thr Ile Ile Ala Leu Gly Gly Thr
530                 535                 540

Pro Glu Met Ser Ser Ala Lys Leu Met Trp Val Leu Tyr Glu His Pro
545                 550                 555                 560

Glu Val Lys Phe Glu Asp Leu Ala Ile Lys Phe Met Asp Ile Arg Lys
                565                 570                 575

Arg Ile Tyr Thr Phe Pro Lys Leu Gly Lys Lys Ala Met Leu Val Ala
                580                 585                 590

Ile Thr Thr Ser Ala Gly Ser Gly Ser Glu Val Thr Pro Phe Ala Leu
                595                 600                 605

Val Thr Asp Asn Asn Thr Gly Asn Lys Tyr Met Leu Ala Asp Tyr Glu
                610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
                645                 650                 655

```
Ile Glu Ala Tyr Thr Ser Val Tyr Ala Ser Glu Tyr Thr Asn Gly Leu
            660                 665                 670

Ala Leu Glu Ala Ile Arg Leu Ile Phe Lys Tyr Leu Pro Glu Ala Tyr
        675                 680                 685

Lys Asn Gly Arg Thr Asn Glu Lys Ala Arg Glu Lys Met Ala His Ala
    690                 695                 700

Ser Thr Met Ala Gly Met Ala Ser Ala Asn Ala Phe Leu Gly Leu Cys
705                 710                 715                 720

His Ser Met Ala Ile Lys Leu Ser Ser Glu His Asn Ile Pro Ser Gly
            725                 730                 735

Ile Ala Asn Ala Leu Leu Ile Glu Glu Val Ile Lys Phe Asn Ala Val
            740                 745                 750

Asp Asn Pro Val Lys Gln Ala Pro Cys Pro Gln Tyr Lys Tyr Pro Asn
        755                 760                 765

Thr Ile Phe Arg Tyr Ala Arg Ile Ala Asp Tyr Ile Lys Leu Gly Gly
    770                 775                 780

Asn Thr Asp Glu Glu Lys Val Asp Leu Leu Ile Asn Lys Ile His Glu
785                 790                 795                 800

Leu Lys Lys Ala Leu Asn Ile Pro Thr Ser Ile Lys Asp Ala Gly Val
            805                 810                 815

Leu Glu Glu Asn Phe Tyr Ser Ser Leu Asp Arg Ile Ser Glu Leu Ala
            820                 825                 830

Leu Asp Asp Gln Cys Thr Gly Ala Asn Pro Arg Phe Pro Leu Thr Ser
        835                 840                 845

Glu Ile Lys Glu Met Tyr Ile Asn Cys Phe Lys Lys Gln Pro
    850                 855                 860

<210> SEQ ID NO 19
<211> LENGTH: 1173
<212> TYPE: DNA
<213> ORGANISM: Clostridium acetobutylicum

<400> SEQUENCE: 19
gtggttgatt tcgaatattc aataccaact agaattttt tcggtaaaga taagataaat      60
gtacttggaa gagagcttaa aaaatatggt tctaaagtgc ttatagttta tggtggagga     120
agtataaaga gaaatggaat atatgataaa gctgtaagta tacttgaaaa aaacagtatt     180
aaattttatg aacttgcagg agtagagcca atccaagag taactacagt tgaaaaagga      240
gttaaaatat gtagagaaaa tggagttgaa gtagtactag ctataggtgg aggaagtgca     300
atagattgcg caaaggttat agcagcagca tgtgaatatg atggaaatcc atgggatatt     360
gtgttagatg gctcaaaaat aaaaagggtg cttcctatag ctagtatatt aaccattgct     420
gcaacaggat cagaaatgga tacgtgggca gtaataaata tatggatac aaacgaaaaa     480 ctaattgcgg cacatccaga tatggctcct aagttttcta tattagatcc aacgtatacg     540
tataccgtac ctaccaatca aacagcagca ggaacagctg atattatgag tcatatattt     600
gaggtgtatt ttagtaatac aaaaacagca tatttgcagg atagaatggc agaagcgtta     660
ttaagaactt gtattaaata tggaggaata gctcttgaga agccggatga ttatgaggca     720
agagccaatc taatgtgggc ttcaagtctt gcgataaatg acttttaac atatggtaaa     780 gacactaatt ggagtgtaca cttaatggaa catgaattaa gtgcttatta cgacataaca     840
cacggcgtag gcttgcaat tttaacacct aattggatgg agtatatttt aaataatgat     900
acagtgtaca agtttgttga atatggtgta aatgtttggg aatagacaa agaaaaaat      960
```

-continued

```
cactatgaca tagcacatca agcaatacaa aaaacaagag attactttgt aaatgtacta    1020
ggtttaccat ctagactgag agatgttgga attgaagaag aaaaattgga cataatggca    1080
aaggaatcag taaagcttac aggaggaacc ataggaaacc taagaccagt aaacgcctcc    1140
gaagtcctac aaatattcaa aaaatctgtg taa                                 1173
```

<210> SEQ ID NO 20
<211> LENGTH: 390
<212> TYPE: PRT
<213> ORGANISM: Clostridium acetobutylicum

<400> SEQUENCE: 20

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335
```

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385             390

<210> SEQ ID NO 21
<211> LENGTH: 657
<212> TYPE: DNA
<213> ORGANISM: Clostridium acetobutylicum

<400> SEQUENCE: 21
atgaactcta aataattag atttgaaaat ttaaggtcat tctttaaaga tgggatgaca      60
attatgattg gaggtttttt aaactgtggc actccaacca aattaattga ttttttagtt    120
aatttaaata taaagaattt aacgattata agtaatgata catgttatcc taatacaggt    180
attggtaagt taatatcaaa taatcaagta aaaaagctta ttgcttcata taggcagc      240 aacccagata ctggcaaaaa acttttaat aatgaacttg aagtagagct ctctccccaa     300
ggaactctag tggaaagaat acgtgcaggc ggatctggct taggtggtgt actaactaaa    360
acaggtttag aactttgat tgaaaaagga agaaaaaaa tatctataaa tggaacggaa      420
tatttgttag agctacctct tacagccgat gtagcattaa ttaaaggtag tattgtagat    480
gaggccggaa acaccttcta taaggtact actaaaaact ttaatcccta tatggcaatg    540
gcagctaaaa ccgtaatagt tgaagctgaa aatttagtta gctgtgaaaa actagaaaag    600
gaaaaagcaa tgaccccggg agttcttata aattatatag taaaggagcc tgcataa      657

<210> SEQ ID NO 22
<211> LENGTH: 218
<212> TYPE: PRT
<213> ORGANISM: Clostridium acetobutylicum

<400> SEQUENCE: 22

Met Asn Ser Lys Ile Ile Arg Phe Glu Asn Leu Arg Ser Phe Phe Lys
1               5                   10                  15

Asp Gly Met Thr Ile Met Ile Gly Gly Phe Leu Asn Cys Gly Thr Pro
            20                  25                  30

Thr Lys Leu Ile Asp Phe Leu Val Asn Leu Asn Ile Lys Asn Leu Thr
        35                  40                  45

Ile Ile Ser Asn Asp Thr Cys Tyr Pro Asn Thr Gly Ile Gly Lys Leu
    50                  55                  60

Ile Ser Asn Asn Gln Val Lys Lys Leu Ile Ala Ser Tyr Ile Gly Ser
65                  70                  75                  80

Asn Pro Asp Thr Gly Lys Lys Leu Phe Asn Asn Glu Leu Glu Val Glu
                85                  90                  95

Leu Ser Pro Gln Gly Thr Leu Val Glu Arg Ile Arg Ala Gly Gly Ser
            100                 105                 110

Gly Leu Gly Gly Val Leu Thr Lys Thr Gly Leu Gly Thr Leu Ile Glu
        115                 120                 125

Lys Gly Lys Lys Lys Ile Ser Ile Asn Gly Thr Glu Tyr Leu Leu Glu
    130                 135                 140

Leu Pro Leu Thr Ala Asp Val Ala Leu Ile Lys Gly Ser Ile Val Asp
145                 150                 155                 160

```
Glu Ala Gly Asn Thr Phe Tyr Lys Gly Thr Thr Lys Asn Phe Asn Pro
                165                 170                 175

Tyr Met Ala Met Ala Ala Lys Thr Val Ile Val Glu Ala Glu Asn Leu
            180                 185                 190

Val Ser Cys Glu Lys Leu Glu Lys Glu Lys Ala Met Thr Pro Gly Val
        195                 200                 205

Leu Ile Asn Tyr Ile Val Lys Glu Pro Ala
    210                 215

<210> SEQ ID NO 23
<211> LENGTH: 666
<212> TYPE: DNA
<213> ORGANISM: Clostridium acetobutylicum

<400> SEQUENCE: 23
atgattaatg ataaaaacct agcgaaagaa ataatagcca aaagagttgc aagagaatta      60
aaaaatggtc aacttgtaaa cttaggtgta ggtcttccta ccatggttgc agattatata     120
ccaaaaaatt tcaaaattac tttccaatca gaaacggaa  tagttggaat gggcgctagt     180
cctaaaataa atgaggcaga taagatgta  gtaaatgcag gaggagacta tacaacagta     240
cttcctgacg gcacattttt cgatagctca gtttcgtttt cactaatccg tggtggtcac     300
gtagatgtta ctgttttagg ggctctccag gtagatgaaa agggtaatat agccaattgg     360
attgttcctg gaaaaatgct ctctggtatg ggtggagcta tggatttagt aaatggagct     420
aagaaagtaa taattgcaat gagacataca aataaaggtc aacctaaaat tttaaaaaaa     480
tgtacacttc ccctcacggc aaagtctcaa gcaaatctaa ttgtaacaga acttggagta     540
attgaggtta ttaatgatgg tttacttctc actgaaatta ataaaaacac aaccattgat     600
gaaataaggt ctttaactgc tgcagattta ctcatatcca atgaacttag acccatggct     660
gtttag                                                               666

<210> SEQ ID NO 24
<211> LENGTH: 221
<212> TYPE: PRT
<213> ORGANISM: Clostridium acetobutylicum

<400> SEQUENCE: 24

Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Glu Asn Gly Ile Val Gly Met Gly Ala Ser Pro Lys Ile Asn
    50                  55                  60

Glu Ala Asp Lys Asp Val Val Asn Ala Gly Gly Asp Tyr Thr Thr Val
65                  70                  75                  80

Leu Pro Asp Gly Thr Phe Phe Asp Ser Ser Val Ser Phe Ser Leu Ile
                85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
    130                 135                 140
```

```
Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
            165                 170                 175

Glu Leu Gly Val Ile Glu Val Ile Asn Asp Gly Leu Leu Leu Thr Glu
        180                 185                 190

Ile Asn Lys Asn Thr Thr Ile Asp Glu Ile Arg Ser Leu Thr Ala Ala
        195                 200                 205

Asp Leu Leu Ile Ser Asn Glu Leu Arg Pro Met Ala Val
    210                 215                 220

<210> SEQ ID NO 25
<211> LENGTH: 1824
<212> TYPE: DNA
<213> ORGANISM: Clostridium ljungdahlii

<400> SEQUENCE: 25
atgtacggat ataagggtaa ggtattaaga attaatctaa gtagtaaaac ttatatagtg      60
gaagaattga aaattgacaa agctaaaaaa tttataggtg caagagggtt aggcgtaaaa     120
accttatttg acgaagtaga tccaaaggta gatccattat cacctgataa caaatttatt     180
atagcagcgg gaccacttac aggtgcacct gttccaacaa gcggaagatt catggtagtt     240
actaaatcac ctttaacagg aactattgct attgcaaatt caggtggaaa atggggagca     300
gaattcaaag cagctggata cgatatgata atcgttgaag gtaaatctga taagaagtt      360 tatgtaaata tagtagatga taagtgaa tttaggatg cttctcatgt ttggggaaaa       420
ctaacagaag aaactacaaa atgcttcaa caggaaacag attcgagagc taaggtttta     480
tgcataggac cagctgggga aaagttatca cttatggcag cagttatgaa tgatgttgat     540
agaacagcag gacgtggtgg tgttggagct gttatgggtt caagaacttt aaaagctatt     600
gtagttaaag aagcggaaa agtaaaatta tttgatgaac aaaaagtgaa ggaagtagca     660
cttgagaaaa caaatatttt aagaaagat ccagtagctg gtggaggact tccaacatac     720
ggaacagctg tacttgttaa tattataat gaaaatggtg tacatccagt aaagaatttt     780 caaaatctt atacagatca agcagataag atcagtggag aaacttaac taagattgc       840 ttagttagaa aaaatccttg ctataggtgt ccaattgcct gtggaagatg ggtaaaactt     900
gatgatggaa ctgaatgtgg aggaccagaa tatgaaacat tatggtcatt tggatctgat     960
tgtgatgtat acgatataaa tgctgtaaat acagcaaata tgttgtgtaa tgaatatgga    1020
ttagatacca ttacagcagg atgtactatt gcagcagcta tggaactttta tcaaagaggt    1080 tatattaagg atgaagaaat agcagcagat ggattgtcac ttaattgggg agatgctaag    1140
tccatggttg aatgggtaaa gaaaatggga cttagagaag gatttggaga caagatggca    1200
gatggttcat acagactttg tgactcatac ggtgtacctg agtattcaat gactgtaaaa    1260
aaacaggaac ttccagcata tgacccaaga ggaatacagg acatggtat tacttatgct     1320 gttaacaata gggaggaatg tcacattaag ggatatatgg taagtcctga aatacttggc    1380
tatccagaaa aacttgatag acttgcagtg aaggaaaaag caggatatgc tagagtattc    1440
catgatttaa cagctgttat agattcactt ggattatgta ttttttacaac atttggtctt    1500 ggtgcacagg attatgttga tatgtataat gcagtagttg gtggagaatt acatgatgta    1560
aattctttaa tgttagctgg agatagaata tggacttag aaaaaatatt taacttaaag      1620
gcaggcatag atagttcaca ggatactctt ccaaagagat tgcttgaaga acaaattcca    1680
```

-continued

```
gaaggaccat caaaaggaga agttcataag ttagatgtac tactacctga atattattca   1740
gtacgtggat gggataaaaa tggtattcct acagaggaaa cgttaaagaa attaggatta   1800
gatgaatacg taggtaagct ttag                                          1824
```

<210> SEQ ID NO 26
<211> LENGTH: 607
<212> TYPE: PRT
<213> ORGANISM: Clostridium ljungdahlii

<400> SEQUENCE: 26

```
Met Tyr Gly Tyr Lys Gly Lys Val Leu Arg Ile Asn Leu Ser Ser Lys
 1               5                  10                  15

Thr Tyr Ile Val Glu Glu Leu Lys Ile Asp Lys Ala Lys Lys Phe Ile
            20                  25                  30

Gly Ala Arg Gly Leu Gly Val Lys Thr Leu Phe Asp Glu Val Asp Pro
        35                  40                  45

Lys Val Asp Pro Leu Ser Pro Asp Asn Lys Phe Ile Ile Ala Ala Gly
    50                  55                  60

Pro Leu Thr Gly Ala Pro Val Pro Thr Ser Gly Arg Phe Met Val Val
65                  70                  75                  80

Thr Lys Ser Pro Leu Thr Gly Thr Ile Ala Ile Ala Asn Ser Gly Gly
                85                  90                  95

Lys Trp Gly Ala Glu Phe Lys Ala Ala Gly Tyr Asp Met Ile Ile Val
            100                 105                 110

Glu Gly Lys Ser Asp Lys Glu Val Tyr Val Asn Ile Val Asp Asp Lys
        115                 120                 125

Val Glu Phe Arg Asp Ala Ser His Val Trp Gly Lys Leu Thr Glu Glu
    130                 135                 140

Thr Thr Lys Met Leu Gln Gln Glu Thr Asp Ser Arg Ala Lys Val Leu
145                 150                 155                 160

Cys Ile Gly Pro Ala Gly Glu Lys Leu Ser Leu Met Ala Ala Val Met
                165                 170                 175

Asn Asp Val Asp Arg Thr Ala Gly Arg Gly Gly Val Gly Ala Val Met
            180                 185                 190

Gly Ser Lys Asn Leu Lys Ala Ile Val Val Lys Gly Ser Gly Lys Val
        195                 200                 205

Lys Leu Phe Asp Glu Gln Lys Val Lys Glu Val Ala Leu Glu Lys Thr
    210                 215                 220

Asn Ile Leu Arg Lys Asp Pro Val Ala Gly Gly Leu Pro Thr Tyr
225                 230                 235                 240

Gly Thr Ala Val Leu Val Asn Ile Ile Asn Glu Asn Gly Val His Pro
                245                 250                 255

Val Lys Asn Phe Gln Lys Ser Tyr Thr Asp Gln Ala Asp Lys Ile Ser
            260                 265                 270

Gly Glu Thr Leu Thr Lys Asp Cys Leu Val Arg Lys Asn Pro Cys Tyr
        275                 280                 285

Arg Cys Pro Ile Ala Cys Gly Arg Trp Val Lys Leu Asp Asp Gly Thr
    290                 295                 300

Glu Cys Gly Gly Pro Glu Tyr Glu Thr Leu Trp Ser Phe Gly Ser Asp
305                 310                 315                 320

Cys Asp Val Tyr Asp Ile Asn Ala Val Asn Thr Ala Asn Met Leu Cys
                325                 330                 335

Asn Glu Tyr Gly Leu Asp Thr Ile Thr Ala Gly Cys Thr Ile Ala Ala
```

```
           340                 345                 350
Ala Met Glu Leu Tyr Gln Arg Gly Tyr Ile Lys Asp Glu Glu Ile Ala
        355                 360                 365

Ala Asp Gly Leu Ser Leu Asn Trp Gly Asp Ala Lys Ser Met Val Glu
    370                 375                 380

Trp Val Lys Lys Met Gly Leu Arg Glu Gly Phe Gly Asp Lys Met Ala
385                 390                 395                 400

Asp Gly Ser Tyr Arg Leu Cys Asp Ser Tyr Gly Val Pro Glu Tyr Ser
                405                 410                 415

Met Thr Val Lys Lys Gln Glu Leu Pro Ala Tyr Asp Pro Arg Gly Ile
            420                 425                 430

Gln Gly His Gly Ile Thr Tyr Ala Val Asn Asn Arg Gly Gly Cys His
        435                 440                 445

Ile Lys Gly Tyr Met Val Ser Pro Glu Ile Leu Gly Tyr Pro Glu Lys
    450                 455                 460

Leu Asp Arg Leu Ala Val Glu Gly Lys Ala Gly Tyr Ala Arg Val Phe
465                 470                 475                 480

His Asp Leu Thr Ala Val Ile Asp Ser Leu Gly Leu Cys Ile Phe Thr
                485                 490                 495

Thr Phe Gly Leu Gly Ala Gln Asp Tyr Val Asp Met Tyr Asn Ala Val
            500                 505                 510

Val Gly Gly Glu Leu His Asp Val Asn Ser Leu Met Leu Ala Gly Asp
        515                 520                 525

Arg Ile Trp Thr Leu Glu Lys Ile Phe Asn Leu Lys Ala Gly Ile Asp
    530                 535                 540

Ser Ser Gln Asp Thr Leu Pro Lys Arg Leu Leu Glu Glu Gln Ile Pro
545                 550                 555                 560

Glu Gly Pro Ser Lys Gly Glu Val His Lys Leu Asp Val Leu Leu Pro
                565                 570                 575

Glu Tyr Tyr Ser Val Arg Gly Trp Asp Lys Asn Gly Ile Pro Thr Glu
            580                 585                 590

Glu Thr Leu Lys Lys Leu Gly Leu Asp Glu Tyr Val Gly Lys Leu
        595                 600                 605

<210> SEQ ID NO 27
<211> LENGTH: 735
<212> TYPE: DNA
<213> ORGANISM: Clostridium acetobutylicum

<400> SEQUENCE: 27
atgttaaagg atgaagtaat taaacaaatt agcacgccat taacttcgcc tgcatttcct      60
agaggaccct ataaatttca taatcgtgag tattttaaca ttgtatatcg tacagatatg     120
gatgcacttc gtaaagttgt gccagagcct ttagaaattg atgagccctt agtcaggttt     180
gaaattatgg caatgcatga tacgagtgga cttggttgtt atacagaaag cggacaggct     240
attcccgtaa gctttaatgg agttaaggga gattatcttc atatgatgta tttagataat     300
gagcctgcaa ttgcagtagg aagggaatta agtgcatatc ctaaaaagct cgggtatcca     360
aagcttttgt ggattcaga tactttagta ggaactttag actatggaaa acttagagtt     420
gcgacagcta caatggggta caaacataaa gccttagatg ctaatgaagc aaaggatcaa     480
atttgtcgcc taattatat gttgaaaata tacccaatt atgatggaag ccctagaata     540
tgtgagctta taaatgcgaa aatcacagat gttaccgtac atgaagcttg gacaggacca     600
actcgactgc agttatttga tcacgctatg gcgccactta atgatttgcc agtaaaagag     660
```

```
attgtttcta gctctcacat tcttgcagat ataatattgc ctagagctga agttatatat    720
gattatctta agtaa                                                    735

<210> SEQ ID NO 28
<211> LENGTH: 244
<212> TYPE: PRT
<213> ORGANISM: Clostridium acetobutylicum

<400> SEQUENCE: 28

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
        35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 29
<211> LENGTH: 1140
<212> TYPE: DNA
<213> ORGANISM: Clostridium acetobutylicum

<400> SEQUENCE: 29
atggatttta atttaacaag agaacaagaa ttagtaagac agatggttag agaatttgct    60
gaaaatgaag ttaaacctat agcagcagaa attgatgaaa cagaaagatt tccaatggaa   120
aatgtaaaga aaatgggtca gtatggtatg atgggaattc cattttcaaa agagtatggt   180
ggcgcaggtg agatgtgtat atcttatata atcgccgttg aggaattatc aaaggtttgc   240
ggtactacag gagttattct ttcagcacat acatcacttt gtgcttcatt aataaatgaa   300
catggtacag aagaacaaaa acaaaaatat ttagtacctt tagctaaagg tgaaaaaata   360
```

-continued

```
ggtgcttatg gattgactga gccaaatgca ggaacagatt ctggagcaca acaaacagta    420
gctgtacttg aaggagatca ttatgtaatt aatggttcaa aaatattcat aactaatgga    480
ggagttgcag atactttttgt tatatttgca atgactgaca gaactaaagg aacaaaaggt    540
atatcagcat ttataataga aaaaggcttc aaaggtttct ctattggtaa agttgaacaa    600
aagcttggaa taagagcttc atcaacaact gaacttgtat ttgaagatat gatagtacca    660
gtagaaaaca tgattggtaa agaaggaaaa ggcttcccta tagcaatgaa aactcttgat    720
ggaggaagaa ttggtatagc agctcaagct ttaggtatag ctgaaggtgc tttcaacgaa    780
gcaagagctt acatgaagga gagaaaacaa tttggaagaa gccttgacaa attccaaggt    840
cttgcatgga tgatggcaga tatggatgta gctatagaat cagctagata tttagtatat    900
aaagcagcat atcttaaaca agcaggactt ccatacacag ttgatgctgc aagagctaag    960
cttcatgctg caaatgtagc aatggatgta acaactaagg cagtacaatt atttggtgga    1020
tacggatata caaaagatta tccagttgaa agaatgatga gagatgctaa gataactgaa    1080
atatatgaag gaacttcaga agttcagaaa ttagttattt caggaaaaat ttttagataa    1140
```

<210> SEQ ID NO 30
<211> LENGTH: 379
<212> TYPE: PRT
<213> ORGANISM: Clostridium acetobutylicum

<400> SEQUENCE: 30

```
Met Asp Phe Asn Leu Thr Arg Glu Gln Glu Leu Val Arg Gln Met Val
1               5                   10                  15

Arg Glu Phe Ala Glu Asn Glu Val Lys Pro Ile Ala Ala Glu Ile Asp
                20                  25                  30

Glu Thr Glu Arg Phe Pro Met Glu Asn Val Lys Lys Met Gly Gln Tyr
            35                  40                  45

Gly Met Met Gly Ile Pro Phe Ser Lys Glu Tyr Gly Gly Ala Gly Gly
        50                  55                  60

Asp Val Leu Ser Tyr Ile Ile Ala Val Glu Glu Leu Ser Lys Val Cys
65                  70                  75                  80

Gly Thr Thr Gly Val Ile Leu Ser Ala His Thr Ser Leu Cys Ala Ser
                85                  90                  95

Leu Ile Asn Glu His Gly Thr Glu Glu Gln Lys Gln Lys Tyr Leu Val
            100                 105                 110

Pro Leu Ala Lys Gly Glu Lys Ile Gly Ala Tyr Gly Leu Thr Glu Pro
        115                 120                 125

Asn Ala Gly Thr Asp Ser Gly Ala Gln Gln Thr Val Ala Val Leu Glu
    130                 135                 140

Gly Asp His Tyr Val Ile Asn Gly Ser Lys Ile Phe Ile Thr Asn Gly
145                 150                 155                 160

Gly Val Ala Asp Thr Phe Val Ile Phe Ala Met Thr Asp Arg Thr Lys
                165                 170                 175

Gly Thr Lys Gly Ile Ser Ala Phe Ile Ile Glu Lys Gly Phe Lys Gly
            180                 185                 190

Phe Ser Ile Gly Lys Val Glu Gln Lys Leu Gly Ile Arg Ala Ser Ser
        195                 200                 205

Thr Thr Glu Leu Val Phe Glu Asp Met Ile Val Pro Val Glu Asn Met
    210                 215                 220

Ile Gly Lys Glu Gly Lys Gly Phe Pro Ile Ala Met Lys Thr Leu Asp
225                 230                 235                 240
```

```
Gly Gly Arg Ile Gly Ile Ala Ala Gln Ala Leu Gly Ile Ala Glu Gly
                245                 250                 255
Ala Phe Asn Glu Ala Arg Ala Tyr Met Lys Glu Arg Lys Gln Phe Gly
            260                 265                 270
Arg Ser Leu Asp Lys Phe Gln Gly Leu Ala Trp Met Met Ala Asp Met
        275                 280                 285
Asp Val Ala Ile Glu Ser Ala Arg Tyr Leu Val Tyr Lys Ala Ala Tyr
    290                 295                 300
Leu Lys Gln Ala Gly Leu Pro Tyr Thr Val Asp Ala Ala Arg Ala Lys
305                 310                 315                 320
Leu His Ala Ala Asn Val Ala Met Asp Val Thr Thr Lys Ala Val Gln
                325                 330                 335
Leu Phe Gly Gly Tyr Gly Tyr Thr Lys Asp Tyr Pro Val Glu Arg Met
            340                 345                 350
Met Arg Asp Ala Lys Ile Thr Glu Ile Tyr Glu Gly Thr Ser Glu Val
        355                 360                 365
Gln Lys Leu Val Ile Ser Gly Lys Ile Phe Arg
    370                 375

<210> SEQ ID NO 31
<211> LENGTH: 1197
<212> TYPE: DNA
<213> ORGANISM: Euglena gracilis

<400> SEQUENCE: 31
atgatagtaa aagcaaagtt tgtaaaagga tttatcagag atgtacatcc ttatggttgc      60
agaagggaag tactaaatca aatagattat tgtaagaagg ctattgggtt taggggacca     120
aagaaggttt taattgttgg agcctcatct gggtttggtc ttgctactag aatttcagtt     180
gcatttggag gtccagaagc tcacacaatt ggagtatcct atgaaacagg agctacagat     240
agaagaatag aacagcggga tggtataat aacatatttt ttaaagaatt tgctaaaaaa      300
aaaggattag ttgcaaaaaa cttcattgag gatgcctttt ctaatgaaac caagataaa      360
gttattaagt atataaagga tgaatttggt aaaatagatt tatttgttta gttttagct      420
gcgcctagga gaaaggacta taaaactgga atgtttata cttcaagaat aaaaacaatt      480
ttaggagatt tgagggacc gactattgat gttgaaagag acgagattac tttaaaaaag     540
gttagtagtg ctagcattga agaaattgaa gaaactagaa aggtaatggg tggagaggat     600
tggcaagagt ggtgtgaaga gctgctttat gaagattgtt tttcggataa agcaactacc      660
atagcatact cgtatatagg atccccaaga acctacaaga tatatagaga aggtactata      720
ggaatagcta aaaaggatct tgaagataag gctaagctta taaatgaaaa acttaacaga      780
gttataggtg gtagagcctt tgtgtctgtg aataaagcat tagttacaaa agcaagtgca      840
tatattccaa cttttcctct ttatgcagct attttatata aggtcatgaa agaaaaaaat      900
attcatgaaa attgtattat gcaaattgag gaatgttttt ctgaaaaaat atattcaaat      960
gaaaaaatac aatttgatga caagggaaga ttaaggatgg acgatttaga gcttagaaaa     1020
gacgttcaag acgaagttga tagaatatgg agtaatatta ctcctgaaaa ttttaaggaa     1080
ttatctgatt ataagggata caaaaaagaa ttcatgaact aaacggtttt tgatctagat     1140
ggggttgatt atagtaaaga cctggatata gaattattaa gaaaattaga accttaa        1197

<210> SEQ ID NO 32
<211> LENGTH: 398
```

<212> TYPE: PRT
<213> ORGANISM: Euglena gracilis

<400> SEQUENCE: 32

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395
```

<210> SEQ ID NO 33
<211> LENGTH: 1056
<212> TYPE: DNA
<213> ORGANISM: Clostridium beijerinckii

<400> SEQUENCE: 33

```
atgaaaggtt ttgcaatgct aggtattaat aagttaggat ggatcgaaaa agaaaggcca      60
gttgcgggtt catatgatgc tattgtacgc ccattagcag tatctccgtg tacatcagat     120
atacatactg tttttgaggg agctcttgga gataggaaga atatgatttt agggcatgaa     180
gctgtaggta agttgttga agtaggaagt gaagtgaagg atttaaacc tggtgacaga       240
gttatagttc cttgtacaac tccagattgg agatctttgg aagttcaagc tggttttcaa    300
cagcactcaa acggtatgct cgcaggatgg aaatttcaa atttcaagga tggagttttt    360
ggtgaatatt tcatgtaaa tgatgcggat atgaatcttg cgattctacc taaagacatg     420
ccattagaaa atgctgttat gataacagat atgatgacta ctggatttca tggagcagaa     480
cttgcagata ttcaaatggg ttcaagtgtt gtggtaattg cattggagc tgttggctta     540
atgggaatag caggtgctaa attacgtgga gcaggtagaa taattggagt ggggagcagg     600
ccgatttgtg ttgaggctgc aaaatttat ggagcaacag atattctaaa ttataaaaat     660
ggtcatatag ttgatcaagt tatgaaatta acgaatggaa aaggcgttga ccgcgtaatt     720
atggcaggcg gtggttctga acattatcc caagcagtat ctatggttaa ccaggagga     780
ataatttcta atataaatta tcatggaagt ggagatgctt tactaatacc acgtgtagaa     840
tggggatgtg gaatggctca aagactata aaaggaggtc tttgtcctgg gggacgttg     900
agagcagaaa tgttaagaga tatggtagta tataatcgtg ttgatctaag taaattagtt     960
acacatgtat atcatggatt tgatcacata gaagaagcac tgttattaat gaaagacaag    1020
ccaaaagact aattaaagc agtagttata ttataa                                1056
```

<210> SEQ ID NO 34
<211> LENGTH: 351
<212> TYPE: PRT
<213> ORGANISM: Clostridium beijerinckii

<400> SEQUENCE: 34

```
Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140
```

```
Ala Val Met Ile Thr Asp Met Met Thr Thr Gly Phe His Gly Ala Glu
145                 150                 155                 160

Leu Ala Asp Ile Gln Met Gly Ser Ser Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
                260                 265                 270

Ala Leu Leu Ile Pro Arg Val Glu Trp Gly Cys Gly Met Ala His Lys
            275                 280                 285

Thr Ile Lys Gly Gly Leu Cys Pro Gly Gly Arg Leu Arg Ala Glu Met
        290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
                340                 345                 350

<210> SEQ ID NO 35
<211> LENGTH: 1998
<212> TYPE: DNA
<213> ORGANISM: Clostridium acetobutylicum

<400> SEQUENCE: 35
atgggtaata agatatttgc cgtacttcaa aaaatcggta atctttaat gcttccagta      60 tctgttctac cggcggctgg aattctattg agacttggac agccagattt gcttaatatg    120
ccttatgttc aagcagcagg aaatgctatt tttaataatt tacctttaat ttttgcggtt    180
ggagttgcta taggtttttc aggcggagaa ggtgttgcag cacttgcagc tgtaattgga    240
gaactaatac ttgaggcggt tgaaaaaaca gcaggtgata cggcagcagc agctttagca    300
aaaacagcgg cagcttcaca tcatatgacg cttgcagcat tcaaaaaac tcaagaatac    360 agtaacattg taactaaaac aactattagt atgggtgttt ttggcggtat aataatcggt    420
cttacagcag ctatttttata taataagttc catgatataa agatgcctca agttttgggt    480
ttctttggtg gaaaacgttt cgttccaatt ataacttcaa tttcagctct tattattgca    540
actataggag taaatatttg gttgccaata caagctggaa taaattcact agcagcattt    600
gcaactacat caccaattgg acctgcaatg tatgctggag gaaaaagact tttaattcca    660
ctaggacttc atcacattta ttatccattg ttcttatatc aatttggtca ctttgtttca    720
aatggagtta cttatgtagg agatacagca agatacttcc atggggatcc tactgccgga    780
aacttcatgg cagcagagta tccaatacta atgtttggtc ttccaggagc tgctctagct    840
atgattgcag ctgctaaaaa agaaaagaga aagaaatgg ctggaatgat gatttcagca    900
gcatttgtag catttgtaac aggtattaca gagccaattg aattctcatt catatttgtt    960
```

```
gctccagtat tatttgtgtt ccacgtactt gctgcattcg catctggtct tattacaagt    1020
tatttacaca taagattagg gtatactttc tcagcatcct tcatagatta tgttttagga    1080
ttcaaatatg caggtcatcc attacttata tggcttgtag gtatagggtt ctttgtattg    1140
tactttgttg tattctactt cacaattaaa gcaatgaaca ttaagacacc aggtagagaa    1200
gatgatgatg cagaaggtgt taagaagata aatgtaaaag gaaaagctaa ggcagctaag    1260
gtgcttgaag ctataggcgg aaaagataat ataaaagtac ttgatgcatg tataacaaga    1320
ttaagactta acttaaatga tccttctttg gttgataaag ctacacttaa agctcttgga    1380
gcagctggag taatgacagc agaagatagt gttcaagtag ttttggaac tgaagctgaa    1440 agaataaaag atgacataaa agcaattata caaaatggtg gatatgttga agatgattca    1500
gataaggaag aagaagttca agaggataag caaatttcta aaggtgcaca cgaactttta    1560
agtccagctg atggagaagt agttggtatt gagagtgttc cggatagtac atttgctgaa    1620
aaaatgcttg gagacggttt tgcagtaata ccttcaggaa atgaagtaca ctcaccagct    1680
gatggagaag tatcagtttt attcccaact aagcatgcat ttgcaataac aacagaaggc    1740
ggacttgaac ttttaataca tgttggaatt gatactgtag cattaaatgg tgaaggtttc    1800
acagcacatg taaacaagg agataaagtt aaaaaggag atttgatttt aactttagat    1860
actgagttta taaagagcaa aggtaaaaac cttataactc cagtgattgt aactaacatg    1920
gatgttgtag gaaatataga tgttaaatta ggaaacgtta aaaattccga gaaagctgcg    1980
gatgttaccg taaaataa                                                 1998

<210> SEQ ID NO 36
<211> LENGTH: 665
<212> TYPE: PRT
<213> ORGANISM: Clostridium acetobutylicum

<400> SEQUENCE: 36

Met Gly Asn Lys Ile Phe Ala Val Leu Gln Lys Ile Gly Lys Ser Leu
1               5                   10                  15

Met Leu Pro Val Ser Val Leu Pro Ala Ala Gly Ile Leu Leu Arg Leu
                20                  25                  30

Gly Gln Pro Asp Leu Leu Asn Met Pro Tyr Val Gln Ala Ala Gly Asn
        35                  40                  45

Ala Ile Phe Asn Asn Leu Pro Leu Ile Phe Ala Val Gly Val Ala Ile
    50                  55                  60

Gly Phe Ser Gly Gly Glu Gly Val Ala Ala Leu Ala Ala Val Ile Gly
65                  70                  75                  80

Glu Leu Ile Leu Glu Ala Val Glu Lys Thr Ala Gly Asp Thr Ala Ala
                85                  90                  95

Ala Ala Leu Ala Lys Thr Ala Ala Ala Ser His His Met Thr Leu Ala
            100                 105                 110

Ala Phe Gln Lys Thr Gln Glu Tyr Ser Asn Ile Val Thr Lys Thr Thr
        115                 120                 125

Ile Ser Met Gly Val Phe Gly Gly Ile Ile Gly Leu Thr Ala Ala
    130                 135                 140

Ile Leu Tyr Asn Lys Phe His Asp Ile Lys Met Pro Gln Val Leu Gly
145                 150                 155                 160

Phe Phe Gly Gly Lys Arg Phe Val Pro Ile Ile Thr Ser Ile Ser Ala
                165                 170                 175

Leu Ile Ile Ala Thr Ile Gly Val Asn Ile Trp Leu Pro Ile Gln Ala
```

```
            180                 185                 190
Gly Ile Asn Ser Leu Ala Ala Phe Ala Thr Thr Ser Pro Ile Gly Pro
            195                 200                 205
Ala Met Tyr Ala Gly Lys Arg Leu Leu Ile Pro Leu Gly Leu His
            210                 215                 220
His Ile Tyr Tyr Pro Leu Phe Leu Tyr Gln Phe Gly His Phe Val Ser
225                 230                 235                 240
Asn Gly Val Thr Tyr Val Gly Asp Thr Ala Arg Tyr Phe His Gly Asp
                245                 250                 255
Pro Thr Ala Gly Asn Phe Met Ala Ala Glu Tyr Pro Ile Leu Met Phe
            260                 265                 270
Gly Leu Pro Gly Ala Ala Leu Ala Met Ile Ala Ala Lys Lys Glu
            275                 280                 285
Lys Arg Lys Glu Met Ala Gly Met Met Ile Ser Ala Ala Phe Val Ala
            290                 295                 300
Phe Val Thr Gly Ile Thr Glu Pro Ile Glu Phe Ser Phe Ile Phe Val
305                 310                 315                 320
Ala Pro Val Leu Phe Val Phe His Val Leu Ala Ala Phe Ala Ser Gly
                325                 330                 335
Leu Ile Thr Ser Tyr Leu His Ile Arg Leu Gly Tyr Thr Phe Ser Ala
                340                 345                 350
Ser Phe Ile Asp Tyr Val Leu Gly Phe Lys Tyr Ala Gly His Pro Leu
                355                 360                 365
Leu Ile Trp Leu Val Gly Ile Gly Phe Phe Val Leu Tyr Phe Val Val
            370                 375                 380
Phe Tyr Phe Thr Ile Lys Ala Met Asn Ile Lys Thr Pro Gly Arg Glu
385                 390                 395                 400
Asp Asp Asp Ala Glu Gly Val Lys Lys Ile Asn Val Lys Gly Lys Ala
                405                 410                 415
Lys Ala Ala Lys Val Leu Glu Ala Ile Gly Gly Lys Asp Asn Ile Lys
            420                 425                 430
Val Leu Asp Ala Cys Ile Thr Arg Leu Arg Leu Asn Leu Asn Asp Pro
            435                 440                 445
Ser Leu Val Asp Lys Ala Thr Leu Lys Ala Leu Gly Ala Ala Gly Val
            450                 455                 460
Met Thr Ala Glu Asp Ser Val Gln Val Val Phe Gly Thr Glu Ala Glu
465                 470                 475                 480
Arg Ile Lys Asp Asp Ile Lys Ala Ile Ile Gln Asn Gly Gly Tyr Val
                485                 490                 495
Glu Asp Asp Ser Asp Lys Glu Glu Val Gln Glu Asp Lys Gln Ile
            500                 505                 510
Ser Lys Gly Ala His Glu Leu Leu Ser Pro Ala Asp Gly Glu Val Val
            515                 520                 525
Gly Ile Glu Ser Val Pro Asp Ser Thr Phe Ala Glu Lys Met Leu Gly
            530                 535                 540
Asp Gly Phe Ala Val Ile Pro Ser Gly Asn Glu Val His Ser Pro Ala
545                 550                 555                 560
Asp Gly Glu Val Ser Val Leu Phe Pro Thr Lys His Ala Phe Ala Ile
                565                 570                 575
Thr Thr Glu Gly Gly Leu Glu Leu Leu Ile His Val Gly Ile Asp Thr
            580                 585                 590
Val Ala Leu Asn Gly Glu Gly Phe Thr Ala His Val Lys Gln Gly Asp
            595                 600                 605
```

```
Lys Val Lys Lys Gly Asp Leu Ile Leu Thr Leu Asp Thr Glu Phe Ile
        610                 615                 620

Lys Ser Lys Gly Lys Asn Leu Ile Thr Pro Val Ile Val Thr Asn Met
625                 630                 635                 640

Asp Val Val Gly Asn Ile Asp Val Lys Leu Gly Asn Val Lys Asn Ser
                645                 650                 655

Glu Lys Ala Ala Asp Val Thr Val Lys
            660                 665

<210> SEQ ID NO 37
<211> LENGTH: 2226
<212> TYPE: DNA
<213> ORGANISM: Clostridium saccharobutylicum

<400> SEQUENCE: 37
atgttagttg atgcttttttt gcgcacaaag catctaaaac atccctatat acaaaaaata    60
tttaaaaaag gggaaaatgt tatgaaagac aaaattttttg gtattttaca gcgtgtagga   120
agatctttta tgcttccaat agctatttta ccagtagctg gattatttct tggtttaggt   180
ggatcattta ccaatgaaac aatgattcaa gcttatggac ttactgggtt aatcggacct   240
ggtacattta tttattcaat cctttctgta atgaatgcag caggaaatgt agtgtttggc   300
aatttgcctt tattatttgc aatgggtgtt gcaattggta tggctaaaaa ggaaaaagat   360
gttgcagctt tatcagcagc aattgcattc cttataatgc atgcatcaat aagtgctatg   420
attaatatta tggtggaact tgatgctctt cttagtggtg catcaacttc agtacttggt   480
attacttcat tacaaatggg tgttttttggt ggtattattg tagggcttgg agtagcagcg   540
ttacataata aattctataa aattgaatta ccacaggtat tatcattctt ggtggaact    600 agatttgttc caattgtaag tgcaataaca tatttaattg ttggaatttt aatgttttat   660
atttggcctc caattcaagg tggtatttat aaagttggag atcttgtatt aagatcagga   720
tatgcaggaa catggcttta tggtttaatg gaacgtttat taatacccttt tggtcttcat   780 catgtatttt acttaccatt ctggcaaaca gcagttggtg gtacagctac agtaggtggg   840
aaagttattg aaggtgctca aaatattttc tttgctgaac ttggaactcc aggaataaca   900
cactttagtg tttcagcaac aagatttatg tcaggtaaat tcccacttat gatatttggt   960
ttacctggag cagcgcttgc gatgtacaga tgtgcaaaac cagaaaagag aaagtagta  1020 ggtggattat tattatcagc agcattaact tcgatgttaa ctggtattac agaaccaatt  1080
gaatttacat tcttatttgt tgcaccatta ttatatggaa ttcactgcgt atttgctgga  1140
ctagcttata tgtttatgca tatgttaaat gttggagttg gtatgacttt ctctggtgga  1200
tttatagatt tattcttatt tggtattttta caaggaaatg ctaagacaag ttggatttgg  1260
gttgcagttg taggtattgc atattttgta gtatactatg tattgttctc tttcttaatt  1320
aagaagcttg acttaaagac tccaggtcgt gatgattctg aagaagttaa actttatcgt  1380
agaagcgatt tagatgcaaa gaaaaaaggt aataatgcag ataatggaga agtgaaagt  1440 atagatgaat tatcagctat gatctgtcaa ggtcttggtg gtaagaagaa tatttcagat  1500
gttgactgtt gcgcaactag attacgttgt acagttgtta aatcagaatt agtaaatgaa  1560
gctttattaa acaaactgg agcatcagga gtagttcata aaggcgtagg tgttcaaatt  1620
atatatggac caagagtaac agttataaaa tctaatttag aagattattt aattgcagca  1680
cctgatgaag aagttgctat agatgcagta gaagaaaaag cacctgaaat gccaactgaa  1740
```

-continued

```
aaggaagcgg aaggaaaagt tgttaataca atagttttaa gcagtccatt aacaggagat    1800
gctaaagatt tatcgaaagc tccagatgaa gcatttgcaa gcaaaatgat gggagacgga    1860
gcggtagtaa ttccaagtaa tggagatgtt gtagcaccag cagatggtga ggtgagtttt    1920
gtattcccat caaaacatgc agtaggatta acaacaactg atggtcttga attacttatt    1980
catataggaa tagatacagt aaagcttgat ggaaaaggct ttgaaacttt cgtaaaagaa    2040
ggagacaaag ttaaaaaagg tgataaatta ttaagctttg acttagaatt tataaaagaa    2100
aatgcaccat ctattgcatc accatgcatt tgtacagcat taagcagcaa acaaaaagta    2160
cgtttgttaa aaacaggtga tataaaggca ggagaagact taatagcaat tgatgtgctt    2220
gaataa                                                               2226
```

<210> SEQ ID NO 38
<211> LENGTH: 741
<212> TYPE: PRT
<213> ORGANISM: Clostridium saccharobutylicum

<400> SEQUENCE: 38

```
Met Leu Val Asp Ala Phe Leu Arg Thr Lys His Leu Lys His Pro Tyr
1               5                  10                  15

Ile Gln Lys Ile Phe Lys Lys Gly Glu Asn Val Met Lys Asp Lys Ile
            20                  25                  30

Phe Gly Ile Leu Gln Arg Val Gly Arg Ser Phe Met Leu Pro Ile Ala
        35                  40                  45

Ile Leu Pro Val Ala Gly Leu Phe Gly Leu Gly Gly Ser Phe Thr
    50                  55                  60

Asn Glu Thr Met Ile Gln Ala Tyr Gly Leu Thr Gly Leu Ile Gly Pro
65                  70                  75                  80

Gly Thr Phe Ile Tyr Ser Ile Leu Ser Val Met Asn Ala Ala Gly Asn
                85                  90                  95

Val Val Phe Gly Asn Leu Pro Leu Leu Phe Ala Met Gly Val Ala Ile
            100                 105                 110

Gly Met Ala Lys Lys Glu Lys Asp Val Ala Ala Leu Ser Ala Ala Ile
        115                 120                 125

Ala Phe Leu Ile Met His Ala Ser Ile Ser Ala Met Ile Asn Ile Asn
    130                 135                 140

Gly Gly Thr Asp Ala Leu Leu Ser Gly Ala Ser Thr Ser Val Leu Gly
145                 150                 155                 160

Ile Thr Ser Leu Gln Met Gly Val Phe Gly Gly Ile Ile Val Gly Leu
                165                 170                 175

Gly Val Ala Ala Leu His Asn Lys Phe Tyr Lys Ile Glu Leu Pro Gln
            180                 185                 190

Val Leu Ser Phe Phe Gly Gly Thr Arg Phe Val Pro Ile Val Ser Ala
        195                 200                 205

Ile Thr Tyr Leu Ile Val Gly Ile Leu Met Phe Tyr Ile Trp Pro Pro
    210                 215                 220

Ile Gln Gly Gly Ile Tyr Lys Val Gly Asp Leu Val Leu Arg Ser Gly
225                 230                 235                 240

Tyr Ala Gly Thr Trp Leu Tyr Gly Leu Met Glu Arg Leu Leu Ile Pro
                245                 250                 255

Phe Gly Leu His His Val Phe Tyr Leu Pro Phe Trp Gln Thr Ala Val
            260                 265                 270

Gly Gly Thr Ala Thr Val Gly Gly Lys Val Ile Glu Gly Ala Gln Asn
        275                 280                 285
```

```
Ile Phe Phe Ala Glu Leu Gly Thr Pro Gly Ile Thr His Phe Ser Val
    290                 295                 300

Ser Ala Thr Arg Phe Met Ser Gly Lys Phe Pro Leu Met Ile Phe Gly
305                 310                 315                 320

Leu Pro Gly Ala Ala Leu Ala Met Tyr Arg Cys Ala Lys Pro Glu Lys
                325                 330                 335

Arg Lys Val Val Gly Leu Leu Ser Ala Ala Leu Thr Ser Met
                340                 345                 350

Leu Thr Gly Ile Thr Glu Pro Ile Glu Phe Thr Phe Leu Phe Val Ala
            355                 360                 365

Pro Leu Leu Tyr Gly Ile His Cys Val Phe Ala Gly Leu Ala Tyr Met
        370                 375                 380

Phe Met His Met Leu Asn Val Gly Val Gly Met Thr Phe Ser Gly Gly
385                 390                 395                 400

Phe Ile Asp Leu Phe Leu Phe Gly Ile Leu Gln Gly Asn Ala Lys Thr
                405                 410                 415

Ser Trp Ile Trp Val Ala Val Val Gly Ile Ala Tyr Phe Val Val Tyr
                420                 425                 430

Tyr Val Leu Phe Ser Phe Leu Ile Lys Lys Leu Asp Leu Lys Thr Pro
            435                 440                 445

Gly Arg Asp Asp Ser Glu Glu Val Lys Leu Tyr Arg Arg Ser Asp Leu
        450                 455                 460

Asp Ala Lys Lys Lys Gly Asn Asn Ala Asp Asn Gly Glu Ser Glu Ser
465                 470                 475                 480

Ile Asp Glu Leu Ser Ala Met Ile Cys Gln Gly Leu Gly Gly Lys Lys
                485                 490                 495

Asn Ile Ser Asp Val Asp Cys Cys Ala Thr Arg Leu Arg Cys Thr Val
            500                 505                 510

Val Lys Ser Glu Leu Val Asn Glu Ala Leu Leu Lys Gln Thr Gly Ala
        515                 520                 525

Ser Gly Val Val His Lys Gly Val Gly Val Gln Ile Ile Tyr Gly Pro
        530                 535                 540

Arg Val Thr Val Ile Lys Ser Asn Leu Glu Asp Tyr Leu Ile Ala Ala
545                 550                 555                 560

Pro Asp Glu Glu Val Ala Ile Asp Ala Val Glu Glu Lys Ala Pro Glu
                565                 570                 575

Met Pro Thr Glu Lys Glu Ala Glu Gly Lys Val Val Asn Thr Ile Val
            580                 585                 590

Leu Ser Ser Pro Leu Thr Gly Asp Ala Lys Asp Leu Ser Glu Ala Pro
        595                 600                 605

Asp Glu Ala Phe Ala Ser Lys Met Met Gly Asp Gly Ala Val Val Ile
610                 615                 620

Pro Ser Asn Gly Asp Val Val Ala Pro Ala Asp Gly Glu Val Ser Phe
625                 630                 635                 640

Val Phe Pro Ser Lys His Ala Val Gly Leu Thr Thr Thr Asp Gly Leu
                645                 650                 655

Glu Leu Leu Ile His Ile Gly Ile Asp Thr Val Lys Leu Asp Gly Lys
            660                 665                 670

Gly Phe Glu Thr Phe Val Lys Glu Gly Asp Lys Val Lys Lys Gly Asp
        675                 680                 685

Lys Leu Leu Ser Phe Asp Leu Glu Phe Ile Lys Glu Asn Ala Pro Ser
        690                 695                 700
```

-continued

```
Ile Ala Ser Pro Cys Ile Cys Thr Ala Leu Ser Ser Lys Gln Lys Val
705                 710                 715                 720

Arg Leu Leu Lys Thr Gly Asp Ile Lys Ala Gly Glu Asp Leu Ile Ala
                725                 730                 735

Ile Asp Val Leu Glu
            740
```

MIXOTROPHIC FERMENTATION METHOD FOR MAKING ACETONE, ISOPROPANOL, BUTYRIC ACID AND OTHER BIOPRODUCTS, AND MIXTURES THEREOF

CROSS-REFERENCE TO RELATED APPLICATIONS

The instant application claims priority to U.S. Provisional Application No. 62/121,871, filed Feb. 27, 2015; U.S. Provisional Application No. 62/183,034, filed Jun. 22, 2015; U.S. Provisional Application No. 62/199,548, filed Jul. 31, 2015; U.S. Provisional Application No. 62/209,133, filed Aug. 24, 2015; and U.S. Provisional Application No. 62/265,239, filed Dec. 9, 2015, the disclosures of each of which is incorporated by reference herein in their entireties.

SEQUENCE LISTING

The instant application contains a Sequence Listing which has been submitted electronically in ASCII format and is hereby incorporated by reference in its entirety. Said ASCII copy, created on Feb. 24, 2016, is named P49168$_{13}$SL.txt and is 104,007 bytes in size.

FIELD OF INVENTION

The invention relates to the field of production of bioproducts such as alcohols, organic acids of less than 7 carbons, acetone, and mixtures thereof with microorganisms.

BACKGROUND

The production costs for biofuels and certain other bioproducts via microbial fermentation is currently high, particularly compared to oil-derived fuels. Feedstock and feedstock pre-treatment costs for use in such methods can form 50-60% or more of total operating costs. Generally these costs relate to the carbohydrates used as the carbon source in the production of the biofuels. Because these costs are so high, they are one of the primary factors affecting the economic viability of cellulosic and other next generation biofuel manufacturing processes. There is therefore a strong need for lowering these costs and for producing desired products at high yield and high titers. One way to mitigate high feedstock costs is by maximizing feedstock conversion to the product of interest.

However, conventional methods for maximizing feedstock conversion are fraught with difficulties. For example, attempts to ferment gaseous substrates with autotrophic organisms have been hindered by difficulties in reaching suitable concentrations of the substrate and by low titers, which increase isolation-related operating costs. Autotrophic fermentation has also been limited in the range of economically attainable products.

From a metabolic perspective, acetyl-CoA is a central building block and a link between glycolysis and fermentative alcohol production. Consequently acetyl-CoA serves as a focal point for biofuel production in microbial organisms. However, the ability to achieve metabolically efficient production of acetyl-CoA (and high mass yields) has historically been impeded by $CO_2$ loss during decarboxylation reactions involved in classical Embden-Meyerhof-Parnas (EMP) glycolysis. For example, one molecule of glucose (where glucose is the carbon source) under heterotrophic growth conditions may be used to generate two molecules of acetyl-CoA and excess ATP, but this occurs at the "expense" of two $CO_2$ molecules, which are lost in the conversion of pyruvate to acetyl-CoA. In contrast, two molecules of $CO_2$ (where gaseous $CO_2$ is the carbon source) under autotrophic growth conditions may generate one molecule of acetyl-CoA, but this scheme results in a net ATP formation of less than 1, and acetate production (from acetyl-CoA) is required to generate more ATP.

Accordingly, there is a need for fermentation methods and engineering metabolic pathways that minimize—or ideally eliminate—$CO_2$ losses and result in complete conversion of a carbohydrate source into acetyl-CoA without having to sacrifice the acetyl-CoA produced for further generation of ATP.

SUMMARY OF THE INVENTION

Herein is provided a mixotrophic fermentation method comprising (i) providing an isolated naturally acetogenic organism, (ii) providing a first feedstock and a second feedstock wherein said first feedstock comprises a carbon source that is metabolized by the native form of the organism at a rate of less than 0.01 g/hr/g cell mass; and wherein said second feedstock comprises CO, $CO_2$, carbonate, bicarbonate, $H_2$, glycerol, methanol, formate, urea or a combination thereof; and (iii) culturing said organism in a fermentation medium, whereby both feedstocks are metabolized and a fermentation broth is formed, which broth comprises at least one bioproduct.

In an embodiment, the method yields a greater amount of the at least one bioproduct than the combined amounts of the at least on bioproduct produced by heterotrophic and autotrophic fermentation with the same organism under the same conditions.

In an embodiment, the method may comprise production of at least one bioproduct and acetic acid as a second bioproduct, wherein the amount of acetic acid produced per biomass unit weight is less than about 50% of that produced in autotrophic fermentation with the same organism under the same conditions.

In an embodiment, the carbon yield, based on the total amount of carbon in produced bioproducts divided by the total amount of carbon metabolized from said first feedstock, is at least 50%.

In an embodiment, the $^{13}C/^{12}C$ isotope ratio of the carbon present in the bioproduct may be less than that of atmospheric $CO_2$.

In an embodiment, said carbon source may be selected from carbohydrates, glycerol, methanol, or a combination thereof.

In embodiment, said organism may be *Clostridia*.

In an embodiment, said organism may be genetically modified.

In an embodiment, said first feedstock and said second feedstock may be present in the fermentation medium at the same time.

In an embodiment, said fermentation medium may comprise a carbohydrate and at least one of CO, $CO_2$, and hydrogen.

In an embodiment, said fermentation medium comprises a steel mill produced CO composition.

In an embodiment, the culturing may be performed in whole or in part at a super-atmospheric pressure.

In an embodiment, said bioproduct may be selected from the group consisting of even numbered primary alcohols, odd numbered secondary alcohols, organic acids of less than 7 carbons, C3 compounds, C4 compounds, and mixtures thereof.

In an embodiment, said bioproduct may be selected from the group consisting of acetic acid, acetone, propionic acid, butyric acid, hexanoic acid, 3-hydroxypropionic acid, 3-hydroxybutyric acid, crotonic acid, acetoacetic acid, lactic acid, 2-hydroxyisobutyric acid, 3-methylbutanoic acid, ethanol, butanol, crotyl alcohol, hexanol, acetone, isopropanol, 2,3-butanediol, acetoin, 1,3-propanediol, and combinations thereof.

In an embodiment, said bioproduct may be non-naturally occurring.

In an embodiment, said broth may comprise a first bioproduct and a second bioproduct, wherein said first bioproduct is selected from the group consisting of acetoacetic acid, acetone, isopropanol, 3-hydroxybutyric acid, 2-hydroxyisobutyric acid, and combinations thereof, said second bioproduct is selected from the group consisting of ethanol, butanol, crotyl alcohol, hexanol, and combinations thereof, and the molar ratio between said first bioproduct and said second bioproduct is in the range from 0.1 to 0.95.

In an embodiment, the second feedstock may comprise CO, $CO_2$, carbonate, bicarbonate, methanol, or a combination thereof; and the $^{13}C/^{12}C$ isotope ratio of the carbon present in said second feedstock may be less than that of atmospheric $CO_2$.

In an embodiment, the method may comprise providing said fermentation medium with a mixture of CO, and hydrogen at a molar ratio in the range from 1:0.1 to 1:5.

In an embodiment, the method may further comprise steam reforming of a hydrocarbon to form said mixture of $CO_2$ and hydrogen.

In an embodiment, the first feedstock may comprise a sugar selected from glucose and sucrose, and the organism may metabolize $CO_2$ produced on metabolizing the sugar.

In an embodiment, the first feedstock may comprise a sugar selected from glucose and sucrose, the second feedstock may comprise at least one of $H_2$ and methanol, and the organism may metabolize $CO_2$ produced on metabolizing the sugar.

In an embodiment, said at least one bioproduct is acetone. In such an embodiment, the first feedstock may comprise a sugar selected from glucose and sucrose, and the organism may metabolize $CO_2$ produced on metabolizing the sugar.

In an embodiment, said at least one bioproduct is butyric acid. In such an embodiment, the first feedstock may comprise a sugar selected from glucose and sucrose, and the organism may metabolize $CO_2$ produced on metabolizing the sugar.

In an embodiment, said at least one bioproduct is isopropanol. In such an embodiment, the first feedstock may comprise a sugar selected from glucose and sucrose, and the organism may metabolize $CO_2$ produced on metabolizing the sugar.

In an embodiment, the metabolizing of the first feedstock does not inhibit the metabolizing of the second feedstock.

In an embodiment, the first feedstock may comprise a non-preferred sugar and the second feedstock may comprise CO, $CO_2$, carbonate, bicarbonate, $H_2$, glycerol, methanol, formate, urea or a combination thereof.

Herein is also provided a mixotrophic fermentation method comprising (i) providing an isolated naturally acetogenic organism, (ii) providing a fermentation medium comprising a first feedstock and a second feedstock wherein said first feedstock comprises a carbon source that is metabolized by the native form of the organism at a rate of less than 0.01 g/hr/g cell mass; and (iii) culturing said organism in said fermentation medium, whereby both feedstocks are metabolized and acetic acid is produced, wherein the amount of acetic acid produced per biomass unit weight is less than about 50% of that produced in autotrophic fermentation with the same organism under the same conditions.

Herein is also provided a mixotrophic fermentation method comprising (i) providing an isolated naturally acetogenic organism that has been genetically modified, (ii) providing a fermentation medium comprising a first feedstock and a second feedstock wherein said first feedstock comprises a sugar that is metabolized by the native form of the organism at a rate of less than 0.01 g/hr/g cell mass; and wherein said second feedstock comprises CO, $CO_2$, carbonate, bicarbonate, $H_2$, glycerol, methanol, formate, urea or a combination thereof; and (iii) culturing said organism in said fermentation medium, whereby both feedstocks are metabolized and a fermentation broth is formed, which broth comprises at least one bioproduct.

DETAILED DESCRIPTION OF THE INVENTION

Figure 1:
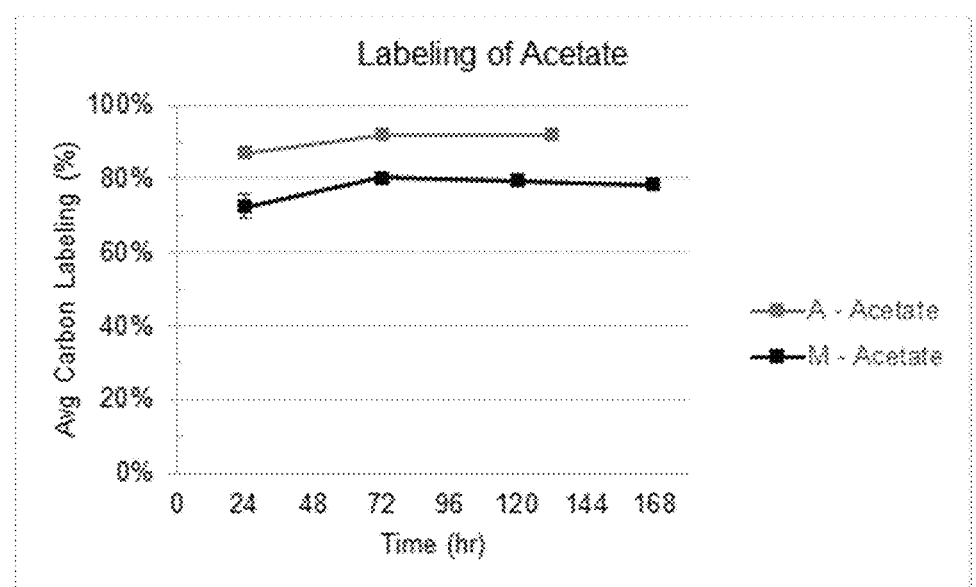
FIG. 1 shows $^{13}C$ labeling of acetate in *C. ljungdahlii* grown under autotrophic (A-Acetate) and mixotrophic (M-Acetate) cultures.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

One way to mitigate high feedstock costs is by maximizing feedstock conversion to the product of interest.

The inventors provide herein a mixotrophic fermentation method comprising (i) providing an isolated naturally acetogenic organism, (ii) providing a first feedstock and a second feedstock wherein said first feedstock comprises a carbon source that is metabolized by the native form of the organism at a rate of less than 0.01 g/hr/g cell mass; and wherein said second feedstock comprises CO, $CO_2$, carbonate, bicarbonate, $H_2$, glycerol, methanol, formate, urea or a combination thereof; and (iii) culturing said organism in a fermentation medium, whereby both feedstocks are metabolized and a fermentation broth is formed, which broth comprises at least one bioproduct.

Herein is also provided a mixotrophic fermentation method comprising (i) providing an isolated organism capable of metabolizing $CO_2$ into acetyl-CoA; (ii) providing a fermentation medium comprising a first feedstock and a second feedstock wherein said first feedstock comprises carbohydrates, glycerol, methanol, or combinations thereof; and wherein said second feedstock comprises CO, $CO_2$, carbonate, bicarbonate, $H_2$, glycerol, methanol, formate, urea or mixtures thereof; and (iii) culturing said organism in said fermentation medium, whereby both feedstocks are metabolized and a fermentation broth is formed, which broth comprises at least one bioproduct.

In an embodiment, the method may further comprise separating at least one bioproduct from said broth to form a separated bioproduct.

In an embodiment, also provided is a method as above, wherein the method achieves greater production of the at least one bioproduct than the combined amounts produced by heterotrophic and autotrophic fermentation with the same organism under the same conditions.

In an embodiment, also provided is a method as above, comprising production of at least one bioproduct and acetic acid.

In an embodiment, also provided is a method as above, wherein the amount of acetic acid produced per biomass unit weight is less than about 50% of that produced in autotrophic fermentation with the same organism under the same conditions.

In an embodiment, also provided is a method as above, wherein the carbon yield, based on the total amount of carbon in produced metabolites divided by the total amount of carbon metabolized from said first feedstock, is at least 50%.

In an embodiment, also provided is a method as above, wherein said bioproduct is characterized by a $^{13}C/^{12}C$ isotope ratio of less than that of atmospheric $CO_2$.

In an embodiment, also provided is a method as above, wherein said first feedstock and said second feedstock are present in the fermentation medium at the same time.

In an embodiment, also provided is a method as above, wherein said fermentation medium comprises a carbohydrate and at least one of CO, $CO_2$, and hydrogen.

In an embodiment, also provided is a method as above, wherein said fermentation medium comprises a steel mill produced CO composition.

In an embodiment, also provided is a method as above, wherein the first feedstock comprises juice extracted from at least one of sugarcane and sugarbeet.

In an embodiment, also provided is a method as above, wherein the culturing is performed in whole or in part at a super-atmospheric pressure.

In an embodiment, also provided is a method as above, wherein said bioproduct is selected from the group consisting of even numbered primary alcohols, odd numbered secondary alcohols, organic acids of less than 7 carbons, acetone, 2,3-butanediol, and mixtures thereof.

In an embodiment, also provided is a method as above, wherein said bioproduct is selected from the group consisting of acetic acid, propionic acid, butyric acid, hexanoic acid, 3-hydroxybutyric acid, crotonic acid, acetoacetic acid, lactic acid, 2-hydroxyisobutyric acid, 3-methylbutanoic acid, ethanol, butanol, crotyl alcohol, hexanol, acetone, isopropanol, 2,3-butanediol, acetoin, 1,3-propanediol and combinations thereof.

In an embodiment, also provided is a method as above, wherein said bioproduct is non-naturally occurring.

In an embodiment, also provided is a method as above, wherein said bioproduct is a C3 or a C4 compound.

In an embodiment, also provided is a method as above, wherein said bioproduct comprises a composition having multiple compounds and wherein one of said compounds is acetone.

In an embodiment, also provided is a method as above, wherein said broth comprises a first bioproduct and a second bioproduct, and wherein said first bioproduct is selected from the group consisting of acetoacetic acid, acetone, isopropanol, 3-hydroxybutyric acid, 2-hydroxyisobutyric acid, and combinations thereof. Also provided is such a method, wherein said second bioproduct is selected from the group consisting of ethanol, butanol, crotyl alcohol, hexanol, and combinations thereof. Also provided is such a method, wherein the molar ratio between said first bioproduct and said second bioproduct is in the range between 0.1 and 0.95.

In an embodiment, also provided is a method as above, wherein said second feedstock comprises CO, $CO_2$, carbonate, bicarbonate methanol, and mixtures thereof; and wherein the $^{13}C/^{12}C$ isotope ratio of the carbon present in said second feedstock is less than that of atmospheric $CO_2$.

In an embodiment, also provided is a method as above, wherein said second feedstock comprises at least one of ammonium carbonate and ammonium bicarbonate. Also provided is such a method, further comprising adding pressurized $CO_2$ to said fermentation medium.

In an embodiment, also provided is a method as above, wherein providing a fermentation medium includes providing said fermentation medium with a mixture of $CO_2$ and hydrogen at a molar ratio in the range between 1:0.1 and 1:5. Also provided is such a method further comprising steam reforming of a hydrocarbon to form said mixture of $CO_2$ and hydrogen. Also provided is such a method, wherein said hydrocarbon comprises methane.

In an embodiment, also provided is a method as above, wherein the bioproduct comprises at least one of butanol, butyric acid, acetic acid, lactic acid, 3-hydroxypropionic acid, 3-hydroxybutyric acid, crotonic acid, ethanol, acetone, isopropanol, 2,3-butanediol, acetoin, or crotyl-alcohol.

Also provided is such a method, wherein the first feedstock comprises a sugar selected from glucose and sucrose, the second feedstock comprises at least one of $H_2$ and methanol, and the organism assimilates or metabolizes CO, produced on metabolizing the sugar. In an embodiment, the organism may metabolize $CO_2$ produced during glycolysis. In an embodiment, the organism may metabolize $CO_2$ produced via other metabolic pathways, for example, via the acetoacetate pathway and/or the 2-keto acid pathway and/or the α-acetolactate pathway.

Also provided is such a method, wherein the first feedstock comprises methanol and the second feedstock comprises a bicarbonate supplemented with $CO_2$. Also provided is such a method, wherein the first feedstock comprises at least one of glucose and sucrose and the second feedstock comprises glycerol. Also provided is such a method, wherein the first feedstock comprises at least one of glucose and sucrose and the second feedstock comprises $CO_2$ and $H_2$. Also provided is such a method, wherein the first feedstock comprises at least one of glucose and sucrose and the second feedstock comprises CO, and methanol. Also provided is such method, wherein the first feedstock comprises methanol or glycerol and the second feedstock comprises $CO_2$ and In an embodiment, also provided is a method as above, wherein said at least one bioproduct is acetone.

Also provided is such a method, wherein said organism is acetogenic.

Also provided is such a method, wherein said organism is acetogenic Clostridia.

In an embodiment, also provided is a method as above, wherein said organism expresses genes of the Wood-Ljungdahl pathway.

Also provided is such a method, wherein said organism is selected from the group consisting of Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Clostridium carboxidivorans, Alkalibaculum bacchi, Clostridium drakei, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxobacter pfennigii, and Thermoanaerobacter kivui.

Also provided is such a method, wherein said organism is genetically modified to have a primary alcohol dehydrogenase gene or a secondary alcohol dehydrogenase gene deleted from its genome.

Also provided is such a method, wherein said organism is genetically modified to have a butanediol dehydrogenase gene deleted from its genome.

Also provided is such a method, wherein the first feedstock comprises a sugar selected from glucose and sucrose, and the second feedstock comprises at least one of $H_2$, and methanol, and the organism assimilates $CO_2$ produced during glycolysis.

Also provided is such a method, wherein the first feedstock comprises methanol and the second feedstock comprises a bicarbonate supplemented with $CO_2$.

Also provided is such a method, wherein the first feedstock comprises at least one of glucose and sucrose and the second feedstock comprises glycerol.

Also provided is such a method, wherein the first feedstock comprises at least one of glucose and sucrose and the second feedstock comprises $CO_2$ and $H_2$.

Also provided is such a method, wherein the first feedstock comprises at least one of glucose and sucrose and the second feedstock comprises $CO_2$ and methanol.

Also provided is such a method, wherein the first feedstock comprises at least one of glucose and sucrose and the second feedstock comprises $CO_2$.

Also provided is such a method, wherein the first feedstock comprises glucose and the second feedstock comprises CO. According to an embodiment, a method as described above is provided, wherein the feedstock glucose and feedstock CO are present in a glucose/CO weight/weight ratio of from about 0.3 to about 0.8.

Also provided is such a method, wherein the first feedstock comprises methanol or glycerol and the second feedstock comprises $CO_2$ and $H_2$.

Also provided is such a method, wherein the first feedstock comprises a carbohydrate, wherein said fermentation medium comprises a non-fermentable impurity, and wherein the impurity and the carbohydrate are present in the fermentation medium in a weight/weight ratio of greater than 0.05. In an embodiment, said impurity may be a fermentation inhibitor.

Also provided is such a method, wherein said broth comprises a second bioproduct, wherein said second bioproduct is selected from isopropanol and 3-hydroxybutyric acid and the molar ratio between acetone and said second bioproduct is greater than 5.

Also provided is such a method, further comprising separating acetone from said broth to form separated acetone. In an embodiment, said separating comprises evaporation. In an embodiment, said method further comprises catalytically converting said separated acetone into at least one acetone derivative. For example, herein is provided such a method comprising catalytically converting said separated acetone into one or more of mesitylene (1-3-5-trimethylbenzene), isophthalic acid, uvitic acid, and meta-xylene.

Also provided is such a method, wherein the method achieves greater production of acetone than the combined amounts of acetone produced by heterotrophic and autotrophic fermentation with the same organism under the same conditions.

Also provided is such a method, wherein said acetone has a $^{13}C/^{12}C$ isotope ratio of less than that of atmospheric $CO_2$.

Also provided is such a method, wherein said first feedstock and said second feedstock are present in the fermentation medium at the same time.

Also provided is such a method, comprising production of acetone and acetic acid. For example, in an embodiment, such a method is provided, wherein the amount of acetic acid formed per biomass unit weight is less than about 50% of that formed in autotrophic fermentation with the same organism under the same conditions.

Also provided is such a method, wherein said fermentation medium comprises at least one of CO, $CO_2$, and hydrogen.

Also provided is such a method, wherein said fermentation medium comprises a steel mill produced composition.

Also provided is such a method, wherein said at least one bioproduct is butyric acid.

Also provided is such a method, wherein the first feedstock comprises glucose, and the second feedstock comprises methanol at a glucose/methanol molar ratio of about 1:6.

Also provided is such a method further comprising separating butyric acid from said broth to form separated butyric acid.

Also provided is such a method, wherein said separating comprises contacting said broth with an organic solvent comprising a C6-C12 alkanol.

Also provided is such a method, wherein said separating comprises contacting said broth with an organic solvent comprising an ester of butyric acid and a C4-C12 alkanol.

Also provided is such a method, wherein said fermentation medium has a pH of greater than 5.5 and comprises calcium carbonate for pH control.

Also provided is such a method, wherein said calcium carbonate is present in second feedstock and also serves as a carbon source.

Also provided is such a method, wherein said fermentation medium has a pH greater than 5.5, and comprises a calcium base for pH control and wherein said separating comprises acidulating with sulfuric acid.

Also provided is such a method, further comprising catalytically converting said separated butyric acid into at least one butyric acid derivative.

Also provided is such a method, wherein said catalytically converting comprises hydrogenation and wherein said at least one butyric acid derivative comprises butanol.

Also provided is such a method, wherein said at least one bioproduct is isopropanol.

Also provided is such a method, wherein said broth comprises a second bioproduct, said second bioproduct is selected from acetone and 3-hydroxybutyric acid, and the molar ratio of isopropanol to said second bioproduct in said broth is greater than 5.

Also provided is such a method, further comprising separating isopropanol from said broth to form in separated isopropanol.

Also provided is such a method, wherein said separating comprises evaporation.

Also provided is such a method, further comprising catalytically converting said separated isopropanol into at least one isopropanol derivative.

Also provided is such a method, wherein said broth comprises more than one bioproduct and at least one bioproduct is isopropanol and another is acetone.

Also provided is such a method, wherein said broth comprises a third bioproduct, said third bioproduct is 3-hydroxybutyric acid, and the molar ratio of the combination of isopropanol and acetone to said third bioproduct is greater than 5.

Also provided is such a method further comprising separating isopropanol and acetone from said broth to form a separated composition comprising isopropanol and acetone.

Also provided is such a method, wherein said separating comprises evaporation.

Also provided is such a method further comprising catalytically converting the isopropanol and/or acetone present in said separated composition into at least one derivative of isopropanol or acetone.

According to an embodiment, said organism is acetogenic and said first feedstock comprises at least one non-preferred sugar. According to an embodiment said first feedstock further comprises at least one preferred sugar.

According to an embodiment, said non-preferred sugar is metabolized by a genetically modified acetogenic organism at a rate of at least 0.02 g/hr/g cell mass.

According to an embodiment, $CO_2$ is generated from metabolizing said non-preferred sugar and said generated $CO_2$ comprises at least a fraction of said second feedstock.

According to an embodiment, said non-preferred sugar is selected from the group consisting of glucose, mannose, galactose, arabinose, ribose, maltose, sucrose, lactose, cellobiose and mixtures thereof. According to an embodiment, said non-preferred sugar comprises glucose.

According to an embodiment, said organism is genetically modified to express at least one component of a phosphotransferase system (PTS). According to an embodiment, said at least one component is selected from the group consisting of enzymes EIIA, EIIB, EIIC, and combinations thereof.

According to an embodiment, said organism is genetically modified to express a gene related to a sugar transport system other than genes associated with the phosphotransferase system. According to an embodiment, said gene is selected from the group consisting of a symporter system utilizing a sodium ion ($Na^+$), a symporter system utilizing protons ($H^+$), a permease system and a combination thereof.

According to an embodiment, the rate of metabolizing said non-preferred sugar by said genetically modified organism is greater than that of metabolizing said non-preferred sugar by the native form of the organism by a factor of at least 1.5.

According to an embodiment, said bioproduct is selected from the group consisting of acetic acid, propionic acid, 3-hydroxypropionic acid, butyric acid, hexanoic acid, 3-hydroxybutyric acid, crotonic acid, acetoacetic acid, lactic acid, 2-hydroxyisobutyric acid, 3-methylbutanoic acid, ethanol, butanol, crotyl alcohol, hexanol, acetone, isopropanol, 2,3-butanediol, acetoin, 1,3-propanediol and combinations thereof.

Provided is a mixotrophic fermentation method comprising (i) providing an isolated organism capable of metabolizing $CO_2$ into acetyl-CoA; (ii) providing a first feedstock and a second feedstock for use in a fermentation medium, wherein said first feedstock comprises carbohydrates, glycerol, methanol or combinations thereof; and wherein said second feedstock comprises CO, $CO_2$, carbonate, bicarbonate, $H_2$, glycerol, methanol, formate, urea or mixtures thereof; (iii) culturing said organism in said fermentation medium, whereby both feedstocks are metabolized and a fermentation broth is formed, which broth comprises at least one bioproduct; and (iv) optionally separating said bioproduct from said broth.

According to an embodiment, the method provides a mixotrophic fermentation method that results in greater production of a target bioproduct or a combination of target bioproducts than the combined amounts produced by heterotrophic and autotrophic fermentation with the same organism under the same conditions. Said embodiment is exemplified by comparing three cases of fermenting with a given organism capable of and/or configured for use in the method. In the first case (referred to herein as heterotrophic fermentation), a microorganism is cultured in a fermentation medium comprising a first feedstock to form a heterotrophic fermentation broth. In the second case (referred to herein as autotrophic fermentation), the microorganism is cultured in a fermentation medium comprising a second feedstock to form an autotrophic fermentation broth. In the third case (referred to herein as mixotrophic fermentation), a microorganism is cultured in a fermentation medium comprising a mixture of the first feedstock and the second feedstock to form a mixotrophic fermentation broth. At the end of culturing time, the autotrophic fermentation broth is mixed with the heterotrophic fermentation broth to form a mixed fermentation broth. According to said embodiment, the mixotrophic fermentation method may achieve greater production of a target bioproduct or a combination of target bioproducts than the combined amounts produced by heterotrophic and autotrophic fermentation with the same microorganism under the same conditions. The nature of bioproducts in said mixotrophic fermentation and/or the molar ratio between the bioproducts (in case of forming multiple bioproducts), may differ from those of the mixed fermentation broth.

According to an embodiment, the method is characterized in that the amount of acetic acid formed per biomass unit weight is less than about 50% of that formed in autotrophic fermentation using the same organism, less than 40%, less than 30%, less than 20%, or less than 10%. Biomass refers to the total weight of solid biological material generated during fermentation. Biomass may be easily separated from the fermentation medium by, for example, centrifugation. Biomass does not include any solid biological material introduced into the fermentation medium by one or more feedstocks.

According to an embodiment, the method is characterized in carbon yield of at least 50%, at least 60%, at least 70%, at least 80%, at least 90%, at least 100%, at least 110%, at least 120%, at least 130%, at least 140%, at least 150%, or at least 160%. As used herein carbon yield may be calculated by dividing the total amount of carbon in bioproducts produced during fermentation by the total amount of carbon metabolized from the first feedstock during fermentation.

The method comprises providing an isolated, naturally occurring or non-naturally occurring organism capable of metabolizing $CO_2$. The organism may be autotrophic. In an embodiment, the organism may be capable of assimilating CO, $CO_2$, methanol, etc., for growth. The organism may also be capable of utilizing glycolysis for growth. Any organism capable of metabolizing $CO_2$ is suitable. According to an embodiment, said organism is acetogenic. In an embodiment, the organism is naturally acetogenic. An organism is "naturally acetogenic" if the wild-type (or native) organism is capable of metabolizing $CO_2$ into acetate using the Wood-Ljungdahl pathway (or reductive acetyl-CoA pathway). A naturally acetogenic organism may be a wild-type organism or genetically modified.

According to an embodiment, said organism is acetogenic *Clostridia*. According to an embodiment, the organism may be selected from the group consisting of *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Clostridium carboxidivorans, Alkalibaculum bacchi, Clostridium drakei, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxobacter pfennigii,* and *Thermoanaerobacter kivui.*

The organism may be genetically modified. For example, the organism may be genetically modified to reduce or eliminate expression of a primary alcohol dehydrogenase or a secondary alcohol dehydrogenase. In an embodiment, the organism may be genetically modified to have a primary alcohol dehydrogenase gene or a secondary alcohol dehydrogenase gene deleted from its genome. While a genomic deletion is a preferred embodiment, any genomic mutation resulting in inactivation of the enzyme would be sufficient, including but not limited to partial gene deletion, nonsense mutation, transcriptional promoter deletion, etc. In another embodiment, the transcriptional expression of this gene can be reduced by using antisense RNA.

Similarly, the organism may be genetically modified to reduce or eliminate nucleic acid and/or protein expression of butanediol dehydrogenase. In an embodiment, the organism may be genetically modified to have a butanediol dehydrogenase gene deleted from its genome. In another embodiment, the organism may be genetically modified to have a secondary alcohol dehydrogenase gene and a butanediol dehydrogenase gene deleted from its genome.

As used herein, a "secondary alcohol dehydrogenase" is an enzyme that catalyzes the reduction of a ketone to a secondary alcohol, for example, the reduction of acetone into 2-propanol (a.k.a. isopropanol). An exemplary amino acid sequence of the secondary alcohol dehydrogenase gene is the following amino acid sequence from *C. ljungdahlii* DSM 13528:

```
                                             (SEQ ID NO: 2)
MKGFAMLGINKLGWIEKKNPVPGPYDAIVHPLAVSPCTSDIHTVFEGALG

NRENMILGHEAVGEIAEVGSEVKDFKVGDRVIVPCTTPDWRSLEVQAGFQ

QHSNGMLAGWKESNEKDGVFADYFHVNDADMNLAILPDEIPLESAVMMTD

MMTTGFHGAELADIKMGSSVVVIGIGAVGLMGIAGSKLRGAGRIIGVGSR

PVCVETAKFYGATDIVNYKNGDIVEQIMDLTHGKGVDRVIMAGGGAETLA

QAVTMVKPGGVISNINYHGSGDTLPIPRVQWGCGMAHKTIRGGLCPGGRL

RMEMLRDLVLYKRVDLSKLVTHVFDGAENIEKALLLMKNKPKDLIKSVVT

F.
```

In an embodiment, an exemplary secondary alcohol dehydrogenase amino acid sequence may be an amino acid sequence which has at least 75%, 80%, 85%, 90%, 91%, 92%, 93%, 94%, 95%, 96%, 97%, 98%, or 99% identity to the above sequence, and which is capable of catalyzing the reduction of a ketone to a secondary alcohol.

As used herein, a "butanediol dehydrogenase" may be an oxidoreductase enzyme, with EC number 1.1.1.4, that catalyzes the reduction of a ketone group to an alcohol group, specifically converting acetoin into butanediol. An exemplary amino acid sequence encoded by the butanediol dehydrogenase gene is the following amino sequence from *C. ljungdahlii* DSM 13528:

```
                                               (SEQ ID NO: 4)
MKAVLWYDKKDVRVEEIEEPKVKENAVKIKVKWCGICGSDLHEYLGGPIF

IPVGTPHPLSKSTAPVVLGHEFSGEVVEIGSKVTKFKAGDRVIVEPIVAC

GKCPACLEGKYNLCEALGFHGLCGSGGGFAEYTVFPEDFVHKIPDTMDYE

QAALVEPMAVALHSLRVGNFTTGNTALVLGAGPIGLATIQCLKASGARIV

IVFQRKSVRQEYAKKFGADVVLDPNEVDVIEEIKKLTGGVGVDTSFETTG

ANVGINTAIQALKYEGTAVITSVWEKNAEINPNDLVFTEKKVVGTLAYRH

EFPSTIALMNDGRIKTDGYITKRIALEDIVKEGFETLTGPEKKKHVKIIV

TPDKSLL
```

In an embodiment, an exemplary butanediol dehydrogenase amino acid sequence may be an amino acid sequence which has at least 75%, 80%, 85%, 90%, 91%, 92%, 93%, 94%, 95%, 96%, 97%, 98%, or 99% identity to the above sequence, and which is capable of catalyzing the reduction of a ketone to an alcohol, specifically acetoin to butanediol. An exemplary nucleic acid sequence that encodes a butanediol dehydrogenase, which is from *C. ljungdahlii* DSM 13528, is as follows:

```
                                               (SEQ ID NO: 3)
ATGAAAGCTGTATTGTGGTATGATAAAAAAGATGTAAGAGTAGAGGAAAT

TGAGGAACCTAAGGTAAAAGAAAATGCTGTAAAAATTAAAGTGAAATGGT

GTGGTATATGTGGTTCTGACTTGCATGAGTATTTAGGAGGACCTATATTT

ATTCCAGTAGGTACGCCACATCCTTTAAGCAAGAGTACTGCACCAGTAGT

TTTAGGACATGAGTTTTCAGGAGAAGTAGTAGAAATAGGAAGCAAGGTTA

CAAAATTTAAAGCAGGAGATAGAGTTATTGTAGAACCTATAGTTGCCTGT

GGAAAGTGTCCTGCTTGTCTTGAAGGAAAATATAATTTATGTGAAGCTTT

GGGATTTCATGGACTTTGTGGAAGCGGCGGCGGATTTGCTGAATACACAG

TATTTCCTGAAGATTTTGTCCATAAGATACCAGATACTATGGACTATGAG

CAGGCTGCACTTGTTGAGCCTATGGCAGTTGCCCTTCATTCTCTAAGAGT

TGGAAACTTTACTACAGGAAATACTGCTTTGGTTTTAGGTGCAGGACCTA

TAGGACTTGCAACTATTCAGTGTTTAAAGGCATCAGGGGCAAGAATTGTA

ATTGTATTTCAGAGAAAATCTGTAAGACAGGAATATGCTAAGAAATTTGG

AGCAGATGTAGTTTTAGATCCAAATGAGGTAGATGTAATTGAAGAAATTA

AAAAACTTACAGGCGGCGTAGGCGTGGATACATCTTTTGAAACAACAGGT

GCAAATGTAGGGATTAATACGGCAATTCAAGCTTTAAAATATGAAGGTAC

TGCGGTAATAACCAGCGTATGGGAGAAAAATGCAGAAATCAATCCAAATG

ATCTTGTATTTACAGAAAAGAAGGTAGTTGGTACTCTTGCCTACAGACAT

GAATTTCCTTCTACAATAGCACTTATGAATGATGGAAGAATAAAGACAGA

CGGATATATTACAAAGAGAATAGCACTTGAGGACATTGTAAAAGAAGGAT

TTGAAACACTTACAGGACCTGAAAAGAAAAAACATGTAAAAATAATTGTA

ACTCCTGACAAATCCTTATTGTAA.
```

In an embodiment, an exemplary butanediol dehydrogenase nucleic acid sequence or an exemplary secondary alcohol dehydrogenase nucleic acid may be a nucleic acid sequence which has at least 75%, 80%, 85%, 90%, 91%, 92%, 93%, 94%, 95%, 96%, 97%, 98%, or 99% identity to a corresponding butanediol dehydrogenase or secondary alcohol dehydrogenase nucleic acid sequence as disclosed herein.

According to an embodiment, said organism expresses and/or comprises one or more biomolecules of the Wood-Ljungdahl pathway (or reductive acetyl-CoA pathway). Biomolecules of the Wood-Ljungdahl pathway include enzymes such as CO dehydrogenase and acetyl-CoA synthase, as well as genes encoding such enzymes. The Wood-Ljungdahl pathway metabolizes $CO_2$, which can be produced during glycolysis or fed exogenously, into acetyl-CoA. The acetyl-CoA is then fed into downstream pathways for production of other or additional bioproducts.

Rates and/or efficiencies relating to bioproduct formation and metabolite consumption achieved by the organism during the mixotrophic fermentation method of the invention may be higher than those achieved by the organism exposed to feedstocks comprising the same nutrients in the wild.

The method further comprises providing a fermentation medium comprising a first feedstock and a second feedstock. According to an embodiment, providing a fermentation medium comprises preparing an aqueous solution comprising said first feedstock and said second feedstock. According to an embodiment, providing comprises supplementing at least one of said first feedstock and said second feedstock during culturing. According to an embodiment, the fermentation medium comprises initially only the first feedstock and then the second feedstock is supplemented. According to an embodiment, supplementing said second feedstock is done before the first feedstock is fully utilized, e.g., at the time the first feedstock is only 10%, 20%, 30% or 40% utilized.

According to an embodiment, the fermentation medium may further comprise a steel mill gas composition. For example, the fermentation medium may comprise a steel mill gas composition comprising 40-80% CO, 10-25% $CO_2$, 2-5% $H_2$, and 15-35% $N_2$. In an embodiment, the fermentation medium may comprise a steel mill gas composition comprising 60-70% CO, 15-20% $CO_2$, 3-4% $H_2$, and 20-30% $N_2$. In an embodiment, the fermentation medium may comprise a steel mill gas composition comprising 43-55% CO, 17-20% $CO_2$, 2-3% $H_2$, and 25-34% $N_2$.

According to an embodiment, said fermentation medium comprises concurrently both said first feedstock and said second feedstock during at least a fraction of the culturing time, e.g., during at least 30% of the time, at least 40%, at least 50%, at least 60%, at least 70%, at least 80% or at least 90% of the time.

The first feedstock of the provided method may comprise carbohydrates, glycerol, methanol or combinations thereof. The second feedstock may comprise CO, $CO_2$, carbonate, bicarbonate, $H_2$, glycerol, methanol, formate, urea or mixtures thereof. When the first feedstock comprises glycerol or methanol, the second feedstock may or may not also comprise glycerol or methanol. In an embodiment, if methanol is present in the first feedstock, it need not be present in the second feedstock.

According to an embodiment, said carbohydrate comprises monosaccharides, such as glucose, fructose and xylose, disaccharides, such as sucrose, oligosaccharides, such as dextrins, polysaccharides, such as starch, xylan, cellulose and hemicellulose and combinations thereof. According to an embodiment, said carbohydrate comprises hexoses, such as glucose and fructose, pentoses, such as xylose and arabinose and combinations thereof.

According to an embodiment, said second feedstock comprises a gaseous compound and said gaseous compound is supplemented to the fermentation medium, e.g., via bubbling the gaseous compound through the medium. The methods for supplementing the fermentation medium and/or the feedstock with a carbon source are not limited, and include, for example, exogenously feeding a gaseous compound, such as CO or $CO_2$ or adding a carbon source and/or feedstock and/or additional components to an initially provided fermentation medium or feedstock later in time during fermentation.

According to an embodiment, said fermentation medium is kept during at least a fraction of the culturing time at a super-atmospheric pressure, e.g., during at least 30% of the time, at least 40%, at least 50%, at least 60%, at least 70%, at least 80% or at least 90% of the time. According to an embodiment, said super-atmospheric pressure is in the range between about 1.1 bar and about 10 bar.

According to an embodiment, said second feedstock comprises $CO_2$ and said $CO_2$ results from another fermentation process. According to an embodiment, said another fermentation process produces ethanol. According to another embodiment, said first feedstock comprises a carbohydrate, and metabolizing said carbohydrate by said autotrophic organism results in generating at least one of $CO_2$ and hydrogen, which then provides at least a fraction of said second feedstock, e.g., at least 50%, at least 60%, at least 70%, at least 80% or at least 90%.

According to an embodiment, said second feedstock comprises CO, $CO_2$, carbonate, bicarbonate, methanol and mixtures thereof and the $^{13}C/^{12}C$ isotope ratio of said second feedstock is less than that of atmospheric $CO_2$.

According to an embodiment, said second feedstock comprises at least one of ammonium carbonate and ammonium bicarbonate. According to a related embodiment, the method further comprises supplementing pressurized $CO_2$ to said fermentation medium. According to an embodiment, providing said fermentation medium comprises dissolving ammonium bicarbonate and/or ammonium carbonate, and optionally other components, in water and adjusting the pH to a selected level by introducing $CO_2$. According to a related embodiment, a fraction of the $CO_2$ and/or carbonate is metabolized during said culturing and the method further comprises supplementing $CO_2$ in order to maintain the selected pH. The pH of the fermentation medium may be greater than 4, 4.5, 5, 5.5, 6, 6.5, 7, 7.5, 8, 8.5, 9, or 9.5. The pH of the fermentation medium may be in the range from 4-9.5, 5-8.5, or 5.5-7.5. Calcium carbonate may also be used as an agent for controlling pH. In an embodiment calcium carbonate may serve as both a buffering agent and a source of carbon in a feedstock, including, for example, in the second feedstock.

According to an embodiment, said fermentation medium comprises a carbohydrate and carbon monoxide. According to an embodiment, said fermentation medium comprises a carbohydrate and carbon dioxide. According to an embodiment, said fermentation medium comprises a carbohydrate and hydrogen. According to an embodiment, said fermentation medium comprises a carbohydrate and at least one of carbon monoxide, carbon dioxide and hydrogen.

According to an embodiment, said first feedstock comprises a monosaccharide, said second feedstock comprises at least one of carbon monoxide and carbon dioxide and the weight ratio between said monosaccharide and said at least one of carbon monoxide and carbon dioxide is in the range from 0.1 to 10.

According to an embodiment, said providing a fermentation medium comprises providing said fermentation medium with a mixture of $CO_2$ and hydrogen at molar ratio in the range from about 1:0.1 to about 1:5. According to an embodiment, said providing said mixture further comprises steam reforming a hydrocarbon to form said mixture of $CO_2$ and hydrogen. According to an embodiment, said hydrocarbon comprises methane.

The provided method comprises culturing said organism in said fermentation medium, whereby both feedstocks are metabolized and a fermentation broth is formed, which broth comprises at least one bioproduct.

According to an embodiment, the consumption rate of said first feedstock is in the range from 0.01 to 10 mM/hr/$OD_{600}$, where $OD_{600}$ is the absorbance value of the culture read at a wavelength of 600 nm. According to an embodiment, the consumption rate of said second feedstock is in the range from 0.01 to 100 mM/hr/$OD_{600}$, where $OD_{600}$ is the absorbance value of the culture read at a wavelength of 600 nm.

According to an embodiment, the produced bioproduct is a metabolic derivative of acetyl-CoA.

According to an embodiment, said bioproduct is selected from the group consisting of even numbered primary alcohols, odd numbered secondary alcohols, organic acids of less than 7 carbons, C3 compounds, C4 compounds, and mixtures thereof.

According to an embodiment, said bioproduct is selected from the group consisting of acetic acid, propionic acid, butyric acid, hexanoic acid, 3-hydroxypropionic acid, 3-hydroxybutyric acid, crotonic acid, acetoacetic acid, lactic acid, 2-hydroxyisobutyric acid, 3-methylbutanoic acid, ethanol, isopropanol, butanol, crotyl alcohol, hexanol, acetone, isopropanol, 2,3-butanediol, acetoin, 1,3-propanediol and combinations thereof. In an embodiment, butanol may be n-butanol.

According to an embodiment, said bioproduct is non-naturally occurring. As used herein a non-naturally occurring bioproduct is a product which is unattainable by said organism when cultured in autotrophic conditions or is produced from a metabolic pathway not native to said organism.

According to an embodiment, said bioproduct is a $C_4$ compound.

According to an embodiment, said bioproduct comprises multiple compounds and one of said compounds is acetone.

According to an embodiment, said broth comprises a first bioproduct and a second bioproduct, and said first bioproduct is selected from the group consisting of acetoacetic acid, acetone, isopropanol, 3-hydroxybutyric acid, 2-hydroxyisobutyric acid, and combinations thereof. According to an embodiment, said second bioproduct is selected from the group consisting of ethanol, butanol, crotyl alcohol, hexanol, and combinations thereof. According to an embodiment, the molar ratio between said first bioproduct and said second bioproduct is in a range from 0.1 to 0.95.

A $^{13}C/^{12}C$ isotope ratio may be used as an indicator of nutrient cycling. For example, according to an embodiment, said bioproduct is characterized by a $^{13}C/^{12}C$ isotope ratio of less than that of atmospheric $CO_2$. In such a case, the $^{13}C/^{12}C$ isotope ratio would be indicative of production of the bioproduct from a non-atmospheric $CO_2$ source, for example, CO, $CO_2$, carbonate, bicarbonate, methanol or mixtures thereof present in the second feedstock.

Embodiments of the mixtotrophic fermentation method may include methods that advantageously utilize $CO_2$ and/or $H_2$ produced via sugar consumption (glycolysis) by the organism. Bioproducts produced by such methods may be any molecule that has a NAD(P)H to acetyl-CoA ratio of less than 2. These products include, for example, butanol, butyric acid, acetic acid, 3-hydroxypropionic acid, 3-hydroxybutyric acid, crotonic acid, ethanol, acetone, isopropanol, 2,3-butanediol, acetoin, and crotyl-alcohol.

As the sugar is metabolized, $CO_2$ and $H_2$ evolved by the organism may be exhausted into the fermentation broth at the molecular level. This molecular-scale gas dispersion may provide an excellent source of $CO_2$ or $H_2$ for re-assimilation. No input energy is required for dissolving these molecules into the fermentation broth. No gas dispersion technology known to the inventors can achieve molecular-scale gas dispersion with zero energy input. The components of the first and second feedstock and the ratio of the components of the first and second feedstock may depend on the nature of the bioproduct targeted for production.

In an embodiment, such methods may utilize $CO_2$ produced via glycolysis in combination with supplemented $H_2$ to produce bioproducts, such as butyric acid or butanol. Supplemented $H_2$ may be required because, as in the case of n-butanol or butyric acid production, not enough electrons are released during fermentation to allow for complete re-assimilation of glycolysis-derived $CO_2$. Thus, $H_2$ may provide an electron source for re-assimilation of the glycolysis-derived $CO_2$.

However, dispersion of gaseous hydrogen may be difficult and/or energy intensive. Accordingly, in an embodiment butyric acid or n-butanol may be produced utilizing a first feedstock comprising methanol and a second feedstock comprising a bicarbonate such as sodium bicarbonate or ammonium bicarbonate. The bicarbonate may be supplemented with $CO_2$.

In an embodiment, the organism may consume sugar and methanol in a particular molar ratio. Sugar consumption during fermentation is generally too electron deficient to achieve complete re-assimilation of glycolysis-derived $CO_2$. Thus, concurrent use of methanol and sugar in a given ratio may achieve complete $CO_2$ assimilation without the need for external gas delivery to the fermentation medium. The sugar to methanol molar ratio may range depending on the bioproduct targeted for production. For example, the sugar to methanol molar ratio may range from 1/1 to 1/3 to 1/6 to 1/12. In an embodiment, butyric acid may be produced in a mixotrophic fermentation method comprising the use of a first feedstock comprising glucose and a second feedstock comprising methanol, wherein the molar ratio is 1 mole glucose to 6 moles methanol.

In another embodiment, a bioproduct may be generated by mixotrophic fermentation in a fermentation medium comprising a first feedstock comprising a sugar such as glucose and a second feedstock comprising glycerol.

In another embodiment, a bioproduct may be generated by mixotrophic fermentation in a fermentation medium comprising a first feedstock comprising glucose and a second feedstock comprising supplemented $CO_2$ and $H_2$.

In another embodiment, a bioproduct may be generated by mixotrophic fermentation in a fermentation medium comprising a first feedstock comprising glucose and a second feedstock comprising methanol and supplemented $CO_2$.

In another embodiment, a bioproduct may be generated by mixotrophic fermentation in a fermentation medium comprising a first feedstock comprising methanol or glycerol and a second feedstock comprising supplemented $CO_2$ and $H_2$.

Optionally said method further comprises separating said bioproduct from said broth. Any separation method is suitable. According to various embodiments, separating comprises distillation, solvent extraction, crystallization, ion-exchange, membrane separation and combinations thereof.

In an embodiment, the bioproduct may be separated by evaporation, wherein evaporation means any transfer into the vapor phase, e.g., distillation, stripping, etc. In another embodiment, the bioproduct may be, for example, acetone, and the method includes catalytically converting said separated acetone into at least one acetone derivative. In an embodiment, such a method may comprise catalytically converting said separated acetone into one or more of mesitylene (1-3-5-trimethylbenzene), isophthalic acid, uvitic acid, and meta-xylene.

Production of Acetone

Provided herein is a mixotrophic fermentation method for the production of acetone comprising (i) providing an isolated organism capable of metabolizing $CO_2$ into acetyl-CoA; (ii) providing a fermentation medium comprising a first feedstock and a second feedstock wherein said first feedstock comprises carbohydrates, glycerol, methanol, or combinations thereof; and wherein said second feedstock comprises CO, $CO_2$, carbonate, bicarbonate, $H_2$, glycerol, methanol, formate, urea or mixtures thereof; and (iii) culturing said organism in said fermentation medium, whereby both feedstocks are metabolized and a fermentation broth is formed, which broth comprises at least one bioproduct that includes acetone.

Also provided is such a method, wherein said organism is acetogenic.

Also provided is such a method, wherein said organism is acetogenic *Clostridia*.

Also provided is such a method, wherein said organism is selected from the group consisting of *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Clostridium carboxidivorans, Alkalibaculum bacchi, Clostridium drakei, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxobacter pfennigii,* and *Thermoanaerobacter kivui*.

Also provided is such a method, wherein said organism is genetically modified to have a primary alcohol dehydrogenase gene or a secondary alcohol dehydrogenase gene deleted from its genome.

Also provided is such a method, wherein said organism is genetically modified to have butanediol dehydrogenase deleted from its genome.

Also provided is such a method, wherein the first feedstock comprises a sugar selected from glucose and sucrose, and the second feedstock comprises at least one of $H_2$, and methanol, and the organism assimilates $CO_2$ produced during glycolysis. Also provided is such a method, wherein the first feedstock comprises methanol and the second feedstock comprises a bicarbonate supplemented with $CO_2$. Also provided is such a method, wherein the first feedstock comprises at least one of glucose and sucrose and the second feedstock comprises glycerol. Also provided is such a method, wherein the first feedstock comprises at least one of glucose and sucrose and the second feedstock comprises $CO_2$ and $H_2$. Also provided is such a method, wherein the first feedstock comprises at least one of glucose and sucrose and the second feedstock comprises $CO_2$ and methanol. Also provided is such a method, wherein the first feedstock comprises at least one of glucose and sucrose and the second feedstock comprises $CO_2$. Also provided is such a method, wherein the first feedstock comprises glucose and the second feedstock comprises CO. According to an embodiment, a method as described above is provided, wherein the feedstock glucose and feedstock CO are present in a glucose/CO weight/weight ratio of from about 0.3 to about 0.8, e.g., from about 0.25 to about 0.85, from about 0.4 to about 0.7, from about 0.5 to about 0.6. Also provided is such a method, wherein the first feedstock comprises methanol or glycerol and the second feedstock comprises $CO_2$ and $H_2$. Also provided is such a method, wherein the first feedstock comprises a carbohydrate, wherein said fermentation medium comprises a non-fermentable impurity and wherein the impurity and the carbohydrate are present in the fermentation medium in a weight/weight ratio of greater than 0.05. In an embodiment, said impurity may be a fermentation inhibitor.

Also provided is such a method, wherein said broth comprises a second bioproduct, wherein said second bioproduct is selected from isopropanol and 3-hydroxybutyric acid and the molar ratio between acetone and said second bioproduct is greater than 5.

Also provided is such a method, further comprising separating acetone from said broth to form separated acetone. In an embodiment, said separating comprises evaporation. In an embodiment, said method further comprises catalytically converting said separated acetone into at least one acetone derivative. For example, herein is provided such a method comprising catalytically converting said separated acetone into one or more of mesitylene (1-3-5-trimethylbenzene), isophthalic acid, uvitic acid, and meta-xylene.

Also provided is such a method, wherein the method achieves greater production of acetone than the combined amounts of acetone produced by heterotrophic and autotrophic fermentation with the same organism under the same conditions.

Also provided is such a method, wherein said second feedstock comprises CO, $CO_2$, carbonate, bicarbonate, methanol, and mixtures thereof; and wherein the $^{13}C/^{12}C$ isotope ratio of the carbon present in said second feedstock is less than that of atmospheric $CO_2$.

Also provided is such a method, wherein said acetone has a $^{13}C/^{12}C$ isotope ratio of less than that of atmospheric $CO_2$.

Also provided is such a method, wherein said first feedstock and said second feedstock are present in the fermentation medium at the same time.

Also provided is such a method, wherein the culturing is performed in whole or in part at a super-atmospheric pressure.

Also provided is such a method, wherein providing a fermentation medium comprises providing said fermentation medium with a mixture of $CO_2$ and hydrogen at a molar ratio in the range between 1:0.1 and 1:5.

Also provided is such a method, comprising production of acetone and acetic acid. For example, in an embodiment, such a method is provided, wherein the amount of acetic acid formed per biomass unit weight is less than about 50% of that formed in autotrophic fermentation with the same organism under the same conditions.

Also provided is such a method, wherein said fermentation medium comprises at least one of CO, $CO_2$, and hydrogen.

Also provided is such a method, wherein said fermentation medium comprises a steel mill produced composition.

Production of Butyric Acid

Provided herein is a mixotrophic fermentation method for the production of butyric acid comprising (i) providing an isolated organism capable of metabolizing $CO_2$ into acetyl-CoA; (ii) providing a fermentation medium comprising a first feedstock and a second feedstock wherein said first feedstock comprises carbohydrates, glycerol, methanol, or combinations thereof; and wherein said second feedstock comprises CO, $CO_2$, carbonate, bicarbonate, $H_2$, glycerol, methanol, formate, urea or mixtures thereof; and (iii) culturing said organism in said fermentation medium, whereby both feedstocks are metabolized and a fermentation broth is formed, which broth comprises at least one bioproduct that includes butyric acid.

Also provided is such a method wherein said organism is selected from the group consisting of *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Clostridium carboxidivorans, Alkalibaculum bacchi, Clostridium drakei, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxobacter pfennigii,* and *Thermoanaerobacter kivui.*

Also provided is such a method wherein the first feedstock comprises a sugar selected from glucose and sucrose, and the second feedstock comprises at least one of $H_2$ and methanol and the organism assimilates $CO_2$ produced during glycolysis.

Also provided is such a method wherein the first feedstock comprises glucose, and the second feedstock comprises methanol at a glucose/methanol molar ratio of about 1:6, e.g., in a range from about 1:3 to about 1:4, from about 1:5 to about 1:6, from about 1:7 to about 1:9.

Also provided is such a method wherein the first feedstock comprises methanol and the second feedstock comprises a bicarbonate supplemented with $CO_2$.

Also provided is such a method wherein the first feedstock comprises at least one of glucose and sucrose and the second feedstock comprises glycerol.

Also provided is such a method wherein the first feedstock comprises at least one of glucose and sucrose and the second feedstock comprises $CO_7$ and $H_2$.

Also provided is such a method wherein the first feedstock comprises at least one of glucose and sucrose and the second feedstock comprises $CO_2$ and methanol.

Also provided is such a method wherein the first feedstock comprises at least one of glucose and sucrose and the second feedstock comprises $CO_2$.

Also provided is such a method wherein the first feedstock comprises glucose and the second feedstock comprises CO. In an embodiment, such a method is provided wherein the feedstock glucose and feedstock CO are present in a glucose/CO weight/weight ratio of from about 0.3 to about 0.8, e.g., from about 0.25 to about 0.85, from about 0.4 to about 0.7, from about 0.5 to about 0.6.

Also provided is such a method wherein the first feedstock comprises methanol or glycerol and the second feedstock comprises $CO_2$ and $H_2$.

Also provided is such a method wherein the first feedstock comprises a carbohydrate, wherein said fermentation medium comprises a non-fermentable impurity and wherein the impurity and the carbohydrate are present in the fermentation medium in a weight/weight ratio of greater than 0.05. In an embodiment, the impurity may be a fermentation inhibitor.

Also provided is such a method further comprising separating butyric acid from said broth to form separated butyric acid. The butyric acid may be separated by utilizing an organic solvent comprising a C6-C12 alkanol, a C4-C12 alkanol, and/or an ester of butyric acid.

Also provided is such a method wherein said fermentation medium has a pH of greater than 5.5 and comprises calcium carbonate for pH control. In an embodiment, the calcium carbonate is present in the said second feedstock and also serves as a carbon source. In another embodiment, said fermentation medium comprises a calcium base for pH control.

Also provided is such a method further comprising separating butyric acid from said broth wherein said separating comprises acidulating with sulfuric acid.

Also provided is such a method further comprising catalytically converting said separated butyric acid into at least one butyric acid derivative. In an embodiment, said catalytically converting comprises hydrogenation and said at least one butyric acid derivative comprises butanol.

Production of Isopropanol

Provided herein is a mixotrophic fermentation method for the production of isopropanol (also known a 2-propanol) comprising (i) providing an isolated organism capable of metabolizing $CO_2$ into acetyl-CoA; (ii) providing a fermentation medium comprising a first feedstock and a second feedstock wherein said first feedstock comprises carbohydrates, glycerol, methanol, or combinations thereof; and wherein said second feedstock comprises CO, $CO_2$, carbonate, bicarbonate, $H_2$, glycerol, methanol, formate, urea or mixtures thereof; and (iii) culturing said organism in said fermentation medium, whereby both feedstocks are metabolized and a fermentation broth is formed, which broth comprises at least one bioproduct that includes isopropanol.

Also provided is such a method, wherein said organism is acetogenic.

Also provided is such a method, wherein said organism is acetogenic *Clostridia*.

Also provided is such a method, wherein said organism is selected from the group consisting of *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Clostridium carboxidivorans, Alkalibaculum bacchi, Clostridium drakei, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxobacter pfennigii,* and *Thermoanaerobacter kivui.*

Also provided is such a method, wherein the first feedstock comprises a sugar selected from glucose and sucrose, and the second feedstock comprises at least one of $H_2$, and methanol, and the organism assimilates $CO_2$ produced during glycolysis. Also provided is such a method, wherein the first feedstock comprises methanol and the second feedstock comprises a bicarbonate supplemented with $CO_2$. Also provided is such a method, wherein the first feedstock comprises at least one of glucose and sucrose and the second feedstock comprises glycerol. Also provided is such a method, wherein the first feedstock comprises at least one of glucose and sucrose and the second feedstock comprises $CO_2$ and $H_2$. Also provided is such a method, wherein the first feedstock comprises at least one of glucose and sucrose and the second feedstock comprises $CO_2$ and methanol. Also provided is such a method, wherein the first feedstock comprises at least one of glucose and sucrose and the second feedstock comprises $CO_2$. Also provided is such a method, wherein the first feedstock comprises glucose and the second feedstock comprises CO. According to an embodiment, a method as described above is provided, wherein the feedstock glucose and feedstock CO are present in a glucose/CO weight/weight ratio of from about 0.3 to about 0.8, e.g., from about 0.25 to about 0.85, from about 0.4 to about 0.7, from about 0.5 to about 0.6. Also provided is such a method, wherein the first feedstock comprises methanol or glycerol and the second feedstock comprises $CO_2$ and $H_2$. Also provided is such a method, wherein the first feedstock comprises a carbohydrate, wherein said fermentation medium comprises a non-fermentable impurity and wherein the impurity and the carbohydrate are present in the fermentation medium in a weight/weight ratio of greater than 0.05. In an embodiment, said impurity may be a fermentation inhibitor.

Also provided is such a method, wherein said broth comprises a second bioproduct, wherein said second bioproduct is selected from acetone and 3-hydroxybutyric acid and the molar ratio between isopropanol and said second bioproduct is greater than 5.

Also provided is such a method, further comprising separating isopropanol from said broth to form separated isopropanol. In an embodiment, said separating comprises evaporation. In an embodiment, said method further comprises catalytically converting said separated isopropanol into at least one isopropanol derivative. For example, herein is provided such a method comprising catalytically converting said separated isopropanol into acetone.

Also provided is such a method, wherein the method achieves greater production of isopropanol than the combined amounts of isopropanol produced by heterotrophic and autotrophic fermentation with the same organism under the same conditions.

Also provided is such a method, wherein said second feedstock comprises CO, $CO_2$, carbonate, bicarbonate, methanol, and mixtures thereof; and wherein the $^{13}C/^{12}C$ isotope ratio of the carbon present in said second feedstock is less than that of atmospheric $CO_2$.

Also provided is such a method, wherein said isopropanol has a $^{13}C/^{12}C$ isotope ratio of less than that of atmospheric $CO_2$.

Also provided is such a method, wherein said first feedstock and said second feedstock are present in the fermentation medium at the same time.

Also provided is such a method, wherein the culturing is performed in whole or in part at a super-atmospheric pressure.

Also provided is such a method, wherein providing a fermentation medium comprises providing said fermentation medium with a mixture of $CO_2$ and hydrogen at a molar ratio in the range between 1:0.1 and 1:5.

Also provided is such a method, comprising production of isopropanol and acetic acid. For example, in an embodiment, such a method is provided, wherein the amount of acetic acid formed per biomass unit weight is less than about 50% of that formed in autotrophic fermentation with the same organism under the same conditions.

Also provided is such a method, wherein said fermentation medium comprises at least one of CO, $CO_2$, and hydrogen.

Also provided is such a method, wherein said fermentation medium comprises a steel mill produced composition.

Production of Isopropanol and Acetone

Provided herein is a mixotrophic fermentation method for the production of acetone and isopropanol comprising (i) providing an isolated organism capable of metabolizing $CO_2$ into acetyl-CoA; (ii) providing a fermentation medium comprising a first feedstock and a second feedstock wherein said first feedstock comprises carbohydrates, glycerol, methanol, or combinations thereof; and wherein said second feedstock comprises CO, $CO_2$, carbonate, bicarbonate, $H_2$, glycerol, methanol, formate, urea or mixtures thereof; and (iii) culturing said organism in said fermentation medium, whereby both feedstocks are metabolized and a fermentation broth is formed, which broth comprises more than one bioproduct and at least one bioproduct is isopropanol and another is acetone.

Also provided is such a method, wherein said organism is acetogenic.

Also provided is such a method, wherein said organism is acetogenic Clostridia.

Also provided is such a method, wherein said organism is selected from the group consisting of Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Clostridium carboxidivorans, Alkalibaculum bacchi, Clostridium drakei, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxobacter pfennigii, and Thermoanaerobacter kivui.

Also provided is such a method, wherein the first feedstock comprises a sugar selected from glucose and sucrose, and the second feedstock comprises at least one of $H_2$, and methanol, and the organism assimilates $CO_2$ produced during glycolysis. Also provided is such a method, wherein the first feedstock comprises methanol and the second feedstock comprises a bicarbonate supplemented with $CO_2$. Also provided is such a method, wherein the first feedstock comprises at least one of glucose and sucrose and the second feedstock comprises glycerol. Also provided is such a method, wherein the first feedstock comprises at least one of glucose and sucrose and the second feedstock comprises $CO_2$ and $H_2$. Also provided is such a method, wherein the first feedstock comprises at least one of glucose and sucrose and the second feedstock comprises $CO_2$ and methanol. Also provided is such a method, wherein the first feedstock comprises at least one of glucose and sucrose and the second feedstock comprises $CO_2$. Also provided is such a method, wherein the first feedstock comprises glucose and the second feedstock comprises CO. According to an embodiment, a method as described above is provided, wherein the feedstock glucose and feedstock CO are present in a glucose/CO weight/weight ratio of from about 0.3 to about 0.8, e.g., from about 0.25 to about 0.85, from about 0.4 to about 0.7, from about 0.5 to about 0.6. Also provided is such a method, wherein the first feedstock comprises methanol or glycerol and the second feedstock comprises $CO_2$ and $H_2$. Also provided is such a method, wherein the first feedstock comprises a carbohydrate, wherein said fermentation medium comprises a non-fermentable impurity and wherein the impurity and the carbohydrate are present in the fermentation medium in a weight/weight ratio of greater than 0.05. In an embodiment, said impurity may be a fermentation inhibitor.

Also provided is such a method wherein said broth comprises a third bioproduct, said third bioproduct is 3-hydroxybutyric acid, and the molar ratio of the combination of isopropanol and acetone to said third bioproduct is greater than 5.

Also provided is such a method, further comprising separating acetone and isopropanol from said broth to form separated acetone and isopropanol. In an embodiment, said separating comprises evaporation. In an embodiment, said method further comprises catalytically converting said separated acetone and separated isopropanol into at least one acetone or isopropanol derivative.

Also provided is such a method, wherein the method achieves greater production of acetone and isopropanol than the combined amounts of acetone and isopropanol produced by heterotrophic and autotrophic fermentation with the same organism under the same conditions.

Also provided is such a method, wherein said second feedstock comprises CO, $CO_2$, carbonate, bicarbonate, methanol, and mixtures thereof; and wherein the $^{13}C/^{12}C$ isotope ratio of the carbon present in said second feedstock is less than that of atmospheric $CO_2$.

Also provided is such a method, wherein said isopropanol has a $^{13}C/^{12}C$ isotope ratio of less than that of atmospheric $CO_2$.

Also provided is such a method, wherein said first feedstock and said second feedstock are present in the fermentation medium at the same time.

Also provided is such a method, wherein the culturing is performed in whole or in part at a super-atmospheric pressure.

Also provided is such a method, wherein providing a fermentation medium comprises providing said fermentation medium with a mixture of $CO_2$ and hydrogen at a molar ratio in the range between 1:0.1 and 1:5.

Also provided is such a method, comprising production of acetone, isopropanol and acetic acid. For example, in an embodiment, such a method is provided, wherein the amount of acetic acid formed per biomass unit weight is less than about 50% of that formed in autotrophic fermentation with the same organism under the same conditions.

Also provided is such a method, wherein said fermentation medium comprises at least one of CO, $CO_2$, and hydrogen.

Also provided is such a method, wherein said fermentation medium comprises a steel mill produced composition.

Production of Crotyl Alcohol

Provided herein is a method of producing crotyl alcohol, comprising culturing a microbial organism on a growth substrate under conditions to form a broth comprising crotyl alcohol, wherein the microbial organism is capable of converting acetyl-CoA into crotyl alcohol and comprises at least one exogenous nucleic acid encoding one or more of the following crotyl alcohol pathway enzymes:

A. Acetyl-CoA acetyltransferase (also known as thiolase) (THL)
B. 3-hydroxybutyryl-CoA dehydrogenase (HBD)
C. 3-hydroxybutyryl-CoA dehydratase (also known as crotonase) (CRT)
D. Acetaldehyde/alcohol dehydrogenase (ADHE)
E. Butanol dehydrogenase (BDH)
F. CoA-transferase subunit A (COAT-A)
G. CoA-transferase subunit B (COAT-B)
H. Aldehyde:ferredoxin oxidoreductase (AOR), and wherein said microbial organism produces more crotyl alcohol compared with a naturally occurring microbial organism of the same genus and species lacking said exogenous nucleic acid.

Also provided herein is an acetogenic microbial organism or a microbial organism naturally capable of converting acetyl-CoA into crotonyl-CoA, the microbial organism comprising at least one exogenous nucleic acid encoding one or more of the following crotyl alcohol pathway enzymes:

A. Acetyl-CoA acetyltransferase (also known as thiolase) (THL)

B. 3-hydroxybutyryl-CoA dehydrogenase (HBD)

C. 3-hydroxybutyryl-CoA dehydratase (also known as crotonase) (CRT)

D. Acetaldehyde/alcohol dehydrogenase (ADHE)

E. Butanol dehydrogenase (BDH)

F. CoA-transferase subunit A (COAT-A)

G. CoA-transferase subunit B (COAT-B)

H. Aldehyde:ferredoxin oxidoreductase (AOR), wherein said microbial organism produces more crotyl alcohol compared with a naturally occurring microbial organism of the same genus and species lacking said exogenous nucleic acid.

In an embodiment, provided is such a microbial organism, which is capable of converting acetyl-CoA into isopropanol, the microbial organism further comprising at least a second exogenous nucleic acid, the second exogenous nucleic acid encoding one or more isopropanol pathway enzymes. In an embodiment, the one or more isopropanol pathway enzymes comprises: A. THL, F. COAT-A, G. COAT-B, I. ADC, and/or J. secondary alcohol dehydrogenase (SADH). In an embodiment, said microbial organism may comprise exogenous nucleic acids encoding each of the enzymes A, B, C, D, F, G, I, J. In an embodiment, said microbial organism may comprise exogenous nucleic acids encoding each of the enzymes A, B, C, D, E, F, G, I, J. In an embodiment, said microbial organism may comprise exogenous nucleic acids encoding each of the enzymes A, B, C, E, F, G, H, I, J.

In an embodiment, a microbial organism as provided herein may comprise two, three, four, five, six, seven, eight, nine, or ten exogenous nucleic acids.

Also provided herein is such a microbial organism, wherein the exogenous nucleic acid is a heterologous nucleic acid.

Also provided is such a method for further producing acetone, comprising culturing said microbial organism comprising at least one exogenous nucleic acid on a growth substrate to form a broth comprising crotyl alcohol and acetone, wherein said microbial organism is capable of converting acetyl-CoA into acetone, the microbial organism further comprising at least a second exogenous nucleic acid, the second exogenous nucleic acid encoding one or more acetone pathway enzymes. In an embodiment, such a method may be performed, wherein a crotyl alcohol to acetone molar ratio in said broth is in the range from 5 to 10.

Also provided is such a method for further producing isopropanol, comprising culturing said microbial organism comprising at least one exogenous nucleic acid on a growth substrate to form a broth comprising crotyl alcohol and isopropanol, wherein said microbial organism is capable of converting acetyl-CoA into isopropanol, the microbial organism further comprising at least a second exogenous nucleic acid, the second exogenous nucleic acid encoding one or more isopropanol pathway enzymes. In an embodiment, such a method may be performed, wherein a crotyl alcohol to isopropanol molar ratio in said broth is in the range from 5 to 10.

Also provided is such a method, wherein said growth substrate comprises a carbohydrate.

Also provided is such a method, wherein said growth substrate comprises a one-carbon molecule. In an embodiment, such a method may be performed, wherein said one-carbon molecule is exogenously added. In an embodiment, said one-carbon molecule is selected from a group consisting of CO, $CO_2$, $CH_3OH$, carbonate, bicarbonate and combinations thereof.

Also provided is such a method, wherein said growth substrate comprises at least one gaseous compound. In an embodiment, said gaseous compound is exogenously added. In an embodiment, said at least one gaseous compound is selected from a group consisting of CO, $CO_2$, $H_2$ and combinations thereof.

Also provided herein is such a method, wherein said growth substrate comprises a carbohydrate in combination with at least one of a one-carbon molecule and a gaseous compound.

Also provided herein is such a method, wherein said growth substrate comprises a carbohydrate, exogenously added $CO_2$ and exogenously added $H_2$, and wherein at least 2 moles of $H_2$ are added per mole of $CO_2$.

Also provided herein is such a method, comprising steam reforming of a hydrocarbon, whereby $CO_2$ and $H_2$ are formed and used in said growth substrate.

Also provided herein is such a method, wherein carbon yield is at least 42 wt %.

Also provided herein is such a method, comprising providing pressurized $CO_2$, pressurized CO, pressurized $H_2$, or a combination thereof to said growth substrate.

Also provided herein is such a method, wherein said culturing is conducted at a pressure in the range between 1 atm and 5 atm.

Also provided herein is such a method, comprising providing at least one of ammonium carbonate and ammonium bicarbonate to said growth substrate.

Also provided herein is such a method, comprising at least partially separating crotyl alcohol from said broth.

Also provided herein is such a method, comprising at least partially separating acetone from said broth.

Also provided herein is such a method, comprising at least partially separating isopropanol from said broth.

Also provided herein is such a method, wherein said separating comprises liquid-liquid extraction. In an embodiment, the method may further comprise dehydrating said separated crotyl alcohol to form butadiene.

Also provided is such a method, which comprises culturing the microbial organism on a growth substrate for at least 1 hour under conditions to foul' a broth comprising at least 1 g/L crotyl alcohol.

Also provided is such a method, which comprises culturing the microbial organism on a growth substrate for at least 1 hour under conditions to form a broth comprising at least 1 g/L crotyl alcohol and at least 0.1 g/L acetone.

Also provided is such a method, which comprises culturing the microbial organism on a growth substrate for at least 1 hour under conditions to form a broth comprising at least 1 g/L crotyl alcohol and at least 0.1 g/L isopropanol.

Provided herein is also a non-naturally occurring microbial organism capable of converting acetyl-CoA into crotyl alcohol, wherein butyryl-CoA dehydrogenase (BCD) nucleic acid expression and/or BCD protein translation in the microbial organism is disrupted or silenced. In an embodiment, said expression silencing comprises at least one of gene disruption, gene deletion and gene mutation. In an embodiment, said protein translation silencing comprises RNA interference. In an embodiment, such a microbial organism comprises at least one exogenous nucleic acid encoding one or more of the following crotyl alcohol pathway enzymes:

A. Acetyl-CoA acetyltransferase (also known as thiolase) (THL)

B. 3-hydroxybutyryl-CoA dehydrogenase (HBD)

C. 3-hydroxybutyryl-CoA dehydratase (also known as crotonase) (CRT)

D. Acetaldehyde/alcohol dehydrogenase (ADHE)
E. Butanol dehydrogenase (BDH)
F. CoA-transferase subunit A (COAT-A)
G. CoA-transferase subunit B (COAT-B)
H. Aldehyde:ferredoxin oxidoreductase (AOR), wherein said microbial organism produces more crotyl alcohol compared with a naturally occurring microbial organism of the same genus and species lacking said exogenous nucleic acid.

Also provided herein is such a microbial organism, which is capable of converting acetyl-CoA into acetone, the microbial organism further comprising at least one exogenous nucleic acid encoding one or more acetone pathway enzymes. In an embodiment, said one or more acetone pathway enzymes comprises A. THL, F. COAT-A, G. COAT-B, and/or I. acetoacetate decarboxylase (ADC).

Also provided herein is such a microbial organism, which is capable of converting acetyl-CoA into isopropanol, the microbial organism further comprising at least one exogenous nucleic acid encoding one or more isopropanol pathway enzymes. In an embodiment, said one or more isopropanol pathway enzymes comprises: A. THL, F. COAT-A, G. COAT-B, I. ADC, and/or J. secondary alcohol dehydrogenase (SADH).

In an embodiment, said microbial organism may comprise two, three, four, five, six, seven, eight, nine or ten exogenous nucleic acids.

In an embodiment, said microbial organism may comprise exogenous nucleic acids encoding each of the enzymes A, B, C, D, F, G, I. In an embodiment, said microbial organism may comprise exogenous nucleic acids encoding each of the enzymes A, B, C, D, E, F, G, I. In another embodiment, said microbial organism may comprise exogenous nucleic acids encoding each of the enzymes A, B, C, E, F, G, H, I. In another embodiment, said microbial organism may comprise exogenous nucleic acids encoding each of the enzymes A, B, C, D, F, G, I, J.

Also provided herein is such a microbial organism, wherein at least one exogenous nucleic acid is a heterologous nucleic acid.

Also provided herein is such a microbial organism, wherein said organism is an acetogenic bacterium.

Herein is further provided a method of producing crotyl alcohol, comprising culturing a non-naturally occurring microbial organism on a growth substrate under conditions to form a broth comprising crotyl alcohol, wherein the microbial organism is capable of converting acetyl-CoA into crotyl alcohol and wherein butyryl-CoA dehydrogenase (BCD) nucleic acid expression and/or BCD protein translation in the microbial organism is disrupted or silenced.

Utilization of Non-Preferred Carbon Source

According to an embodiment, said organism is acetogenic and said first feedstock comprises at least one non-preferred carbon source, for example, a non-preferred sugar. As used herein, the term non-preferred carbon source refers to a carbon source that is metabolized by the native form of the organism at a rate of less than 0.01 g/hr/g cell mass. Such a carbon source may be a carbohydrate, a sugar (e.g., glucose) or glycerol. Such a non-preferred carbon source may also be methanol. The non-preferred carbon source may also be an oxygen-containing organic compound. According to an embodiment, said non-preferred carbon source comprises at least 50%, at least 60%, at least 70%, at least 80% or at least 90% of said first feedstock. According to an embodiment, the concentration of said non-preferred carbon source in said provided fermentation medium is in a range between 2 g/L and 50 g/L.

According to an embodiment, said non-preferred sugar is selected from the group consisting of glucose, mannose, galactose, arabinose, ribose, maltose, sucrose, lactose, cellobiose, and mixtures thereof. A non-preferred sugar is a sugar that is metabolized by the native form of the organism at a rate of less than 0.01 g/hr/g cell mass. According to an embodiment, said non-preferred sugar comprises glucose. According to an embodiment, said non-preferred sugar forms at least 50%, at least 60%, at least 70%, at least 80% or at least 90% of said first feedstock. According to an embodiment, the concentration of said non-preferred sugar in said provided fermentation medium is in a range between 2 g/L and 50 g/L.

According to an embodiment, said first feedstock further comprises at least one preferred sugar. As used herein, the term preferred sugar refers to a sugar that is metabolized by the native form of the organism at a rate greater than 0.01 g/hr/g cell mass.

According to an embodiment, said preferred sugar is selected from the group consisting of fructose, xylose, and mixtures thereof. According to an embodiment, said provided fermentation medium comprises said preferred sugar and said non-preferred sugar concurrently. According to an embodiment, said provided fermentation medium comprises first said preferred sugar and then said non-preferred sugar.

According to an embodiment, said non-preferred sugar is metabolized at a rate greater than 0.01 g/hr/g cell mass. Metabolism rates of a non-preferred sugar of greater than 0.01 g/hr/g cell mass may be achieved by an organism that has been genetically modified for increased non-preferred sugar metabolism. In an embodiment, said non-preferred sugar may be metabolized by a genetically modified organism at a rate greater than 0.02 g/hr/g, greater than 0.04 g/hr/g cell mass, greater than 0.06 g/hr/g, greater than 0.08 g/hr/g cell mass, greater than 0.1 g/hr/g, greater than 0.12 g/hr/g cell mass, greater than 0.14 g/hr/g, greater than 0.16 g/hr/g cell mass, greater than 0.18 g/hr/g, greater than 0.2 g/hr/g cell mass, or greater than 0.26 g/hr/g.

According to an embodiment, $CO_2$ is generated from metabolism of said non-preferred sugar and said generated $CO_2$ comprises at least a fraction of said fermentation medium second feedstock. According to an embodiment, said generated $CO_2$ comprises at least 20% of said fermentation medium second feedstock, at least 40%, at least 60%, at least 80% or at least 90%.

According to an embodiment, said acetogenic organism metabolizing said non-preferred sugar is acetogenic *Clostridia*. According to an embodiment, said organism metabolizing said non-preferred sugar is selected from the group consisting of *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Clostridium carboxidivorans, Alkalibaculum bacchi, Clostridium drakei, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxobacter pfennigii,* and *Thermoanaerobacter kivui.*

According to an embodiment, said organism metabolizing said non-preferred sugar is genetically modified to express at least one component of a phosphotransferase system (PTS), also known as PEP group translocation. According to an embodiment, said at least one component is selected from the group consisting of enzymes EIIA, EIIB, EIIC, and combinations thereof.

According to an embodiment, said organism is genetically modified to express a gene related to a sugar transport system other than genes associated with the phosphotransferase system. According to an embodiment, said organism may be genetically modified to express a gene selected from the group consisting of a symporter system utilizing a sodium ion (Na⁺), a symporter system utilizing protons (H⁺), a permease system, and a combination thereof. For example, the organism may be transformed with a Gnt-II system transporter (gntP gene), a glycoside-pentoside-hexuronide (GPH):cation symporter family gene (GPH gene) or a fucose-galactose-glucose (FGH):H⁺ symporter family gene (FGH gene).

The sugar transport system is not particularly limited. For example, in an embodiment, said gntP gene may be obtained from one or more various organisms including *Clostridium acetobutylicum* ATCC 824 and *Escherichia coli* K-12. An exemplary nucleic acid sequence that encodes a gntP gene, from *C. acetobutylicum*, is as follows:

(SEQ ID NO: 5)
```
ATGCCATTATTAATTGTTGTTATTGGCGTCGCATTACTATTACTACTTAT
GATTAAATTCAAAGTAAACGGATTCATATCCCTAATTCTTGTAGCTTTGG
TTGTTGGTATCGCCGAAGGTATGAATCCTGCAAAAGCTGTTTCTTCAATT
CAAAACGGTGTTGGAAGCACCTTAAGCAGTTTGGCACTAATTTTAGGTTT
TGGTGCTATGTTTGGAAAATTAATAGCTGATTCTGGTGCTGCTCAAAGGA
TTTCTAGAAGTTTAATTAATAAATTTGGTGTAAAAAAAATTCAATGGGCT
GTTGTATTAACGGGTTTCATAGTTGGCATTGCTATGTTCTATGAGGTAGG
TTTTGTTCTACTTATACCTCTTGTTTTTACTATTGCTGAATTCACAGAAC
TTCCTCTTTTATACATAGGCGTTCCTATGGCTGCAGCTTTATCTGTCACT
CACGGATTTTTACCTCCTCACCCTGGACCTGTTGCAATAGCTACAATATA
TGGTGCAAGCATTAGCATGACTCTTGTATATGGAATTGTAATAGCTATAC
CTACAGTAATAGTTGCAGGACCTGTTTTGACTAAGTTTTTAAAACGTTTT
GATCATAAATCTTCAAAAAACCTTTTTAAAACTAAGGTCTTTGATGAAGA
TGAAATGCCAAGTTTCTCATTAAGCGTATTAACTGCTATTGTTCCTCCTA
TTCTTATGGCCTTTTCAGCTGTTTGTGAAATCACACTACCAAAAACATCT
CCTATAAGACATTTTGCAGAATTCGTTGGAAGTCCTATGATGGCAATGTT
TATATCAATCATTGTAGCTATCTTTACTCTTGGTATAATGCGCGGAAAGA
AAATGGAAGAAATAATGAGAACTTTAGCTGAAGCCGCAAGTTCCATTGCA
ATGATCCTTTTAATAGTAGCTGGAGGTGGTGCCTTCAAGCAAGTACTAAT
AGACAGTGGTGTTGGAAAATATATCGCTTCTATTATGGTTGGAAGTAATA
TATCTCCTCTAATCTTGGCTTGGGCGATTGCAGCAATTTTAAGATTATCT
CTTGGTTCTGCCACTGTTTCTGCTATGACTACTGCCGGTATAGTACTTCC
TCTTATTCCTTCAACCCATGCAAACCCAGCATTAATGGTTTTAGCAACTG
GCGCAGGTAGTCTTATTTTCTCTCATGTAAACGATCCAGGTTTCTGGATG
TTCAAAGAATATTTGGACTTAGCATAGGAGAAACAATGGCTTCATGGTC
TACTTTAGAAACTATAATTTCAATTATGGGGTTAATTGGTGTTTTAGCTT
TAAATATGGTTGGATAG.
```

The encoded gntP amino acid sequence is as follows:

(SEQ ID NO: 6)
```
MPLLIVVIGVALLLLLMIKFKVNGFISLILVALVVGIAEGMNPAKAVSSI
QNGVGSTLSSLALILGFGAMFGKLIADSGAAQRISRSLINKFGVKKIQWA
VVLTGFIVGIAMFYEVGFVLLIPLVFTIAEFTELPLLYIGVPMAAALSVT
HGFLPPHPGPVAIATIYGASISMTLVYGIVIAIPTVIVAGPVLTKFLKRF
DHKSSKNLFKTKVFDEDEMPSFSLSVLTAIVPPILMAFSAVCEITLPKTS
PIRHFAEFVGSPMMAMFISIIVAIFTLGIMRGKKMEEIMRTLAEAASSIA
MILLIVAGGGAFKQVLIDSGVGKYIASIMVGSNISPLILAWAIAAILRLS
LGSATVSAMTTAGIVLPLIPSTHANPALMVLATGAGSLIFSHVNDPGFWM
FKEYFGLSIGETMASWSTLETIISIMGLIGVLALNMVG.
```

In an embodiment, an exemplary gntP amino acid sequence may be an amino acid sequence which has at least 75%, 80%, 85%, 90%, 91%, 92%, 93%, 94%, 95%, 96%, 97%, 98%, or 99% identity to the above sequence, and which is capable of transporting gluconate or glucose. In an embodiment, the corresponding gntP polynucleotide sequence may be a polynucleotide sequence encoding an amino acid sequence which has at least 75%, 80%, 85%, 90%, 91%, 92%, 93%, 94%, 95%, 96%, 97%, 98%, or 99% identity to the above sequence. The corresponding GPH polynucleotide sequence may also be a sequence which is 75%, 80%, 85%, 90%, 91%, 92%, 93%, 94%, 95%, 96%, 97%, 98%, or 99% identical to the above GPH polynucleotide sequence.

An exemplary nucleic acid sequence that encodes a GPH gene, from *C. acetobutylicum*, is as follows:

(SEQ ID NO: 7)
```
ATGAAAAAGTTAAGCTTAAAGGAAAAAATCTCTTATGGACTTGGCGATTT
TGGAAATGGTTTCATGTTTGATTTGGGTCAATCATATCTGTTAAAATTCT
ATACAGACGTCGTAGGTATAGCTGCAGGAGCGGCGGGAGGAATATTCTTC
TTCACTAAAATATTTGATGCTTTCATGGATCCTATAGCTGGAACAATAAT
AGATTCAAGGAAACCAGGTAAAAACGGTAAATTCAAACCTATTATGTTCT
TTGCAAGTATAGTACTTGCTATATTGACAGTAATAACGTTTACTAACCCT
GGAAAAACTGCTACATCAAAACTATTATTTGCATATGCAACATATATGAT
ATGGGGACTTGGATACTCATTTACAAATGTTCCGTATGGATCTCTTGGAT
CAGTTATAACTCAAGATGTTCAAGAAAGAACTTCGTTGGCGACTTTTAGA
CAGATAGGTTCTTCAGGAGCTCTTCTTATAACAAGTGTTATATTTATGCC
TCTTGTTTTAGTATTTCATAACCCAGCAATAGGTTATCCAGTAGTTGCGG
GTATAATGGGGTTAATAGGAATATTATCATTCTACATGACATACAAAAAT
ACTAGAGAAGTTGTTGCGCCAGCTGAAAACGTTAAGAAGGAAAAAATAAC
ACCAAAGTCAATTGCGGTTACAATATTTACAAATAGAGCATTATTAACAT
TAATATTAATGACTATATTCTCTATTTCGGCTTACAATATTAGAAGTTCA
TTAATTGTTTATTACTGCCAATATAATCTTGGAAACGTTACTTTATTACC
ATATATAAATTTCTTCACTATAGGATGTGCTGTTTTAGGTGTTTCTTTCA
TGCCAAAGCTAGTTGGTAGATTTGGTAAAAAAGAACTGCTATCATAGGA
```

-continued
TTTTTGATAAGTGTTATTGCAGATAGTATAAACTTTCTTCTTCCAGGAAA

TATATATACTTTCACAATATTATTAGCAATTGGATTTATAGGTATAAGCA

TTCCTAATGGAATAACTTGGGCTTTTGTATCAGACAGTATCGATTATGGT

GAGTGGAGAACAGGAACTAGAAGAGAAGGAATAACTTACTCTGTATTTAA

TTTCGCAAGAAAACTTGCTCAGTCAATAGCTGGATTATTATCAGGATGGG

GACTTGGATTTGTTGGTTATGTAGCTAACAAGAAACAAAGTGCACATGCA

TTATTTGGAATAAAAGCATTATTGATGGCTTATCCAGCGGTAGCGCTTTT

AGTAGCAGCATTAATAATTGGTTTATTGTACAACCTTTCAGATAAGAAAT

TTACTGAAATAATAGAAGAATTAGACGCTAGAAAAGGTAAAACAGTTTA

A.

The encoded GPH amino acid sequence is as follows:

(SEQ ID NO: 8)
MKKLSLKEKISYGLGDFGNGFMFDLGQSYLLKFYTDVVGIAAGAAGGIFF

FTKIFDAFMDPIAGTIIDSRKPGKNGKFKPIMFFASIVLAILTVITFTNP

GKTATSKLLFAYATYMIWGLGYSFTNVPYGSLGSVITQDVQERTSLATFR

QIGSSGALLITSVIFMPLVLVFHNPAIGYPVVAGIMGLIGILSFYMTYKN

TREVVAPAENVKKEKITPKSIAVTIFTNRALLTLILMTIFSISAYNIRSS

LIVYYCQYNLGNVTLLPYINFFTIGCAVLGVSFMPKLVGRFGKKRTAIIG

FLISVIADSINFLLPGNIYTFTILLAIGFIGISIPNGITWAFVSDSIDYG

EWRTGTRREGITYSVFNFARKLAQSIAGLLSGWGLGFVGYVANKKQSAHA

LFGIKALLMAYPAVALLVAALIIGLLYNLSDKKFTEIIEELDARKGKTV.

In an embodiment, an exemplary GPH amino acid sequence may be an amino acid sequence which has at least 75%, 80%, 85%, 90%, 91%, 92%, 93%, 94%, 95%, 96%, 97%, 98%, or 99% identity to the above sequence, and which is capable of transporting glucose. In an embodiment, the corresponding GPH polynucleotide sequence may be a polynucleotide sequence encoding an amino acid sequence which has at least 75%, 80%, 85%, 90%, 91%, 92%, 93%, 94%, 95%, 96%, 97%, 98%, or 99% identity to the above sequence. The corresponding GPH polynucleotide sequence may also be a sequence which is 75%, 80%, 85%, 90%, 91%, 92%, 93%, 94%, 95%, 96%, 97%, 98%, or 99% identical to the above GPH polynucleotide sequence.

An exemplary nucleic acid sequence that encodes an FGH gene, from *E. coli*, is as follows:

(SEQ ID NO: 9)
ATGGGAAACACATCAATACAAACGCAGAGTTACCGTGCGGTAGATAAAGA

TGCAGGGCAAAGCAGAAGTTACATTATTCCATTCGCGCTGCTGTGCTCAC

TGTTTTTTCTTTGGCGGTAGCCAATAACCTTAACGACATTTTATTACCT

CAATTCCAGCAGGCTTTTACGCTGACAAATTTCCAGGCTGGCCTGATCCA

ATCGGCCTTTTACTTTGGTTATTTCATTATCCCAATCCCTGCTGGGATAT

TCATGAAAAACTCAGTTATAAAGCAGGGATTATTACCGGGTTATTTTTA

TATGCCTTGGGTGCTGCATTATTCTGGCCCGCCGCAGAAATAATGAACTA

CACCTTGTTTTTAGTTGGCCTATTTATTATTGCAGCCGGATTAGGTTGTC

TGGAAACTGCCGCAAACCCTTTTGTTACGGTATTAGGGCCGGAAAGTAGT

GGTCACTTCCGCTTAAATCTTGCGCAAACATTTAACTCGTTTGGCGCAAT

TATCGCGGTTGTCTTTGGGCAAAGTCTTATTTTGTCTAACGTGCCACATC

AATCGCAAGACGTTCTCGATAAAATGTCTCCAGAGCAATTGAGTGCGTAT

AAACACAGCCTGGTATTATCGGTACAGACACCTTATATGATCATCGTGGC

TATCGTGTTACTGGTCGCCCTGCTGATCATGCTGACGAAATTCCCGGCAT

TGCAGAGTGATAATCACAGTGACGCCAAACAAGGATCGTTCTCCGCATCG

CTTTCTCGCCTGGCGCGTATTCGCCACTGGCGCTGGGCGGTATTAGCGCA

ATTCTGCTATGTCGGCGCACAAACGGCCTGCTGGAGCTATTTGATTCGCT

ACGCTGTAGAAGAAATTCCAGGTATGACTGCAGGCTTTGCCGCTAACTAT

TTAACCGGAACCATGGTGTGCTTCTTTATTGGTCGTTTCACCGGTACCTG

GCTCATCAGTCGCTTCGCACCACACAAAGTCCTGGCCGCCTACGCATTAA

TCGCTATGGCACTGTGCCTGATCTCAGCCTTCGCTGGCGGTCATGTGGGC

TTAATAGCCCTGACTTTATGCAGCGCCTTTATGTCGATTCAGTACCCAAC

AATCTTCTCGCTGGGCATTAAGAATCTCGGCCAGGACACCAAATATGGTT

CGTCCTTCATCGTTATGACCATTATTGGCGGCGGTATTGTCACTCCGGTC

ATGGGTTTTGTCAGTGACGCGGCGGGCAACATCCCCACTGCTGAACTGAT

CCCCGCACTCTGCTTCGCGGTCATCTTTATCTTTGCCCGTTTCCGTTCTC

AAACGGCAACTAACTGA.

The encoded FGH amino acid sequence is as follows:

(SEQ ID NO: 10)
MGNTSIQTQSYRAVDKDAGQSRSYIIPFALLCSLFFLWAVANNLNDI

LLPQFQQAFTLTNFQAGLIQSAFYFGYFIIPIPAGILMKKLSYKAGI

ITGLFLYALGAALFWPAAEIMNYTLFLVGLFIIAAGLGCLETAANPF

VTVLGPESSGHFRLNLAQTFNSFGAIIAVVFGQSLILSNVPHQSQDV

LDKMSPEQLSAYKHSLVLSVQTPYMIIVAIVLLVALLIMLTKFPALQ

SDNHSDAKQGSFSASLSRLARIRHWRWAVLAQFCYVGAQTACWSYLI

RYAVEEIPGMTAGFAANYLTGTMVCFFIGRFTGTWLISRFAPHKVLA

AYALIAMALCLISAFAGGHVGLIALTLCSAFMSIQYPTIFSLGIKNL

GQDTKYGSSFIVMTIIGGGIVTPVMGFVSDAAGNIPTAELIPALCFA

VIFIFARFRSQTATN.

In an embodiment, an exemplary FGH amino acid sequence may be an amino acid sequence which has at least 75%, 80%, 85%, 90%, 91%, 92%, 93%, 94%, 95%, 96%, 97%, 98%, or 99% identity to the above sequence, and which is capable of transporting glucose. In an embodiment, the corresponding FGH polynucleotide sequence may be a polynucleotide sequence encoding an amino acid sequence which has at least 75%, 80%, 85%, 90%, 91%, 92%, 93%, 94%, 95%, 96%, 97%, 98%, or 99% identity to the above sequence. The corresponding FGH polynucleotide sequence may also be a sequence which is 75%, 80%, 85%, 90%, 91%, 92%, 93%, 94%, 95%, 96%, 97%, 98%, or 99% identical to the above FGH polynucleotide sequence.

According to an embodiment, said organism metabolizing said non-preferred sugar expresses genes of the Wood-Ljungdahl pathway.

According to an embodiment, said organism metabolizing said non-preferred sugar is genetically modified to have a primary alcohol dehydrogenase gene or a secondary alcohol dehydrogenase gene deleted from its genome.

According to an embodiment, said organism metabolizing said non-preferred sugar is genetically modified to have butanediol dehydrogenase deleted from its genome.

According to an embodiment, the rate of metabolizing said non-preferred sugar by said genetically modified organism is greater than that of metabolizing said non-preferred sugar by the native form of the organism by a factor of at least 1.5, at least 2, at least 5, at least 8, at least 10, at least 12, at least 15, or at least 20.

According to an embodiment, culturing said organism in said non-preferred sugar comprising fermentation medium, forms a fermentation broth comprising a bioproduct selected from the group consisting of even numbered primary alcohols, odd numbered secondary alcohols, organic acids of less than 7 carbons, C3 compounds, C4 compounds, and mixtures thereof.

According to an embodiment, culturing said organism in said non-preferred sugar comprising fermentation medium, forms a fermentation broth comprising a bioproduct selected from the group consisting of acetic acid, propionic acid, 3-hydroxypropionic acid, butyric acid, hexanoic acid, 3-hydroxybutyric acid, crotonic acid, acetoacetic acid, lactic acid, 2-hydroxyisobutyric acid, 3-methylbutanoic acid, ethanol, butanol, crotyl alcohol, hexanol, acetone, isopropanol, 2,3-butanediol, acetoin, 1,3-propanediol and combinations thereof.

According to an embodiment, culturing said organism in said non-preferred sugar comprising fermentation medium, foul's a fermentation broth comprising a non-naturally occurring bioproduct.

According to an embodiment, culturing said organism in said non-preferred sugar comprising fermentation medium achieves greater production of the at least one bioproduct than the combined amounts produced by heterotrophic and autotrophic fermentation with the same organism under the same conditions.

According to an embodiment, in culturing said organism in said non-preferred sugar comprising fermentation medium, the carbon yield, based on the total amount of carbon in produced bioproducts divided by the total amount of carbon metabolized in said first feedstock, is at least 50%, at least 60%, at least 70%, at least 80%, at least 90%, at least 100%, at least 110%, at least 120%, at least 130%, at least 140%, at least 150%, or at least 160%.

According to an embodiment, providing a non-preferred sugar comprising fermentation medium includes providing said fermentation medium with a mixture of $CO_2$ and hydrogen at a molar ratio in the range from 1:0.1 to 1:5.

In an embodiment, provided herein is a mixotrophic fermentation method comprising (i) providing an isolated naturally acetogenic organism, (ii) providing a first feedstock and a second feedstock wherein said first feedstock comprises a carbon source that is metabolized by the native form of the organism at a rate of less than 0.01 g/hr/g cell mass; and wherein said second feedstock comprises CO, $CO_2$, carbonate, bicarbonate, $H_2$, glycerol, methanol, formate, urea or a combination thereof; and (iii) culturing said organism in a fermentation medium, whereby both feedstocks are metabolized and a fermentation broth is formed, which broth comprises at least one bioproduct.

In an embodiment, the method may comprise production of at least one bioproduct and acetic acid as a second bioproduct, wherein the amount of acetic acid formed per biomass unit weight is less than about 50% of that formed in autotrophic fermentation with the same organism under the same conditions.

In an embodiment, the carbon yield, based on the total amount of carbon in produced bioproducts divided by the total amount of carbon metabolized from said first feedstock, is at least 50%.

In an embodiment, the $^{13}C/^{12}C$ isotope ratio of the carbon present in the bioproduct may be less than that of atmospheric $CO_2$.

In an embodiment, said carbon source may be selected from carbohydrates, glycerol, methanol, or a combination thereof.

In embodiment, said organism may be *Clostridia*.

In an embodiment, said organism may be genetically modified.

In an embodiment, said first feedstock and said second feedstock may be present in the fermentation medium at the same time.

In an embodiment, said fermentation medium may comprise a carbohydrate and at least one of CO, $CO_2$, and hydrogen.

In an embodiment, said fermentation medium may comprise a steel mill produced CO composition.

In an embodiment, the culturing may be performed in whole or in part at a super-atmospheric pressure.

In an embodiment, said bioproduct may be selected from the group consisting of even numbered primary alcohols, odd numbered secondary alcohols, organic acids of less than 7 carbons, C3 compounds, C4 compounds, and mixtures thereof.

In an embodiment, said bioproduct may be selected from the group consisting of acetic acid, acetone, propionic acid, butyric acid, hexanoic acid, 3-hydroxypropionic acid, 3-hydroxybutyric acid, crotonic acid, acetoacetic acid, lactic acid, 2-hydroxyisobutyric acid, 3-methylbutanoic acid, ethanol, butanol, crotyl alcohol, hexanol, acetone, isopropanol, 2,3-butanediol, acetoin, 1,3-propanediol, and combinations thereof.

In an embodiment, said bioproduct may be non-naturally occurring.

In an embodiment, said broth may comprise a first bioproduct and a second bioproduct, wherein said first bioproduct is selected from the group consisting of acetoacetic acid, acetone, isopropanol, 3-hydroxybutyric acid, 2-hydroxyisobutyric acid, and combinations thereof, said second bioproduct is selected from the group consisting of ethanol, butanol, crotyl alcohol, hexanol, and combinations thereof, and the molar ratio between said first bioproduct and said second bioproduct is in the range from 0.1 to 0.95.

In an embodiment, the second feedstock may comprise CO, $CO_2$, carbonate, bicarbonate, methanol, or a combination thereof; and the $^{13}C/^{12}C$ isotope ratio of the carbon present in said second feedstock may be less than that of atmospheric $CO_2$.

In an embodiment, the method may comprise providing said fermentation medium with a mixture of $CO_2$ and hydrogen at a molar ratio in the range from 1:0.1 to 1:5.

In an embodiment, the method may further comprise steam reforming of a hydrocarbon to form said mixture of $CO_2$ and hydrogen.

In an embodiment, the first feedstock may comprise a sugar selected from glucose and sucrose, and the organism may metabolize $CO_2$ produced during glycolysis.

In an embodiment, the first feedstock may comprise a sugar selected from glucose and sucrose, the second feedstock may comprise at least one of fl, and methanol, and the organism may metabolize $CO_2$ produced during glycolysis.

In an embodiment, said at least one bioproduct is acetone. In such an embodiment, the first feedstock may comprise a sugar selected from glucose and sucrose, and the organism may metabolize $CO_2$ produced during glycolysis.

In an embodiment, said at least one bioproduct is butyric acid. In such an embodiment, the first feedstock may comprise a sugar selected from glucose and sucrose, and the organism may metabolize $CO_2$ produced during glycolysis.

In an embodiment, said at least one bioproduct is isopropanol. In such an embodiment, the first feedstock may comprise a sugar selected from glucose and sucrose, and methanol, and the organism may metabolize $CO_2$ produced during glycolysis.

In an embodiment, the metabolizing of the first feedstock does not inhibit the metabolizing of the second feedstock. In such a case, inhibition is defined as a decrease in the metabolizing rate of the second feedstock in the presence of the first feedstock compared to the metabolizing rate of the second feedstock in the absence of the first feedstock. In an embodiment, the first feedstock may inhibit the metabolizing of the second feedstock by less than 10%. In an embodiment, the first feedstock may inhibit the metabolizing of the second feedstock by less than 1%, less than 5%, less than 15%, less than 20%, or less than 30%.

In an embodiment, the first feedstock may comprise a non-preferred sugar and the second feedstock may comprise CO, $CO_2$, carbonate, bicarbonate, $H_2$, glycerol, methanol, formate, urea or a combination thereof.

Additional Exemplary Polynucleotide and Amino Acids Sequences

Exemplary amino acid and nucleic acid sequences for performing methods are disclosed herein.

An exemplary acetyl-CoA acetyltransferase (also known as thiolase) (THL) for use in the present invention catalyzes the condensation of two (2) acetyl-CoA molecules into acetoacetyl-CoA and the release of one (1) coenzyme-A (CoA) molecule. Exemplary THL nucleic acid and amino acid sequences (from *C. acetobutylicum* ATCC 824) are set forth below:

EC number: 2.3.1.9
Example Nucleic Acid Sequence:

```
                                          (SEQ ID NO: 11)
ATGAAAGAAGTTGTAATAGCTAGTGCAGTAAGAACAGCGATTGGATC

TTATGGAAAGTCTCTTAAGGATGTACCAGCAGTAGATTTAGGAGCTA

CAGCTATAAAGGAAGCAGTTAAAAAAGCAGGAATAAAACCAGAGGAT

GTTAATGAAGTCATTTTAGGAAATGTTCTTCAAGCAGGTTTAGGACA

GAATCCAGCAAGACAGGCATCTTTTAAAGCAGGATTACCAGTTGAAA

TTCCAGCTATGACTATTAATAAGGTTTGTGGTTCAGGACTTAGAACA

GTTAGCTTAGCAGCACAAATTATAAAAGCAGGAGATGCTGACGTAAT

AATAGCAGGTGGTATGGAAAATATGTCTAGAGCTCCTTACTTAGCGA

ATAACGCTAGATGGGGATATAGAATGGGAAACGCTAAATTTGTTGAT

GAAATGATCACTGACGGATTGTGGGATGCATTTAATGATTACCACAT

GGGAATAACAGCAGAAAACATAGCTGAGAGATGGAACATTTCAAGAG

AAGAACAAGATGAGTTTGCTCTTGCATCACAAAAAAAGCTGAAGAA

GCTATAAAATCAGGTCAATTTAAAGATGAAATAGTTCCTGTAGTAAT
```

-continued
```
TAAAGGCAGAAAGGGAGAAACTGTAGTTGATACAGATGAGCACCCTA

GATTTGGATCAACTATAGAAGGACTTGCAAAATTAAAACCTGCCTTC

AAAAAAGATGGAACAGTTACAGCTGGTAATGCATCAGGATTAAATGA

CTGTGCAGCAGTACTTGTAATCATGAGTGCAGAAAAAGCTAAAGAGC

TTGGAGTAAAACCACTTGCTAAGATAGTTTCTTATGGTTCAGCAGGA

GTTGACCCAGCAATAATGGGATATGGACCTTTCTATGCAACAAAAGC

AGCTATTGAAAAAGCAGGTTGGACAGTTGATGAATTAGATTTAATAG

AATCAAATGAAGCTTTTGCAGCTCAAAGTTTAGCAGTAGCAAAAGAT

TTAAAATTTGATATGAATAAAGTAAATGTAAATGGAGGAGCTATTGC

CCTTGGTCATCCAATTGGAGCATCAGGTGCAAGAATACTCGTTACTC

TTGTACACGCAATGCAAAAAAGAGATGCAAAAAAAGGCTTAGCAACT

TTATGTATAGGTGGCGGACAAGGAACAGCAATATTGCTAGAAAAGTG

CTAG
```

Example Amino Acid Sequence:

```
                                          (SEQ ID NO: 12)
MKEVVIASAVRTAIGSYGKSLKDVPAVDLGATAIKEAVKKAGIKPED

VNEVILGNVLQAGLGQNPARQASFKAGLPVEIPAMTINKVCGSGLRT

VSLAAQIIKAGDADVIIAGGMENMSRAPYLANNARWGYRMGNAKFVD

EMITDGLWDAFNDYHMGITAENIAERWNISREEQDEFALASQKKAEE

AIKSGQFKDEIVPVVIKGRKGETVVDTDEHPRFGSTIEGLAKLKPAF

KKDGTVTAGNASGLNDCAAVLVIMSAEKAKELGVKPLAKIVSYGSAG

VDPAIMGYGPFYATKAAIEKAGWTVDELDLIESNEAFAAQSLAVAKD

LKFDMNKVNVNGGAIALGHPIGASGARILVTLVHAMQKRDAKKGLAT

LCIGGGQGTAILLEKC
```

An exemplary 3-hydroxybutyryl-CoA dehydrogenase (HBD) for use in the present invention catalyzes the conversion of acetoacetyl-CoA into 3-hydroxybutyryl-CoA. 3-Hydroxybutyryl-CoA can be either the (S) or the (R) enantiomer. This reaction typically requires a coenzyme, such as NADH or NADPH. Exemplary HBD nucleic acid and amino acid sequences (from *C. acetobutylicum* ATCC 824) are set forth below:

EC number: 1.1.1.36 or 1.1.1.35 or 1.1.1.157
Example Nucleic Acid Sequence:

```
                                          (SEQ ID NO: 13)
ATGAAAAAGGTATGTGTTATAGGTGCAGGTACTATGGGTTCAGGAAT

TGCTCAGGCATTTGCAGCTAAAGGATTTGAAGTAGTATTAAGAGATA

TTAAAGATGAATTTGTTGATAGAGGATTAGATTTTATCAATAAAAAT

CTTTCTAAATTAGTTAAAAAAGGAAAGATAGAAGAAGCTACTAAAGT

TGAAATCTTAACTAGAATTTCCGGAACAGTTGACCTTAATATGGCAG

CTGATTGCGATTTAGTTATAGAAGCAGCTGTTGAAAGAATGGATATT

AAAAAGCAGATTTTTGCTGACTTAGACAATATATGCAAGCCAGAAAC

AATTCTTGCATCAAATACATCATCACTTTCAATAACAGAAGTGGCAT
```

-continued
CAGCAACTAAAAGACCTGATAAGGTTATAGGTATGCATTTCTTTAAT

CCAGCTCCTGTTATGAAGCTTGTAGAGGTAATAAGAGGAATAGCTAC

ATCACAAGAAACTTTTGATGCAGTTAAAGAGACATCTATAGCAATAG

GAAAAGATCCTGTAGAAGTAGCAGAAGCACCAGGATTTGTTGTAAAT

AGAATATTAATACCAATGATTAATGAAGCAGTTGGTATATTAGCAGA

AGGAATAGCTTCAGTAGAAGACATAGATAAAGCTATGAAACTTGGAG

CTAATCACCCAATGGGACCATTAGAATTAGGTGATTTTATAGGTCTT

GATATATGTCTTGCTATAATGGATGTTTTATACTCAGAAACTGGAGA

TTCTAAGTATAGACCACATACATTACTTAAGAAGTATGTAAGAGCAG

GATGGCTTGGAAGAAAATCAGGAAAAGGTTTCTACGATTATTCAAAA

TAA

Example Amino Acid Sequence:

(SEQ ID NO: 14)
MKKVCVIGAGTMGSGIAQAFAAKGFEVVLRDIKDEFVDRGLDFINKN

LSKLVKKGKIEEATKVEILTRISGTVDLNMAADCDLVIEAAVERMDI

KKQIFADLDNICKPETILASNTSSLSITEVASATKRPDKVIGMHFFN

PAPVMKLVEVIRGIATSQETFDAVKETSIAIGKDPVEVAEAPGFVVN

RILIPMINEAVGILAEGIASVEDIDKAMKLGANHPMGPLELGDFIGL

DICLAIMDVLYSETGDSKYRPHTLLKKYVRAGWLGRKSGKGFYDYSK

An exemplary 3-hydroxybutyryl-CoA dehydratase (also known as crotonase) (CRT) for use in the present invention catalyzes the dehydration of 3-hydroxybutyryl-CoA into crotonyl-CoA and a water molecule. It can act upon either the (S) or the (R) enantiomer of 3-hydroxybutyryl-CoA. Exemplary CRT nucleic acid and amino acid sequences (from C. acetobutylicum ATCC 824) are set forth below:
EC number: 4.2.1.17 or 4.2.1.55
Example Nucleic Acid Sequence:

(SEQ ID NO: 15)
ATGGAACTAAACAATGTCATCCTTGAAAAGGAAGGTAAAGTTGCTGT

AGTTACCATTAACAGACCTAAAGCATTAAATGCGTTAAATAGTGATA

CACTAAAAGAAATGGATTATGTTATAGGTGAAATTGAAAATGATAGC

GAAGTACTTGCAGTAATTTTAACTGGAGCAGGAGAAAAATCATTTGT

AGCAGGAGCAGATATTTCTGAGATGAAGGAAATGAATACCATTGAAG

GTAGAAAATTCGGGATACTTGGAAATAAAGTGTTTAGAAGATTAGAA

CTTCTTGAAAAGCCTGTAATAGCAGCTGTTAATGGTTTTGCTTTAGG

AGGCGGATGCGAAATAGCTATGTCTTGTGATATAAGAATAGCTTCAA

GCAACGCAAGATTTGGTCAACCAGAAGTAGGTCTCGGAATAACACCT

GGTTTTGGTGGTACACAAAGACTTTCAAGATTAGTTGGAATGGGCAT

GGCAAAGCAGCTTATATTTACTGCACAAAATATAAAGGCAGATGAAG

CATTAAGAATCGGACTTGTAAATAAGGTAGTAGAACCTAGTGAATTA

ATGAATACAGCAAAAGAAATTGCAAACAAAATTGTGAGCAATGCTCC

AGTAGCTGTTAAGTTAAGCAAACAGGCTATTAATAGAGGAATGCAGT

-continued
GTGATATTGATACTGCTTTAGCATTTGAATCAGAAGCATTTGGAGAA

TGCTTTTCAACAGAGGATCAAAAGGATGCAATGACAGCTTTCATAGA

GAAAAGAAAAATTGAAGGCTTCAAAAATAGATAG

Example Amino Acid Sequence:

(SEQ ID NO: 16)
MELNNVILEKEGKVAVVTINRPKALNALNSDTLKEMDYVIGEIENDS

EVLAVILTGAGEKSFVAGADISEMKEMNTIEGRKFGILGNKVFRRLE

LLEKPVIAAVNGFALGGGCEIAMSCDIRIASSNARFGQPEVGLGITP

GFGGTQRLSRLVGMGMAKQLIFTAQNIKADEALRIGLVNKVVEPSEL

MNTAKEIANKIVSNAPVAVKLSKQAINRGMQCDIDTALAFESEAFGE

CFSTEDQKDAMTAFIEKRKIEGFKNR

An exemplary acetaldehyde/alcohol dehydrogenase (ADHE) for use in the present invention is a bifunctional enzyme that catalyzes two reactions sequentially. The first reaction is a CoA-acylating reaction in which crotonyl-CoA is converted into crotonaldehyde. The second reaction is a dehydrogenase reaction in which crotonaldehyde is converted into crotyl alcohol. Any similar substrates can also be used, such as acetyl-CoA, butyryl-CoA, and others. This reaction typically requires a coenzyme, such as NADH or NADPH. Exemplary ADHE nucleic acid and amino acid sequences (from C. acetobutylicum ATCC 824) are set forth below:
EC number: For the first reaction (1.2.1.10 or 1.2.1.57); for the second reaction (1.1.1.1)
Example Nucleic Acid Sequence:

(SEQ ID NO: 17)
ATGAAAGTCACAACAGTAAAGGAATTAGATGAAAAACTCAAGGTAAT

TAAAGAAGCTCAAAAAAAATTCTCTTGTTACTCGCAAGAAATGGTTG

ATGAAATCTTTAGAAATGCAGCAATGGCAGCAATCGACGCAAGGATA

GAGCTAGCAAAAGCAGCTGTTTTGGAAACCGGTATGGGCTTAGTTGA

AGACAAGGTTATAAAAAATCATTTTGCAGGCGAATACATCTATAACA

AATATAAGGATGAAAAAACCTGCGGTATAATTGAACGAAATGAACCC

TACGGAATTACAAAAATAGCAGAACCTATAGGAGTTGTAGCTGCTAT

AATCCCTGTAACAAACCCCACATCAACAACAATATTTAAATCCTTAA

TATCCCTTAAAACTAGAAATGGAATTTTCTTTTCGCCTCACCCAAGG

GCAAAAAAATCCACAATACTAGCAGCTAAAACAATACTTGATGCAGC

CGTTAAGAGTGGTGCCCCGGAAAATATAATAGGTTGGATAGATGAAC

CTTCAATTGAACTAACTCAATATTTAATGCAAAAAGCAGATATAACC

CTTGCAACTGGTGGTCCCTCACTAGTTAAATCTGCTTATTCTTCCGG

AAAACCAGCAATAGGTGTTGGTCCGGGTAACACCCCAGTAATAATTG

ATGAATCTGCTCATATAAAAATGGCAGTAAGTTCAATTATATTATCC

AAAACCTATGATAATGGTGTTATATGTGCTTCTGAACAATCTGTAAT

AGTCTTAAAATCCATATATAACAAGGTAAAAGATGAGTTCCAAGAAA

GAGGAGCTTATATAATAAAGAAAAACGAATTGGATAAAGTCCGTGAA

```
GTGATTTTTAAAGATGGATCCGTAAACCCTAAAATAGTCGGACAGTC

AGCTTATACTATAGCAGCTATGGCTGGCATAAAAGTACCTAAAACCA

CAAGAATATTAATAGGAGAAGTTACCTCCTTAGGTGAAGAAGAACCT

TTTGCCCACGAAAAACTATCTCCTGTTTTGGCTATGTATGAGGCTGA

CAATTTTGATGATGCTTTAAAAAAAGCAGTAACTCTAATAAACTTAG

GAGGCCTCGGCCATACCTCAGGAATATATGCAGATGAAATAAAAGCA

CGAGATAAAATAGATAGATTTAGTAGTGCCATGAAAACCGTAAGAAC

CTTTGTAAATATCCCAACCTCACAAGGTGCAAGTGGAGATCTATATA

ATTTTAGAATACCACCTTCTTTCACGCTTGGCTGCGGATTTTGGGGA

GGAAATTCTGTTTCCGAGAATGTTGGTCCAAAACATCTTTTGAATAT

TAAAACCGTAGCTGAAAGGAGAGAAAACATGCTTTGGTTTAGAGTTC

CACATAAAGTATATTTTAAGTTCGGTTGTCTTCAATTTGCTTTAAAA

GATTTAAAAGATCTAAAGAAAAAAAGAGCCTTTATAGTTACTGATAG

TGACCCCTATAATTTAAACTATGTTGATTCAATAATAAAAATACTTG

AGCACCTAGATATTGATTTTAAAGTATTTAATAAGGTTGGAAGAGAA

GCTGATCTTAAAACCATAAAAAAAGCAACTGAAGAAATGTCCTCCTT

TATGCCAGACACTATAATAGCTTTAGGTGGTACCCCTGAAATGAGCT

CTGCAAAGCTAATGTGGGTACTATATGAACATCCAGAAGTAAAATTT

GAAGATCTTGCAATAAAATTTATGGACATAAGAAAGAGAATATATAC

TTTCCCAAAACTCGGTAAAAAGGCTATGTTAGTTGCAATTACAACTT

CTGCTGGTTCCGGTTCTGAGGTTACTCCTTTTGCTTTAGTAACTGAC

AATAACACTGGAAATAAGTACATGTTAGCAGATTATGAAATGACACC

AAATATGGCAATTGTAGATGCAGAACTTATGATGAAAATGCCAAAGG

GATTAACCGCTTATTCAGGTATAGATGCACTAGTAAATAGTATAGAA

GCATACACATCCGTATATGCTTCAGAATACACAAACGGACTAGCACT

AGAGGCAATACGATTAATATTTAAATATTTGCCTGAGGCTTACAAAA

ACGGAAGAACCAATGAAAAGCAAGAGAGAAAATGGCTCACGCTTCA

ACTATGGCAGGTATGGCATCCGCTAATGCATTTCTAGGTCTATGTCA

TTCCATGGCAATAAAATTAAGTTCAGAACACAATATTCCTAGTGGCA

TTGCCAATGCATTACTAATAGAAGAAGTAATAAAATTTAACGCAGTT

GATAATCCTGTAAAACAAGCCCCTTGCCCACAATATAAGTATCCAAA

CACCATATTTAGATATGCTCGAATTGCAGATTATATAAAGCTTGGAG

GAAATACTGATGAGGAAAAGGTAGATCTCTTAATTAACAAAATACAT

GAACTAAAAAAAGCTTTAAATATACCAACTTCAATAAAGGATGCAGG

TGTTTTGGAGGAAACTTCTATTCCTCCCTTGATAGAATATCTGAAC

TTGCACTAGATGATCAATGCACAGGCGCTAATCCTAGATTTCCTCTT

ACAAGTGAGATAAAAGAAATGTATATAAATTGTTTTAAAAAACAACC

TTAA
```

Example Amino Acid Sequence:

```
                                      (SEQ ID NO: 18)
MKVTTVKELDEKLKVIKEAQKKFSCYSQEMVDEIFRNAAMAAIDARI

ELAKAAVLETGMGLVEDKVIKNHFAGEYIYNKYKDEKTCGIIERNEP

YGITKIAEPIGVVAAIIPVTNPTSTTIFKSLISLKTRNGIFFSPHPR

AKKSTILAAKTILDAAVKSGAPENIIGWIDEPSIELTQYLMQKADIT

LATGGPSLVKSAYSSGKPAIGVGPGNTPVIIDESAHIKMAVSSIILS

KTYDNGVICASEQSVIVLKSIYNKVKDEFQERGAYIIKKNELDKVRE

VIFKDGSVNPKIVGQSAYTIAAMAGIKVPKTTRILIGEVTSLGEEEP

FAHEKLSPVLAMYEADNFDDALKKAVTLINLGGLGHTSGIYADEIKA

RDKIDRFSSAMKTVRTFVNIPTSQGASGDLYNFRIPPSFTLGCGFWG

GNSVSENVGPKHLLNIKTVAERRENMLWFRVPHKVYFKFGCLQFALK

DLKDLKKKRAFIVTDSDPYNLNYVDSIIKILEHLDIDFKVFNKVGRE

ADLKTIKKATEEMSSFMPDTIIALGGTPEMSSAKLMWVLYEHPEVKF

EDLAIKFMDIRKRIYTFPKLGKKAMLVAITTSAGSGSEVTPFALVTD

NNTGNKYMLADYEMTPNMAIVDAELMMKMPKGLTAYSGIDALVNSIE

AYTSVYASEYTNGLALEAIRLIFKYLPEAYKNGRTNEKAREKMAHAS

TMAGMASANAFLGLCHSMAIKLSSEHNIPSGIANALLIEEVIKFNAV

DNPVKQAPCPQYKYPNTIFRYARIADYIKLGGNTDEEKVDLLINKIH

ELKKALNIPTSIKDAGVLEENFYSSLDRISELALDDQCTGANPRFPL

TSEIKEMYINCFKKQP
```

An exemplary butanol dehydrogenase (BDH) for use in the present invention catalyzes the dehydrogenation of an aldehyde into an alcohol, particularly crotonaldehyde into crotyl alcohol, though any aldehyde can be a substrate. This reaction typically requires a coenzyme, such as NADH or NADPH. Exemplary butanol dehydrogenase nucleic acid and amino acid sequences (from *C. acetobutylicum* ATCC 824) are set forth below:

EC number: 1.1.1.1

Example Nucleic Acid Sequence:

```
                                      (SEQ ID NO: 19)
GTGGTTGATTTCGAATATTCAATACCAACTAGAATTTTTTTCGGTAA

AGATAAGATAAATGTACTTGGAAGAGAGCTTAAAAAATATGGTTCTA

AAGTGCTTATAGTTTATGGTGGAGGAAGTATAAAGAGAAATGGAATA

TATGATAAAGCTGTAAGTATACTTGAAAAAAACAGTATTAAATTTTA

TGAACTTGCAGGAGTAGAGCCAAATCCAAGAGTAACTACAGTTGAAA

AAGGAGTTAAAATATGTAGAGAAAATGGAGTTGAAGTAGTACTAGCT

ATAGGTGGAGGAAGTGCAATAGATTGCGCAAAGGTTATAGCAGCAGC

ATGTGAATATGATGGAAATCCATGGGATATTGTGTTAGATGGCTCAA

AAATAAAAAGGGTGCTTCCTATAGCTAGTATATTAACCATTGCTGCA

ACAGGATCAGAAATGGATACGTGGGCAGTAATAAATAATATGGATAC

AAACGAAAAACTAATTGCGGCACATCCAGATATGGCTCCTAAGTTTT

CTATATTAGATCCAACGTATACGTATACCGTACCTACCAATCAAACA
```

```
GCAGCAGGAACAGCTGATATTATGAGTCATATATTTGAGGTGTATTT

TAGTAATACAAAAACAGCATATTTGCAGGATAGAATGGCAGAAGCGT

TATTAAGAACTTGTATTAAATATGGAGGAATAGCTCTTGAGAAGCCG

GATGATTATGAGGCAAGAGCCAATCTAATGTGGGCTTCAAGTCTTGC

GATAAATGGACTTTTAACATATGGTAAAGACACTAATTGGAGTGTAC

ACTTAATGGAACATGAATTAAGTGCTTATTACGACATAACACACGGC

GTAGGGCTTGCAATTTTAACACCTAATTGGATGGAGTATATTTTAAA

TAATGATACAGTGTACAAGTTTGTTGAATATGGTGTAAATGTTTGGG

GAATAGACAAAGAAAAAAATCACTATGACATAGCACATCAAGCAATA

CAAAAAACAAGAGATTACTTTGTAAATGTACTAGGTTTACCATCTAG

ACTGAGAGATGTTGGAATTGAAGAAGAAAAATTGGACATAATGGCAA

AGGAATCAGTAAAGCTTACAGGAGGAACCATAGGAAACCTAAGACCA

GTAAACGCCTCCGAAGTCCTACAAATATTCAAAAAATCTGTGTAA
```

Example Amino Acid Sequence:

(SEQ ID NO: 20)
```
MVDFEYSIPTRIFFGKDKINVLGRELKKYGSKVLIVYGGGSIKRNGI

YDKAVSILEKNSIKFYELAGVEPNPRVTTVEKGVKICRENGVEVVLA

IGGGSAIDCAKVIAAACEYDGNPWDIVLDGSKIKRVLPIASILTIAA

TGSEMDTWAVINNMDTNEKLIAAHPDMAPKFSILDPTYTYTVPTNQT

AAGTADIMSHIFEVYFSNTKTAYLQDRMAEALLRTCIKYGGIALEKP

DDYEARANLMWASSLAINGLLTYGKDTNWSVHLMEHELSAYYDITHG

VGLAILTPNWMEYILNNDTVYKFVEYGVNVWGIDKEKNHYDIAHQAI

QKTRDYFVNVLGLPSRLRDVGIEEEKLDIMAKESVKLTGGTIGNLRP

VNASEVLQIFKKSV
```

An exemplary CoA-transferase subunit A (COAT-A) for use in the present invention catalyzes the transfer of coenzyme-A (CoA) between two molecules. For example, from acetoacetyl-CoA to acetate to form acetoacetate and acetyl-CoA or from acetoacetyl-CoA to butyrate to form acetoacetate and butyryl-CoA. Exemplary COAT-A, i.e., subunit A nucleic acid and amino acid sequences (from *C. acetobutylicum* ATCC 824) are set forth below:
EC number: 2.8.3.8 or 2.8.3.9 or other related enzymes
Example Nucleic Acid Sequence:

(SEQ ID NO: 21)
```
ATGAACTCTAAAATAATTAGATTTGAAAATTTAAGGTCATTCTTTAA

AGATGGGATGACAATTATGATTGGAGGTTTTTTAAACTGTGGCACTC

CAACCAAATTAATTGATTTTTTAGTTAATTTAAATATAAAGAATTTA

ACGATTATAAGTAATGATACATGTTATCCTAATACAGGTATTGGTAA

GTTAATATCAAATAATCAAGTAAAAAAGCTTATTGCTTCATATATAG

GCAGCAACCCAGATACTGGCAAAAAACTTTTTAATAATGAACTTGAA

GTAGAGCTCTCTCCCCAAGGAACTCTAGTGGAAAGAATACGTGCAGG

CGGATCTGGCTTAGGTGGTGTACTAACTAAAACAGGTTTAGGAACTT

TGATTGAAAAGGAAAGAAAAAAATATCTATAAATGGAACGGAATAT
```

```
TTGTTAGAGCTACCTCTTACAGCCGATGTAGCATTAATTAAAGGTAG

TATTGTAGATGAGGCCGGAAACACCTTCTATAAAGGTACTACTAAAA

ACTTTAATCCCTATATGGCAATGGCAGCTAAAACCGTAATAGTTGAA

GCTGAAAATTTAGTTAGCTGTGAAAAACTAGAAAAGGAAAAAGCAAT

GACCCCCGGAGTTCTTATAAATTATATAGTAAAGGAGCCTGCATAA
```

Example Amino Acid Sequence:

(SEQ ID NO: 22)
```
MNSKIIRFENLRSFEKDGMTIMIGGFLNCGTPTKLIDFLVNLNIKNL

TIISNDTCYPNTGIGKLISNNQVKKLIASYIGSNPDTGKKLFNNELE

VELSPQGTLVERIRAGGSGLGGVLTKTGLGTLIEKGKKKISINGTEY

LLELPLTADVALIKGSIVDEAGNTFYKGTTKNFNPYMAMAAKTVIVE

AENLVSCEKLEKEKAMTPGVLINYIVKEPA
```

An exemplary CoA-transferase subunit B (COAT-B) for use in the present invention catalyzes the transfer of coenzyme-A (CoA) between two molecules. For example, from acetoacetyl-CoA to acetate to form acetoacetate and acetyl-CoA or from acetoacetyl-CoA to butyrate to form acetoacetate and butyryl-CoA. Exemplary COAT-B, i.e., subunit B nucleic acid and amino acid sequences (from *C. acetobutylicum* ATCC 824) are set forth below:
EC number: 2.8.3.8 or 2.8.3.9 or other related enzymes
Example Nucleic Acid Sequence:

(SEQ ID NO: 23)
```
ATGATTAATGATAAAAACCTAGCGAAAGAAATAATAGCCAAAAGAGT

TGCAAGAGAATTAAAAAATGGTCAACTTGTAAACTTAGGTGTAGGTC

TTCCTACCATGGTTGCAGATTATATACCAAAAAATTTCAAAATTACT

TTCCAATCAGAAAACGGAATAGTTGGAATGGGCGCTAGTCCTAAAAT

AAATGAGGCAGATAAAGATGTAGTAAATGCAGGAGGAGACTATACAA

CAGTACTTCCTGACGGCACATTTTTCGATAGCTCAGTTTCGTTTTCA

CTAATCCGTGGTGGTCACGTAGATGTTACTGTTTTAGGGGCTCTCCA

GGTAGATGAAAAGGGTAATATAGCCAATTGGATTGTTCCTGGAAAAA

TGCTCTCTGGTATGGGTGGAGCTATGGATTTAGTAAATGGAGCTAAG

AAAGTAATAATTGCAATGAGACATACAAATAAAGGTCAACCTAAAAT

TTTAAAAAAATGTACACTTCCCCTCACGGCAAAGTCTCAAGCAAATC

TAATTGTAACAGAACTTGGAGTAATTGAGGTTATTAATGATGGTTTA

CTTCTCACTGAAATTAATAAAAACACAACCATTGATGAAATAAGGTC

TTTAACTGCTGCAGATTTACTCATATCCAATGAACTTAGACCCATGG

CTGTTTAG
```

Example Amino Acid Sequence:

(SEQ ID NO: 24)
```
MINDKNLAKEIIAKRVARELKNGQLVNLGVGLPTMVADYIPKNFKIT

FQSENGIVGMGASPKINEADKDVVNAGGDYTTVLPDGTFFDSSVSFS

LIRGGHVDVTVLGALQVDEKGNIANWIVPGKMLSGMGGAMDLVNGAK
```

KVIIAMRHTNKGQPKILKKCTLPLTAKSQANLIVTELGVIEVINDGL

LLTEINKNTTIDEIRSLTAADLLISNELRPMAV

An exemplary aldehyde:ferredoxin oxidoreductase (AOR) for use in the present invention catalyzes the reduction of a carboxylic acid into its corresponding aldehyde. For example, crotonic acid into crotonaldehyde. This reaction typically requires a coenzyme, such as ferredoxin. Exemplary AOR nucleic acid and amino acid sequences (from *C. ljungdahlii* DSM 13528) are set forth below:

EC number: 1.2.7.5

Example Nucleic Acid Sequence:

(SEQ ID NO: 25)
ATGTACGGATATAAGGGTAAGGTATTAAGAATTAATCTAAGTAGTAAAAC

TTATATAGTGGAAGAATTGAAAATTGACAAAGCTAAAAAATTTATAGGTG

CAAGAGGGTTAGGCGTAAAAACCTTATTTGACGAAGTAGATCCAAAGGTA

GATCCATTATCACCTGATAACAAATTTATTATAGCAGCGGGACCACTTAC

AGGTGCACCTGTTCCAACAAGCGGAAGATTCATGGTAGTTACTAAATCAC

CTTTAACAGGAACTATTGCTATTGCAAATTCAGGTGGAAAATGGGGAGCA

GAATTCAAAGCAGCTGGATACGATATGATAATCGTTGAAGGTAAATCTGA

TAAAGAAGTTTATGTAAATATAGTAGATGATAAAGTAGAATTTAGGGATG

CTTCTCATGTTTGGGGAAAACTAACAGAAGAAACTACAAAAATGCTTCAA

CAGGAAACAGATTCGAGAGCTAAGGTTTTATGCATAGGACCAGCTGGGGA

AAAGTTATCACTTATGGCAGCAGTTATGAATGATGTTGATAGAACAGCAG

GACGTGGTGGTGTTGGAGCTGTTATGGGTTCAAAGAACTTAAAAGCTATT

GTAGTTAAAGGAAGCGGAAAAGTAAAATTATTTGATGAACAAAAAGTGAA

GGAAGTAGCACTTGAGAAAACAAATATTTTAAGAAAAGATCCAGTAGCTG

GTGGAGGACTTCCAACATACGGAACAGCTGTACTTGTTAATATTATAAAT

GAAAATGGTGTACATCCAGTAAAGAATTTTCAAAAATCTTATACAGATCA

AGCAGATAAGATCAGTGGAGAAACTTTAACTAAAGATTGCTTAGTTAGAA

AAAATCCTTGCTATAGGTGTCCAATTGCCTGTGGAAGATGGGTAAAACTT

GATGATGGAACTGAATGTGGAGGACCAGAATATGAAACATTATGGTCATT

TGGATCTGATTGTGATGTATACGATATAAATGCTGTAAATACAGCAAATA

TGTTGTGTAATGAATATGGATTAGATACCATTACAGCAGGATGTACTATT

GCAGCAGCTATGGAACTTTATCAAAGAGGTTATATTAAGGATGAAGAAAT

AGCAGCAGATGGATTGTCACTTAATTGGGGAGATGCTAAGTCCATGGTTG

AATGGGTAAAGAAAATGGGACTTAGAGAAGGATTTGGAGACAAGATGGCA

GATGGTTCATACAGACTTTGTGACTCATACGGTGTACCTGAGTATTCAAT

GACTGTAAAAAAACAGGAACTTCCAGCATATGACCCAAGAGGAATACAGG

GACATGGTATTACTTATGCTGTTAACAATAGGGGAGGATGTCACATTAAG

GGATATATGGTAAGTCCTGAAATACTTGGCTATCCAGAAAAACTTGATAG

ACTTGCAGTGGAAGGAAAAGCAGGATATGCTAGAGTATTCCATGATTTAA

CAGCTGTTATAGATTCACTTGGATTATGTATTTTTACAACATTTGGTCTT

GGTGCACAGGATTATGTTGATATGTATAATGCAGTAGTTGGTGGAGAATT

ACATGATGTAAATTCTTTAATGTTAGCTGGAGATAGAATATGGACTTTAG

AAAAAATATTTAACTTAAAGGCAGGCATAGATAGTTCACAGGATACTCTT

CCAAAGAGATTGCTTGAAGAACAAATTCCAGAAGGACCATCAAAAGGAGA

AGTTCATAAGTTAGATGTACTACTACCTGAATATTATTCAGTACGTGGAT

GGGATAAAAATGGTATTCCTACAGAGGAAACGTTAAAGAAATTAGGATTA

GATGAATACGTAGGTAAGCTTTAG

Example Amino Acid Sequence:

(SEQ ID NO: 26)
MYGYKGKVLRINLSSKTYIVEELKIDKAKKFIGARGLGVKTLFDEVDPKV

DPLSPDNKFIIAAGPLTGAPVPTSGRFMVVTKSPLTGTIAIANSGGKWGA

EFKAAGYDMIIVEGKSDKEVYVNIVDDKVEFRDASHVWGKLTEETTKMLQ

QETDSRAKVLCIGPAGEKLSLMAAVMNDVDRTAGRGGVGAVMGSKNLKAI

VVKGSGKVKLFDEQKVKEVALEKTNILRKDPVAGGGLPTYGTAVLVNIIN

ENGVHPVKNFQKSYTDQADKISGETLTKDCLVRKNPCYRCPIACGRWVKL

DDGTECGGPEYETLWSFGSDCDVYDINAVNTANMLCNEYGLDTITAGCTI

AAAMELYQRGYIKDEEIAADGLSLNWGDAKSMVEWVKKMGLREGFGDKMA

DGSYRLCDSYGVPEYSMTVKKQELPAYDPRGIQGHGITYAVNNRGGCHIK

GYMVSPEILGYPEKLDRLAVEGKAGYARVFHDLTAVIDSLGLCIFTTFGL

GAQDYVDMYNAVVGGELHDVNSLMLAGDRIWTLEKIFNLKAGIDSSQDTL

PKRLLEEQIPEGPSKGEVHKLDVLLPEYYSVRGWDKNGIPTEETLKKLGL

DEYVGKL

An exemplary acetoacetate decarboxylase (ADC) for use in the present invention catalyzes the decarboxylation of acetoacetate into acetone and $CO_2$. Exemplary ADC nucleic acid and amino acid sequences (from *C. acetobutylicum* ATCC 824) are set forth below:

EC number: 4.1.1.4

Example Nucleic Acid Sequence:

(SEQ ID NO: 27)
ATGTTAAAGGATGAAGTAATTAAACAAATTAGCACGCCATTAACTTCGCC

TGCATTTCCTAGAGGACCCTATAAATTTCATAATCGTGAGTATTTTAACA

TTGTATATCGTACAGATATGGATGCACTTCGTAAAGTTGTGCCAGAGCCT

TTAGAAATTGATGAGCCCTTAGTCAGGTTTGAAATTATGGCAATGCATGA

TACGAGTGGACTTGGTTGTTATACAGAAAGCGGACAGGCTATTCCCGTAA

GCTTTAATGGAGTTAAGGGAGATTATCTTCATATGATGTATTTAGATAAT

GAGCCTGCAATTGCAGTAGGAAGGGAATTAAGTGCATATCCTAAAAAGCT

CGGGTATCCAAAGCTTTTTGTGGATTCAGATACTTTAGTAGGAACTTTAG

ACTATGGAAAACTTAGAGTTGCGACAGCTACAATGGGGTACAAACATAAA

GCCTTAGATGCTAATGAAGCAAAGGATCAAATTTGTCGCCCTAATTATAT

GTTGAAAATAATACCCAATTATGATGGAAGCCCTAGAATATGTGAGCTTA

TAAATGCGAAAATCACAGATGTTACCGTACATGAAGCTTGGACAGGACCA

ACTCGACTGCAGTTATTTGATCACGCTATGGCGCCACTTAATGATTTGCC

AGTAAAAGAGATTGTTTCTAGCTCTCACATTCTTGCAGATATAATATTGC

-continued

CTAGAGCTGAAGTTATATATGATTATCTTAAGTAA

Example Amino Acid Sequence:

(SEQ ID NO: 28)
MLKDEVIKQISTPLTSPAFPRGPYKEENREYFNIVYRTDMDALRKVVPEP

LEIDEPLVRFEIMAMHDTSGLGCYTESGQAIPVSENGVKGDYLHMMYLDN

EPAIAVGRELSAYPKKLGYPKLEVDSDTLVGTLDYGKLRVATATMGYKHK

ALDANEAKDQICRPNYMLKIIPNYDGSPRICELINAKITDVTVHEAWTGP

TRLQLFDHAMAPLNDLPVKEIVSSSHILADIILPRAEVIYDYLK

An exemplary secondary alcohol dehydrogenase (SADH) for use in the present invention catalyzes the reduction of a ketone into a secondary alcohol. For example, acetone into 2-propanol (a.k.a. isopropanol). The exemplary SADH may have EC number 1.1.1.1. Exemplary SADH nucleic acid and amino acid sequences (from *C. ljungdahlii* DSM 13528) are set forth in SEQ ID NO: 1 and SEQ ID NO: 2, respectively.

An exemplary butyryl-CoA dehydrogenase (BCD) for use in the present invention catalyzes the reduction of crotonyl-CoA into butyryl-CoA by reducing the carbon-carbon double bond in crotonyl-CoA. This enzyme requires an electron-transfer flavoprotein. Exemplary BCD nucleic acid and amino acid sequences (from *C. acetobutylicum* ATCC 824) are set forth below:

EC number: 1.3.8.1
Example Nucleic Acid Sequence:

(SEQ ID NO: 29)
ATGGATTTTAATTTAACAAGAGAACAAGAATTAGTAAGACAGATGGTTAG

AGAATTTGCTGAAAATGAAGTTAAACCTATAGCAGCAGAAATTGATGAAA

CAGAAAGATTTCCAATGGAAAATGTAAAGAAAATGGGTCAGTATGGTATG

ATGGGAATTCCATTTTCAAAAGAGTATGGTGGCGCAGGTGGAGATGTATT

ATCTTATATAATCGCCGTTGAGGAATTATCAAAGGTTTGCGGTACTACAG

GAGTTATTCTTTCAGCACATACATCACTTTGTGCTTCATTAATAAATGAA

CATGGTACAGAAGAACAAAACAAAAATATTTAGTACCTTTAGCTAAAGG

TGAAAAAATAGGTGCTTATGGATTGACTGAGCCAAATGCAGGAACAGATT

CTGGAGCACAACAAACAGTAGCTGTACTTGAAGGAGATCATTATGTAATT

AATGGTTCAAAAATATTCATAACTAATGGAGGAGTTGCAGATACTTTTGT

TATATTTGCAATGACTGACAGAACTAAAGGAACAAAAGGTATATCAGCAT

TTATAATAGAAAAGGCTTCAAAGGTTTCTCTATTGGTAAAGTTGAACAA

AAGCTTGGAATAAGAGCTTCATCAACAACTGAACTTGTATTTGAAGATAT

GATAGTACCAGTAGAAAACATGATTGGTAAAGAAGGAAAAGGCTTCCCTA

TAGCAATGAAAACTCTTGATGGAGGAAGAATTGGTATAGCAGCTCAAGCT

TTAGGTATAGCTGAAGGTGCTTTCAACGAAGCAAGAGCTTACATGAAGGA

GAGAAAACAATTTGGAAGAAGCCTTGACAAATTCCAAGGTCTTGCATGGA

TGATGGCAGATATGGATGTAGCTATAGAATCAGCTAGATATTTAGTATAT

AAAGCAGCATATCTTAAACAAGCAGGACTTCCATACACAGTTGATGCTGC

AAGAGCTAAGCTTCATGCTGCAAATGTAGCAATGGATGTAACAACTAAGG

-continued

CAGTACAATTATTTGGTGGATACGGATATACAAAAGATTATCCAGTTGAA

AGAATGATGAGAGATGCTAAGATAACTGAAATATATGAAGGAACTTCAGA

AGTTCAGAAATTAGTTATTTCAGGAAAAATTTTTAGATAA

Example Amino Acid Sequence:

(SEQ ID NO: 30)
MDFNLTREQELVRQMVREFAENEVKPIAAEIDETERFPMENVKKMGQYGM

MGIPFSKEYGGAGGDVLSYIIAVEELSKVCGTTGVILSAHTSLCASLINE

HGTEEQKQKYLVPLAKGEKIGAYGLTEPNAGTDSGAQQTVAVLEGDHYVI

NGSKIFITNGGVADTFVIFAMTDRTKGTKGISAFIIEKGFKGFSIGKVEQ

KLGIRASSTTELVFEDMIVPVENMIGKEGKGFPIAMKTLDGGRIGIAAQA

LGIAEGAFNEARAYMKERKQFGRSLDKFQGLAWMMADMDVAIESARYLVY

KAAYLKQAGLPYTVDAARAKLHAANVAMDVTTKAVQLEGGYGYTKDYPVE

RMMRDAKITEIYEGTSEVQKLVISGKIFR

An exemplary trans-2-enoyl-CoA reductase (TER) for use in the present invention catalyzes the reduction of crotonyl-CoA into butyryl-CoA by reducing the carbon-carbon double bond in crotonyl-CoA. Exemplary TER nucleic acid and amino acid sequences from *Euglena gracilis* are set forth below:

EC number: 1.3.1.44
Example Nucleic Acid Sequence:

(SEQ ID NO: 31)
ATGATAGTAAAAGCAAAGTTTGTAAAAGGATTTATCAGAGATGTACATCC

TTATGGTTGCAGAAGGGAAGTACTAAATCAAATAGATTATTGTAAGAAGG

CTATTGGGTTTAGGGGACCAAAGAAGGTTTTAATTGTTGGAGCCTCATCT

GGGTTTGGTCTTGCTACTAGAATTTCAGTTGCATTTGGAGGTCCAGAAGC

TCACACAATTGGAGTATCCTATGAAACAGGAGCTACAGATAGAAGAATAG

GAACAGCGGGATGGTATAATAACATATTTTTAAAGAATTTGCTAAAAAA

AAAGGATTAGTTGCAAAAAACTTCATTGAGGATGCCTTTTCTAATGAAAC

CAAAGATAAAGTTATTAAGTATATAAAGGATGAATTTGGTAAAATAGATT

TATTTGTTTATAGTTTAGCTGCGCCTAGGAGAAAGGACTATAAAACTGGA

AATGTTTATACTTCAAGAATAAAAACAATTTTAGGAGATTTTGAGGGACC

GACTATTGATGTTGAAAGAGACGAGATTACTTTAAAAAAGGTTAGTAGTG

CTAGCATTGAAGAAATTGAAGAAACTAGAAAGGTAATGGGTGGAGAGGAT

TGGCAAGAGTGGTGTGAAGAGCTGCTTTATGAAGATTGTTTTTCGGATAA

AGCAACTACCATAGCATACTCGTATATAGGATCCCCAAGAACCTACAAGA

TATATAGAGAAGGTACTATAGGAATAGCTAAAAAGGATCTTGAAGATAAG

GCTAAGCTTATAAATGAAAAACTTAACAGAGTTATAGGTGGTAGAGCCTT

TGTGTCTGTGAATAAAGCATTAGTTACAAAAGCAAGTGCATATATTCCAA

CTTTTCCTCTTTATGCAGCTATTTTATATAAGGTCATGAAAGAAAAAAAT

ATTCATGAAAATTGTATTATGCAAATTGAGAGAATGTTTTCTGAAAAAAT

ATATTCAAATGAAAAAATACAATTTGATGACAAGGGAAGATTAAGGATGG

ACGATTTAGAGCTTAGAAAAGACGTTCAAGACGAAGTTGATAGAATATGG

-continued

```
AGTAATATTACTCCTGAAAATTTTAAGGAATTATCTGATTATAAGGGATA
CAAAAAAGAATTCATGAACTTAAACGGTTTTGATCTAGATGGGGTTGATT
ATAGTAAAGACCTGGATATAGAATTATTAAGAAAATTAGAACCTTAA
```

Example Amino Acid Sequence:

```
                                           (SEQ ID NO: 32)
MIVKAKFVKGFIRDVHPYGCRREVLNQIDYCKKAIGFRGPKKVLIVGASS
GFGLATRISVAFGGPEAHTIGVSYETGATDRRIGTAGWYNNIFFKEFAKK
KGLVAKNFIEDAFSNETKDKVIKYIKDEFGKIDLFVYSLAAPRRKDYKTG
NVYTSRIKTILGDFEGPTIDVERDEITLKKVSSASIEEIEETRKVMGGED
WQEWCEELLYEDCFSDKATTIAYSYIGSPRTYKIYREGTIGIAKKDLEDK
AKLINEKLNRVIGGRAFVSVNKALVTKASAYIPTFPLYAAILYKVMKEKN
IHENCIMQIERMFSEKIYSNEKIQFDDKGRLRMDDLELRKDVQDEVDRIW
SNITPENFKELSDYKGYKKEFMNLNGFDLDGVDYSKDLDIELLRKLEP
```

Exemplary secondary alcohol dehydrogenase (SADH) nucleic acid and amino acid sequences from *Clostridium beijerinckii* DSM 6423 are set forth below:

Example Nucleic Acid Sequence:

```
                                           (SEQ ID NO: 33)
ATGAAAGGTTTTGCAATGCTAGGTATTAATAAGTTAGGATGGATCGAAAA
AGAAAGGCCAGTTGCGGGTTCATATGATGCTATTGTACGCCCATTAGCAG
TATCTCCGTGTACATCAGATATACATACTGTTTTGAGGGAGCTCTTGGA
GATAGGAAGAATATGATTTTAGGGCATGAAGCTGTAGGTGAAGTTGTTGA
AGTAGGAAGTGAAGTGAAGGATTTTAAACCTGGTGACAGAGTTATAGTTC
CTTGTACAACTCCAGATTGGAGATCTTTGGAAGTTCAAGCTGGTTTTCAA
CAGCACTCAAACGGTATGCTCGCAGGATGGAAATTTTCAAATTTCAAGGA
TGGAGTTTTTGGTGAATATTTTCATGTAAATGATGCGGATATGAATCTTG
CGATTCTACCTAAAGACATGCCATTAGAAAATGCTGTTATGATAACAGAT
ATGATGACTACTGGATTTCATGGAGCAGAACTTGCAGATATTCAAATGGG
TTCAAGTGTTGTGGTAATTGGCATTGGAGCTGTTGGCTTAATGGGAATAG
CAGGTGCTAAATTACGTGGAGCAGGTAGAATAATTGGAGTGGGGAGCAGG
CCGATTTGTGTTGAGGCTGCAAAATTTTATGGAGCAACAGATATTCTAAA
TTATAAAAATGGTCATATAGTTGATCAAGTTATGAAATTAACGAATGGAA
AAGGCGTTGACCGCGTAATTATGGCAGGCGGTGGTTCTGAAACATTATCC
CAAGCAGTATCTATGGTTAAACCAGGAGGAATAATTTCTAATATAAATTA
TCATGGAAGTGGAGATGCTTTACTAATACCACGTGTAGAATGGGGATGTG
GAATGGCTCACAAGACTATAAAAGGAGGTCTTTGTCCTGGGGGACGTTTG
AGAGCAGAAATGTTAAGAGATATGGTAGTATATAATCGTGTTGATCTAAG
TAAATTAGTTACACATGTATATCATGGATTTGATCACATAGAAGAAGCAC
TGTTATTAATGAAAGACAAGCCAAAAGACTTAATTAAAGCAGTAGTTATA
TTATAA
```

Example Amino Acid Sequence:

```
                                           (SEQ ID NO: 34)
MKGFAMLGINKLGWIEKERPVAGSYDAIVRPLAVSPCTSDIHTVFEGALG
DRKNMILGHEAVGEVVEVGSEVKDFKPGDRVIVPCTTPDWRSLEVQAGFQ
QHSNGMLAGWKFSNFKDGVFGEYFHVNDADMNLAILPKDMPLENAVMITD
MMTTGFHGAELADIQMGSSVVVIGIGAVGLMGIAGAKLRGAGRIIGVSR
PICVEAAKFYGATDILNYKNGHIVDQVMKLTNGKGVDRVIMAGGGSETLS
QAVSMVKPGGIISNINYHGSGDALLIPRVEWGCGMAHKTIKGGLCPGGRL
RAEMLRDMVVYNRVDLSKLVTHVYHGFDHIEEALLLMKDKPKDLIKAVVI
L
```

Exemplary PTS nucleic acid and amino acid sequences (from *C. acetobutylicum* ATCC 824) are set forth below:

Example Nucleic Acid Sequence:

```
                                           (SEQ ID NO: 35)
ATGGGTAATAAGATATTTGCCGTACTTCAAAAAATCGGTAAATCTTTAAT
GCTTCCAGTATCTGTTCTACCGGCGGCTGGAATTCTATTGAGACTTGGAC
AGCCAGATTTGCTTAATATGCCTTATGTTCAAGCAGCAGGAAATGCTATT
TTTAATAATTTACCTTTAATTTTTGCGGTTGGAGTTGCTATAGGTTTTTC
AGGCGGAGAAGGTGTTGCAGCACTTGCAGCTGTAATTGGAGAACTAATAC
TTGAGGCGGTTGAAAAAACAGCAGGTGATACGGCAGCAGCAGCTTTAGCA
AAAACAGCGGCAGCTTCACATCATATGACGCTTGCAGCATTTCAAAAAAC
TCAAGAATACAGTAACATTGTAACTAAAACAACTATTAGTATGGGTGTTT
TTGGCGGTATAATAATCGGTCTTACAGCAGCTATTTTATATAATAAGTTC
CATGATATAAAGATGCCTCAAGTTTTGGGTTTCTTTGGTGGAAAACGTTT
CGTTCCAATTATAACTTCAATTTCAGCTCTTATTATTGCAACTATAGGAG
TAAATATTTGGTTGCCAATACAAGCTGGAATAAATTCACTAGCAGCATTT
GCAACTACATCACCAATTGGACCTGCAATGTATGCTGGAGGAAAAAGACT
TTTAATTCCACTAGGACTTCATCACATTTATTATCCATTGTTCTTATATC
AATTTGGTCACTTTGTTTCAAATGGAGTTACTTATGTAGGAGATACAGCA
AGATACTTCCATGGGATCCTACTGCCGGAAACTTCATGGCAGCAGAGTA
TCCAATACTAATGTTTGGTCTTCCAGGAGCTGCTCTAGCTATGATTGCAG
CTGCTAAAAAAGAAAAGAGAAAAGAAATGGCTGGAATGATGATTTCAGCA
GCATTTGTAGCATTTGTAACAGGTATTACAGAGCCAATTGAATTCTCATT
CATATTTGTTGCTCCAGTATTATTTGTGTTCCACGTACTTGCTGCATTCG
CATCTGGTCTTATTACAAGTTATTTACACATAAGATTAGGGTATACTTTC
TCAGCATCCTTCATAGATTATGTTTTAGGATTCAAATATGCAGGTCATCC
ATTACTTATATGGCTTGTAGGTATAGGGTTCTTTGTATTGTACTTTGTTG
TATTCTACTTCACAATTAAAGCAATGAACATTAAGACACCAGGTAGAGAA
GATGATGATGCAGAAGGTGTTAAGAAGATAAATGTAAAAGGAAAAGCTAA
GGCAGCTAAGGTGCTTGAAGCTATAGGCGGAAAAGATAATATAAAAGTAC
TTGATGCATGTATAACAAGATTAAGACTTAACTTAAATGATCCTTCTTTG
```

```
GTTGATAAAGCTACACTTAAAGCTCTTGGAGCAGCTGGAGTAATGACAGC
AGAAGATAGTGTTCAAGTAGTTTTTGGAACTGAAGCTGAAAGAATAAAAG
ATGACATAAAAGCAATTATACAAAATGGTGGATATGTTGAAGATGATTCA
GATAAGGAAGAAGAAGTTCAAGAGGATAAGCAAATTTCTAAAGGTGCACA
CGAACTTTTAAGTCCAGCTGATGGAGAAGTAGTTGGTATTGAGAGTGTTC
CGGATAGTACATTTGCTGAAAAAATGCTTGGAGACGGTTTTGCAGTAATA
CCTTCAGGAAATGAAGTACACTCACCAGCTGATGGAGAAGTATCAGTTTT
ATTCCCAACTAAGCATGCATTTGCAATAACAACAGAAGGCGGACTTGAAC
TTTTAATACATGTTGGAATTGATACTGTAGCATTAAATGGTGAAGGTTTC
ACAGCACATGTAAAACAAGGAGATAAAGTTAAAAAAGGAGATTTGATTTT
AACTTTAGATACTGAGTTTATAAAGAGCAAAGGTAAAAACCTTATAACTC
CAGTGATTGTAACTAACATGGATGTTGTAGGAAATATAGATGTTAAATTA
GGAAACGTTAAAAATTCCGAGAAAGCTGCGGATGTTACCGTAAAATAA
```

Example Amino Acid Sequence:

(SEQ ID NO: 36)
MGNKIFAVLQKIGKSLMLPVSVLPAAGILLRLGQPDLLNMPYVQAAGNAI
FNNLPLIFAVGVAIGFSGGEGVAALAAVIGELILEAVEKTAGDTAAAALA
KTAAASHHMTLAAFQKTQEYSNIVTKTTISMGVFGGIIIGLTAAILYNKF
HDIKMPQVLGFFGGKRFVPIITSISALIIATIGVNIWLPIQAGINSLAAF
ATTSPIGPAMYAGGKRLLIPLGLHHIYYPLFLYQFGHFVSNGVTYVGDTA
RYFHGDPTAGNFMAAEYPILMFGLPGAALAMIAAAKKEKRKEMAGMMISA
AFVAFVTGITEPIEFSFIFVAPVLFVFHVLAAFASGLITSYLHIRLGYTF
SASFIDYVLGFKYAGHPLLIWLVGIGFFVLYFVVFYFTIKAMNIKTPGRE
DDDAEGVKKINVKGKAKAAKVLEAIGGKDNIKVLDACITRLRLNLNDPSL
VDKATLKALGAAGVMTAEDSVQVVFGTEAERIKDDIKAIIQNGGYVEDDS
DKEEEVQEDKQISKGAHELLSPADGEVVGIESVPDSTFAEKMLGDGFAVI
PSGNEVHSPADGEVSVLFPTKHAFAITTEGGLELLIHVGIDTVALNGEGF
TAHVKQGDKVKKGDLILTLDTEFIKSKGKNLITPVIVTNMDVVGNIDVKL
GNVKNSEKAADVTVK

Exemplary PTS nucleic acid and amino acid sequences (from *C. saccharobutylicum* DSM 13864) are set forth below:

Example Nucleic Acid Sequence:

(SEQ ID NO: 37)
```
ATGTTAGTTGATGCTTTTTTGCGCACAAAGCATCTAAAACATCCCTATAT
ACAAAAAATATTTAAAAAGGGGAAAATGTTATGAAAGACAAAATTTTTG
GTATTTTACAGCGTGTAGGAAGATCTTTTATGCTTCCAATAGCTATTTTA
CCAGTAGCTGGATTATTTCTTGGTTTAGGTGGATCATTTACCAATGAAAC
AATGATTCAAGCTTATGGACTTACTGGGTTAATCGGACCTGGTACATTTA
TTTATTCAATCCTTTCTGTAATGAATGCAGCAGGAAATGTAGTGTTTGGC
AATTTGCCTTTATTATTTGCAATGGGTGTTGCAATTGGTATGGCTAAAAA
GGAAAAAGATGTTGCAGCTTTATCAGCAGCAATTGCATTCCTTATAATGC
ATGCATCAATAAGTGCTATGATTAATATTAATGGTGGAACTGATGCTCTT
CTTAGTGGTGCATCAACTTCAGTACTTGGTATTACTTCATTACAAATGGG
TGTTTTTGGTGGTATTATTGTAGGGCTTGGAGTAGCAGCGTTACATAATA
AATTCTATAAAATTGAATTACCACAGGTATTATCATTCTTTGGTGGAACT
AGATTTGTTCCAATTGTAAGTGCAATAACATATTTAATTGTTGGAATTTT
AATGTTTTATATTTGGCCTCCAATTCAAGGTGGTATTTATAAAGTTGGAG
ATCTTGTATTAAGATCAGGATATGCAGGAACATGGCTTTATGGTTTAATG
GAACGTTTATTAATACCTTTTGGTCTTCATCATGTATTTTACTTACCATT
CTGGCAAACAGCAGTTGGTGGTACAGCTACAGTAGGTGGGAAAGTTATTG
AAGGTGCTCAAAATATTTTCTTTGCTGAACTTGGAACTCCAGGAATAACA
CACTTTAGTGTTTCAGCAACAAGATTTATGTCAGGTAAATTCCCACTTAT
GATATTTGGTTTACCTGGAGCAGCGCTTGCGATGTACAGATGTGCAAAAC
CAGAAAAGAGAAAAGTAGTAGGTGGATTATTATTATCAGCAGCATTAACT
TCGATGTTAACTGGTATTACAGAACCAATTGAATTTACATTCTTATTTGT
TGCACCATTATTATATGGAATTCACTGCGTATTTGCTGGACTAGCTTATA
TGTTTATGCATATGTTAAATGTTGGAGTTGGTATGACTTTCTCTGGTGGA
TTTATAGATTTATTCTTATTTGGTATTTTACAAGGAAATGCTAAGACAAG
TTGGATTTGGGTTGCAGTTGTAGGTATTGCATATTTTGTAGTATACTATG
TATTGTTCTCTTTCTTAATTAAGAAGCTTGACTTAAAGACTCCAGGTCGT
GATGATTCTGAAGAAGTTAAACTTTATCGTAGAAGCGATTTAGATGCAAA
GAAAAAAGGTAATAATGCAGATAATGGAGAAAGTGAAAGTATAGATGAAT
TATCAGCTATGATCTGTCAAGGTCTTGGTGGTAAGAAGAATATTTCAGAT
GTTGACTGTTGCGCAACTAGATTACGTTGTACAGTTGTTAAATCAGAATT
AGTAAATGAAGCTTTATTAAAACAAACTGGAGCATCAGGAGTAGTTCATA
AAGGCGTAGGTGTTCAAATTATATATGGACCAAGAGTAACAGTTATAAAA
TCTAATTTAGAAGATTATTTAATTGCAGCACCTGATGAAGAAGTTGCTAT
AGATGCAGTAGAAGAAAAAGCACCTGAAATGCCAACTGAAAAGGAAGCGG
AAGGAAAAGTTGTTAATACAATAGTTTTAAGCAGTCCATTAACAGGAGAT
GCTAAAGATTTATCAGAAGCTCCAGATGAAGCATTTGCAAGCAAAATGAT
GGGAGACGGAGCGGTAGTAATTCCAAGTAATGGAGATGTTGTAGCACCAG
CAGATGGTGAGGTGAGTTTTGTATTCCCATCAAAACATGCAGTAGGATTA
ACAACAACTGATGGTCTTGAATTACTTATTCATATAGGAATAGATACAGT
AAAGCTTGATGGAAAAGGCTTTGAAACTTTCGTAAAAGAAGGAGACAAAG
TTAAAAAAGGTGATAAATTATTAAGCTTTGACTTAGAATTTATAAAAGAA
AATGCACCATCTATTGCATCACCATGCATTTGTACAGCATTAAGCAGCAA
ACAAAAAGTACGTTTGTTAAAAACAGGTGATATAAAGGCAGGAGAAGACT
TAATAGCAATTGATGTGCTTGAATAA
```

Example Amino Acid Sequence:

(SEQ ID NO: 38)
MLVDAFLRTKHLKHPYIQKIFKKGENVMKDKIFGILQRVGRSFMLPIAIL

PVAGLFLGLGGSFTNETMIQAYGLTGLIGPGTFIYSILSVMNAAGNVVEG

NLPLLFAMGVAIGMAKKEKDVAALSAAIAFLIMHASISAMININGGTDAL

LSGASTSVLGITSLQMGVFGGIIVGLGVAALHNKFYKIELPQVLSFEGGT

REVPIVSAITYLIVGILMFYIWPPIQGGIYKVGDLVLRSGYAGTWLYGLM

ERLLIPFGLHHVFYLPFWQTAVGGTATVGGKVIEGAQNIFFAELGTPGIT

HFSVSATRFMSGKFPLMIFGLPGAALAMYRCAKPEKRKVVGGLLLSAALT

SMLTGITEPIEFTFLEVAPLLYGIHCVFAGLAYMFMHMLNVGVGMTFSGG

FIDLFLEGILQGNAKTSWIWVAVVGIAYFVVYYVLFSFLIKKLDLKTPGR

DDSEEVKLYRRSDLDAKKKGNNADNGESESIDELSAMICQGLGGKKNISD

VDCCATRLRCTVVKSELVNEALLKQTGASGVVHKGVGVQIIYGPRVTVIK

SNLEDYLIAAPDEEVAIDAVEEKAPEMPTEKEAEGKVVNTIVLSSPLTGD

AKDLSEAPDEAFASKMMGDGAVVIPSNGDVVAPADGEVSFVFPSKHAVGL

TTTDGLELLIHIGIDTVKLDGKGFETFVKEGDKVKKGDKLLSFDLEFIKE

NAPSIASPCICTALSSKQKVRLLKTGDIKAGEDLIAIDVLE

In an embodiment, amino acid sequences as disclosed herein may include amino acid sequences having at least 75%, 80%, 85%, 90%, 91%, 92%, 93%, 94%, 95%, 96%, 97%, 98%, or 99% identity the disclosed wild type sequences. In an embodiment, a corresponding polynucleotide sequence may be a polynucleotide sequence encoding a wild type amino acid sequence as disclosed herein, and may further include a polynucleotide sequence which encodes a protein having at least 75%, 80%, 85%, 90%, 91%, 92%, 93%, 94%, 95%, 96%, 97%, 98%, or 99% identity to a wild type amino acid sequence as disclosed herein. In an embodiment, a polynucleotide sequence as disclosed herein may include a sequence which has 75%, 80%, 85%, 90%, 91%, 92%, 93%, 94%, 95%, 96%, 97%, 98%, or 99% identity to the disclosed wild type polynucleotide sequence.

EXAMPLES

Example 1

Acetogenic clostridia strain *C. ljungdahlii* was cultured under three conditions: 5 g/l of fructose (first feedstock) with a $N_2$ headspace at 20 psig (referred to as heterotrophic fermentation), no fructose with a CO (second feedstock) headspace at 20 psig (autotrophic fermentation), and 5 g/l of fructose with a CO headspace at 20 psig (mixotrophic fermentation). Three biological replicates were prepared, grown at 37° C. and shaken at 225 rpm. Table 1 shows the metabolite profiles and carbon yields achieved. Carbon yield for this experiment is calculated by dividing the total amount of carbon in produced bioproducts by the total amount of carbon metabolized from the first feedstock during fermentation.

TABLE 1

| | Concentration (mM) | | | | | Carbon yield |
|---|---|---|---|---|---|---|
| Hour | Fructose | Acetate | Ethanol | 2,3-butanediol | Lactate | |
| 5 g/l fructose with $N_2$ headspace | | | | | | |
| 0 | 27.52 | 3.74 | 0.29 | 0.11 | 0.00 | — |
| 41 | 25.36 | 8.28 | 1.98 | 0.13 | 0.00 | 67% |
| 49 | 19.06 | 16.58 | 5.77 | 0.19 | 0.00 | 65% |
| 56 | 10.19 | 29.27 | 8.29 | 0.36 | 0.00 | 62% |
| 65 | 0.62 | 44.19 | 12.63 | 0.63 | 0.00 | 64% |
| 73 | 0.05 | 45.07 | 13.60 | 0.66 | 0.00 | 65% |
| 80 | 0.03 | 45.11 | 14.81 | 0.72 | 0.00 | 67% |
| 5 g/l fructose with CO headspace | | | | | | |
| 0 | 27.23 | 3.74 | 0.00 | 0.11 | 0.00 | — |
| 49 | 25.86 | 4.16 | 0.48 | 0.19 | 0.16 | 32% |
| 56 | 25.12 | 4.30 | 0.75 | 0.19 | 0.12 | 26% |
| 65 | 25.07 | 5.14 | 1.49 | 0.35 | 0.14 | 55% |
| 73 | 22.39 | 5.85 | 2.15 | 0.39 | 0.17 | 35% |
| 80 | 22.32 | 7.96 | 4.19 | 0.55 | 0.23 | 65% |
| 85 | 20.36 | 9.76 | 5.62 | 1.77 | 0.21 | 74% |
| 89 | 19.69 | 12.14 | 5.24 | 2.46 | 0.49 | 84% |
| 97 | 16.56 | 17.62 | 9.26 | 4.49 | 1.00 | 104% |
| 104 | 9.68 | 19.22 | 14.75 | 8.70 | 1.38 | 94% |
| 113 | 3.07 | 27.38 | 23.10 | 16.53 | 2.59 | 115% |
| 121 | 0.00 | 29.65 | 22.65 | 17.85 | 2.63 | 108% |
| CO headspace (no fructose) | | | | | | |
| | Concentration (mM) | | | | | |
| Hour | Fructose | Acetate | Ethanol | 2,3-butanediol | Lactate | |
| 0 | 0.00 | 3.72 | 0.00 | 0.12 | 0.00 | |
| 41 | 0.00 | 4.02 | 0.47 | 0.14 | 0.00 | |
| 49 | 0.00 | 4.17 | 0.78 | 0.11 | 0.00 | |
| 56 | 0.00 | 4.32 | 0.46 | 0.10 | 0.25 | |
| 65 | 0.00 | 4.65 | 0.64 | 0.00 | 0.22 | |
| 73 | 0.00 | 4.71 | 0.52 | 0.08 | 0.20 | |
| 80 | 0.00 | 4.94 | 0.69 | 0.14 | 0.19 | |
| 89 | 0.00 | 5.63 | 0.74 | 0.14 | 0.18 | |
| 97 | 0.00 | 7.12 | 1.03 | 0.20 | 0.00 | |
| 104 | 0.00 | 8.26 | 1.07 | 0.24 | 0.19 | |
| 113 | 0.00 | 13.50 | 1.81 | 0.51 | 0.75 | |
| 121 | 0.00 | 17.62 | 2.51 | 0.93 | 0.32 | |

These results exemplify the non-additive, i.e., synergistic nature of the mixotrophic fermentation. Combining the heterotrophic fermentation broth with the autotrophic fermentation broth, the molar ratios of acetate, ethanol, 2,3-butanediol and lactate are: 0.77, 0.20, 0.02, and 0.004, respectively. In comparison, those for the mixotrophic fermentation are 0.40, 0.31, 0.24, and 0.04, respectively. The proportion of the more reduced products, ethanol, lactic acid and 2.3-butanediol is increased, while that of acetate decreases. Thus, the fraction of 2,3-butanediol in the mixotrophic fermentation is more than 10 times greater than that in the combination and that of acetate is about one half. In comparison, in the autotrophic fermentation, the molecular fraction of acetate is 0.82.

Additionally, the results show that, by the time the carbohydrate is metabolized, the mixotrophic fermentation has a much greater carbon yield compared to the heterotrophic fermentation.

This example demonstrates the ability to increase carbon efficiencies and increase the yield of reduced product with mixotrophic fermentation.

Example 2

Acetogenic clostridia strain *C. ljungdahlii* was cultured under two conditions: 10 g/l of fructose (first feedstock) with a headspace of the gas mixture of CO, $CO_2$, $H_2$, and $N_2$ (55%, 10%, 20%, 15%, respectively) (second feedstock) at 30 psig (referred to as mixotrophic fermentation) and no fructose with a headspace of the gas mixture of CO, $CO_2$, $H_2$, and $N_2$ (55%, 10%, 20%, 15%, respectively) (second feedstock) at 30 psig (referred to as autotrophic fermentation). Two biological replicates were prepared, grown at 37° C. and shaken at 225 rpm. The CO and $CO_2$ were labeled with $^{13}C$, allowing the ability to track the uptake and incorporation of the carbon substrates.

FIG. 1 shows the percentage of $^{13}C$ labeling of the metabolite acetate over time in both cultures. Average $^{13}C$ labeling of acetate for autotrophic (A) and mixotrophic (M) cultures between two biological replicates is shown. For the mixotrophic cultures, fructose was never depleted over the time sampled. The final concentration of fructose at timepoint 168 hr was 7.9 g/l.

The only way acetate could be labeled with $^{13}C$ is if the labeled gas, either $^{13}CO$ or $^{13}CO_2$, was utilized by the Wood-Ljungdahl pathway and used to form acetyl-CoA. For the autotrophic cultures, >90% of the acetate was labeled with $^{13}C$, indicating that less than 10% of the carbon came from the inoculum culture and yeast extract in the medium. For the mixotrophic cultures, ~80% of the acetate was labeled, even in the presence of excess fructose. This indicates that *C. ljungdahlii* is able to utilize and consume gas in the presence of excess sugar.

Example 3

The test of Example 1 was repeated using the acetogenic clostridia strain *C. autoethanogenum*. Table 2 shows the metabolite profiles and carbon yields.

Similar to the first example, the cultures with both fructose and a CO headspace had greater carbon efficiencies, indicating gas consumption. In addition, the mixotrophic cultures produced greater amounts of 2,3-butanediol. Compared to the pure gas culture, the mixotrophic culture produced bioproducts at a much faster rate and produced less acetate, relative to other bioproducts.

TABLE 2

| Hour | Concentration (mM) | | | | Carbon yield |
| | Fructose | Acetate | Ethanol | 2,3-butanediol | |
| --- | --- | --- | --- | --- | --- |
| 5 g/l fructose with $N_2$ headspace | | | | | |
| 0 | 27.55 | 6.71 | 3.46 | 0.00 | — |
| 84 | 26.89 | 9.15 | 4.74 | 0.00 | 120% |
| 94 | 23.43 | 12.69 | 7.14 | 0.38 | 77% |

TABLE 2-continued

| Hour | Concentration (mM) | | | | Carbon yield |
| | Fructose | Acetate | Ethanol | 2,3-butanediol | |
| --- | --- | --- | --- | --- | --- |
| 120 | 3.80 | 42.39 | 23.84 | 0.79 | 80% |
| 170 | 0.00 | 46.77 | 25.92 | 0.96 | 77% |
| 5 g/l fructose with CO headspace | | | | | |
| 0 | 24.62 | 7.08 | 3.81 | 0.19 | — |
| 53 | 23.75 | 9.11 | 6.26 | 0.19 | 170% |
| 58 | 22.35 | 10.62 | 10.09 | 0.36 | 149% |
| 63 | 20.73 | 12.69 | 14.25 | 0.64 | 145% |
| 68 | 17.37 | 15.67 | 25.45 | 1.51 | 151% |
| 77 | 9.78 | 43.77 | 27.77 | 4.68 | 156% |
| 84 | 3.98 | 69.20 | 20.78 | 5.18 | 144% |
| 94 | 0.00 | 79.86 | 21.54 | 5.55 | 137% |
| CO headspace (no fructose) | | | | | |
| 0 | 0.00 | 6.82 | 3.68 | 0.00 | |
| 84 | 0.00 | 7.22 | 3.95 | 0.00 | |
| 94 | 0.00 | 8.07 | 4.35 | 0.00 | |
| 120 | 0.00 | 9.43 | 8.58 | 0.00 | |
| 170 | 0.00 | 60.24 | 1.12 | 1.82 | |

As in Example 1, the proportion of 2,3-butanediol is greater in the mixotrophic fermentation compared with that in either heterotrophic fermentation or autotrophic fermentation. The carbon yield at the time of carbohydrate exhausting in case of mixotrophic fermentation is nearly double that in autotrophic fermentation.

Example 4

A strain of *C. ljungdahlii* was constructed with a recombinant pathway expressing a thiolase (also known as acetyl-CoA acetyltransferase) gene, an acetoacetate transferase subunit A (also known as CoA-transferase subunit A, or COAT A) gene, an acetoacetate transferase subunit B (also known as CoA-transferase subunit B, or COAT B) gene, an acetoacetate decarboxylase (ADC) gene, and a secondary alcohol dehydrogenase (SADH) gene. All genes were derived from *C. acetobutylicum* ATCC 824 except for the secondary alcohol dehydrogenase gene, which came from *C. beijerinckii* DSM 6423. Three biological replicates of this strain were grown anaerobically in media containing initially 5 g/l of fructose and were fed additional fructose over time. The headspace consisted of $N_2$, $CO_2$, and $H_2$ (85%, 10%, 5%, respectively) at 1 atm.

These cultures produced three main metabolites: isopropanol, acetone, and acetate. Acetone is an intermediate metabolite of isopropanol, and so the titers and yields of these two metabolites are combined together. Table 3 shows the metabolite production of these cultures.

TABLE 3

| Biological Replicate | Acetone & Isopropanol titer (g/L) | Acetate titer (g/L) | Acetate in metabolite pool (wt %) | Sugar metabolized (g/L) | Acetone & isopropanol mass yield (wt %) | Acetone & isopropanol yield if all acetate were re-assimilated (wt %) |
| --- | --- | --- | --- | --- | --- | --- |
| #1 | 3.90 | 0.75 | 19.3% | 8.89 | 41.5% | 45.4% |
| #2 | 3.76 | 0.85 | 22.5% | 8.64 | 41.1% | 45.6% |
| #3 | 3.77 | 0.96 | 25.6% | 8.78 | 40.6% | 45.6% |

Mass yield is calculated by dividing total concentration of products produced by the total amount of sugar metabolized. As can be seen, a mass yield of ~41% was achieved for acetone and isopropanol.

This mass yield is greater than could theoretically be from fructose alone. Table 4 outlines different theoretical mass yields based on different substrates.

TABLE 4

| Mode of fermentation | Fructose only-no mixotrophy | Limited mixotrophy | H$_2$ supplemented mixotrophy | Full mixotrophy (CO only) | Full mixotrophy (CO$_2$ & H$_2$) |
|---|---|---|---|---|---|
| Acetone mass yield on sugar (wt %) | 30.0% | 47.1% | 62.8% | 90% | 95.5% |

If no gas was metabolized (fructose only—no mixotrophy) the maximum yield for acetone is only 30%, while the recombinant strain producing acetone/isopropanol had a mass yield of 41%. If all the acetate produced by the recombinant strain were reassimilated into acetone and isopropanol, the mass yields increase to 45%, close to the theoretical maximum of limited mixotrophy (47.1%). This limited mixotrophy is defined as sugar and gas consumption, where the only source of gas is the CO$_2$ evolved during metabolism of the sugar, and potentially hydrogen generated from pyruvate ferredoxin oxidoreductase activity. There is no exogenous CO, CO$_2$ or H$_2$ fed to the fermentation. These mass yields can be further increased with other modes of mixotrophy, such as:

H$_2$ Supplemented Mixotrophy—H$_2$ supplemented mixotrophy is defined as sugar and gas consumption, where the only source of CO$_2$ comes from glycolysis, and H$_2$ is minimally provided by pyruvate ferredoxin oxidoreductase activity and largely provided by exogenous H$_2$.

Full Supplemented Mixotrophy—Full supplemented mixotrophy is defined as sugar and gas consumption, where CO$_2$, CO and/or H$_2$ can be provided exogenously in addition to the gas evolved by glycolysis and/or pyruvate ferredoxin oxidoreductase activity.

Example 5

*C. ljungdahlii* DSM 13528 has a native secondary alcohol dehydrogenase gene (accession number CLJU_c248601 with a nucleic acid sequence of:

```
                                           (SEQ ID NO: 1)
ATGAAAGGTTTTGCAATGTTAGGTATTAACAAATTAGGATGGATTGAAAA

GAAAAACCCAGTGCCAGGTCCTTATGATGCGATTGTACATCCTCTAGCTG

TATCCCCATGTACATCAGATATACATACGGTTTTTGAAGGAGCACTTGGT

AATAGGGAAAATATGATTTTAGGCCATGAAGCTGTAGGTGAAATAGCCGA

AGTTGGCAGCGAAGTTAAAGATTTTAAAGTTGGCGATAGAGTTATCGTAC

CATGCACAACACCTGACTGGAGATCTTTAGAAGTCCAAGCTGGTTTTCAG

CAGCATTCAAACGGTATGCTTGCAGGATGGAAGTTTTCCAATTTTAAAGA

TGGTGTATTTGCAGATTACTTTCATGTAAACGATGCAGATATGAATCTTG

CCATACTCCCAGATGAAATACCTTTAGAAAGTGCAGTTATGATGACAGAC

ATGATGACTACTGGTTTTCATGGAGCAGAACTTGCAGACATAAAAATGGG
```

```
-continued
CTCCAGCGTTGTAGTAATTGGTATAGGAGCTGTTGGATTAATGGGAATAG

CCGGTTCCAAACTTCGAGGAGCAGGCAGAATTATCGGTGTTGGAAGCAGA

CCTGTTTGTGTTGAAACAGCTAAATTTTATGGAGCAACTGATATTGTAAA

TTATAAAAATGGTGATATAGTTGAACAAATCATGGACTTAACTCATGGTA

AAGGTGTAGACCGTGTAATCATGGCAGGCGGTGGTGCTGAAACACTAGCA

CAAGCAGTAACTATGGTTAAACCTGGCGGCGTAATTTCTAACATCAACTA

CCATGGAAGCGGTGATACTTTACCAATACCTCGTGTTCAATGGGGCTGCG

GCATGGCTCACAAAACTATAAGAGGAGGATTATGCCCCGGCGGACGTCTT

AGAATGGAAATGCTAAGAGATCTTGTTCTATATAAACGTGTTGATTTGAG

TAAACTTGTTACTCATGTATTTGATGGTGCAGAAAATATTGAAAAGGCCC

TTTTGCTTATGAAAAATAAGCCAAAAGATTTAATTAAATCAGTAGTTACA

TTCTAA.
```

This gene was deleted from the chromosome and replaced with a chloramphenicol acetyltransferase (CAT) gene, which confers resistance to the antibiotic chloramphenicol or thiamphenicol. This new strain is termed Clj ΔSADH.

A plasmid expressing the genes for thiolase (also known as acetyl-CoA acetyltransferase), acetoacetate transferase subunit A (COAT A), acetoacetate transferase subunit B (COAT B), and acetoacetate decarboxylase (ADC) was transformed into this deletion strain. All genes came from *C. acetobutylicum* ATCC 824.

The deletion strain with the plasmid was grown anaerobically in media containing 5 g/l of fructose. The headspace consisted of N$_2$, CO$_2$, and H$_2$ (85%, 10%, 5%, respectively) at 1 atm.

This strain produced primarily acetone and acetate. Table 5 shows the metabolite production of this strain.

TABLE 5

| Acetone titer (g/L) | Acetate titer (g/L) | Acetate in metabolite pool (wt %) | Sugar metabolized (g/L) | Acetone mass yield (wt %) | Acetone yield if all acetate were re-assimilated (wt %) |
|---|---|---|---|---|---|
| 2.65 | 0.77 | 22.0% | 6.79 | 39.1% | 45.6% |

Mass yield is calculated as in Example 4. The mass yield for this strain is 39.1% for acetone, which is greater than can be achieved on sugar alone (Table 4). This demonstrates the ability of this strain to produce enhanced mass yields over sugar alone.

Example 6

A plasmid was constructed to overexpress a glucose-specific EIIABC gene from *Clostridium acetobutylicum*

ATCC 824 (CA_C0570). This plasmid was transformed into *Clostridium ljungdahlii* DSM 13528 to make the strain Clj (pCAC-EIIABC). Biological replicates of this strain were grown in 10 ml of PETC medium with 5 g/l of fructose and thiamphenicol (5 µg/ml). Once the cultures reached an OD600 of 1.0, 1 ml (10% inoculum) was used to inoculate new tubes of 10 ml of PETC medium with 5 g/l of glucose and thiamphenicol (5 µg/ml). The metabolite profile of these glucose-grown cultures is shown in Table 6.

volumes for the autotrophic and mixotrophic fermentations was replenished every 2-3 days.

Metabolite profiles and carbon yields are shown in the Tables below. Carbon yield is calculated in this example by dividing the total amount of carbon in produced bioproducts by the total amount of carbon metabolized from the sugar in the first feedstock. In the case for metabolites derived from acetyl-CoA, the theoretical maximum without $CO_2$ fixation is 67%.

TABLE 6

| Replicate | Day | Glucose | Fructose | Acetate | Ethanol | Glucose metabolized (g/l) | Rate of consumption (g/hr/g cell mass) |
|---|---|---|---|---|---|---|---|
| #1 | 0 | 5.19 | 0.33 | 0.32 | 0.98 | — | — |
|  | 3 | 4.62 | 0.00 | 1.71 | 0.67 | 0.57 | — |
|  | 4 | 4.16 | 0.00 | 2.12 | 0.67 | 1.03 | — |
|  | 6 | 3.09 | 0.00 | 3.11 | 0.70 | 2.10 | 0.07 |
| #2 | 0 | 5.21 | 0.33 | 0.33 | 0.99 | — | — |
|  | 3 | 4.97 | 0.00 | 1.35 | 0.69 | 0.24 | — |
|  | 4 | 4.73 | 0.00 | 1.60 | 0.70 | 0.47 | — |
|  | 6 | 3.79 | 0.00 | 2.53 | 0.69 | 1.42 | 0.07 |

Replicate #1 metabolized 2.1 g/l of glucose over 6 days, while replicate #2 metabolized 1.42 g/l of glucose over the same period. A plasmid control culture metabolized no glucose over this same time period. The strains also metabolized the residual fructose from the inoculum (0.33 g/l in each case) and some ethanol from the antibiotic (~0.3 g/l). However, the majority of the carbon metabolized was glucose. The maximum rate of consumption of glucose was 0.07 g/hr/g cell mass. This was calculated between Days 4 and 6, after the cultures reached their maximum cell density ($OD_{600} \approx 1.0$). Replicate #1 reached its maximum cell density by Day 3, while Replicate #2 reached this by Day 4. Thus Replicate #1 metabolized a greater amount of glucose than Replicate #2, though they both had the same maximum rate of consumption. In this particular example, the measured rate is about 65% less than the typical batch consumption rate of fructose.

Example 7

Two acetogenic clostridial strains were tested for mixotrophic growth: *Clostridium ljungdahlii* DSM 13528 and *Clostridium autoethanogenum* DSM 10061. Both strains were cultured under three conditions: 10 g/l of fructose (first feedstock) with a $N_2$ headspace at 20 psig (referred to as heterotrophic fermentation), no fructose with a syngas headspace ($CO:CO_2:H_2:N_2$, 55:10:20:15, second feedstock) headspace at 30 psig (autotrophic fermentation), and 10 g/l of fructose with a syngas headspace ($CO:CO_2:H_2:N_2$, 55:10:20:15, second feedstock) headspace at 30 psig (mixotrophic fermentation). In addition, a control culture of *C. acetobutylicum* ATCC 824, that cannot metabolize $CO_2$, was prepared using the heterotrophic conditions to compare against the two acetogens. Three biological replicates of each strain were prepared, grown at 37° C. in standard PETC medium and shaken at 200 rpm. The pH was actively controlled with 6M NaOH to keep the pH between 5 and 6. Headspace

TABLE 7

Heterotrophic fermentation of *C. ljungdahlii*.
Heterotrophic culture (10 g/l fructose with $N_2$ headspace)

| | Concentration (mM) | | | | | |
|---|---|---|---|---|---|---|
| Hour | Fructose | Acetate | Ethanol | 2,3-Butanediol | Lactate | Carbon yield |
| 0 | 55.78 | 0.00 | 0.00 | 0.00 | 0.14 | — |
| 29 | 50.08 | 10.69 | 3.87 | 0.00 | 0.12 | 86% |
| 47 | 40.57 | 34.45 | 5.82 | 0.00 | 0.07 | 88% |
| 70 | 27.47 | 68.20 | 4.78 | 0.00 | 0.12 | 86% |
| 97 | 13.98 | 98.18 | 5.09 | 0.10 | 0.16 | 83% |
| 121 | 4.80 | 120.33 | 6.21 | 0.17 | 0.23 | 83% |
| 144 | 0.25 | 129.28 | 7.51 | 0.19 | 0.33 | 83% |

TABLE 8

Mixotrophic fermentation of *C. ljungdahlii*.
Mixotrophic culture (10 g/l fructose with syngas headspace)

| | Concentration (mM) | | | | | |
|---|---|---|---|---|---|---|
| Hour | Fructose | Acetate | Ethanol | 2,3-Butanediol | Lactate | Carbon yield |
| 0 | 57.41 | 0.00 | 0.00 | 0.00 | 0.16 | — |
| 19 | 57.19 | 1.01 | 0.14 | 0.00 | 0.21 | 220% |
| 42 | 49.60 | 20.52 | 1.87 | 0.03 | 0.20 | 97% |
| 67 | 37.20 | 86.87 | 4.93 | 0.92 | 0.14 | 155% |
| 93 | 34.56 | 112.37 | 5.56 | 3.55 | 0.72 | 184% |
| 114 | 33.32 | 120.78 | 7.15 | 5.48 | 1.57 | 195% |
| 138 | 31.38 | 127.57 | 7.90 | 6.64 | 1.89 | 194% |
| 162 | 29.34 | 134.32 | 8.78 | 7.39 | 2.29 | 192% |

TABLE 9

Autotrophic fermentation of *C. ljungdahlii*.
Autotrophic culture (syngas headspace)

| | Concentration (mM) | | | | | |
|---|---|---|---|---|---|---|
| Hour | Fructose | Acetate | Ethanol | 2,3-Butanediol | Lactate | Carbon yield* |
| 0 | 0.00 | 0.00 | 0.00 | 0.00 | 0.16 | — |
| 25 | 0.00 | 0.43 | 0.00 | 0.00 | 0.16 | — |
| 41 | 0.00 | 1.18 | 0.10 | 0.00 | 0.17 | — |
| 65 | 0.00 | 8.15 | 0.98 | 0.18 | 0.32 | — |
| 90 | 0.00 | 38.05 | 4.17 | 1.86 | 0.51 | — |
| 113 | 0.00 | 39.85 | 3.43 | 1.85 | 0.36 | — |
| 138 | 0.00 | 39.25 | 7.27 | 1.98 | 0.29 | — |
| 164 | 0.00 | 31.32 | 23.67 | 3.18 | 0.35 | — |
| 185 | 0.00 | 58.88 | 20.79 | 3.93 | 0.17 | — |
| 209 | 0.00 | 68.27 | 18.09 | 4.03 | 0.11 | — |
| 233 | 0.00 | 57.82 | 33.30 | 4.90 | 0.36 | — |

*Carbon yield cannot be determined for autotrophic fermentations because there is no sugar substrate.

TABLE 10

Heterotrophic fermentation of *C. autoethanogenum*.
Heterotrophic culture (10 g/l fructose with N₂ headspace)

| | Concentration (mM) | | | | | |
|---|---|---|---|---|---|---|
| Hour | Fructose | Acetate | Ethanol | 2,3-Butanediol | Lactate | Carbon yield |
| 0 | 54.93 | 0.00 | 0.00 | 0.00 | 0.14 | — |
| 23 | 54.04 | 4.50 | 0.52 | 0.00 | 0.14 | 195% |
| 50 | 44.38 | 15.91 | 8.52 | 0.03 | 0.14 | 78% |
| 74 | 23.82 | 37.47 | 23.84 | 1.10 | 0.42 | 69% |
| 97 | 0.50 | 71.35 | 34.07 | 2.57 | 1.18 | 69% |
| 123 | 0.12 | 77.12 | 32.10 | 2.75 | 1.20 | 71% |

TABLE 11

Mixotrophic fermentation of *C. autoethanogenum*.
Mixotrophic culture (10 g/l fructose with syngas headspace)

| | Concentration (mM) | | | | | |
|---|---|---|---|---|---|---|
| Hour | Fructose | Acetate | Ethanol | 2,3-Butanediol | Lactate | Carbon yield |
| 0 | 58.11 | 0.00 | 0.00 | 0.00 | 0.16 | — |
| 19 | 58.27 | 0.20 | 0.00 | 0.00 | 0.16 | — |
| 42 | 52.92 | 8.23 | 3.60 | 0.00 | 0.21 | 78% |
| 67 | 35.95 | 69.41 | 17.77 | 0.63 | 0.25 | 134% |
| 93 | 26.40 | 92.50 | 31.13 | 3.10 | 0.76 | 138% |
| 114 | 14.39 | 121.79 | 44.71 | 8.18 | 2.44 | 142% |
| 138 | 6.71 | 164.11 | 50.85 | 13.05 | 3.86 | 160% |
| 162 | 1.16 | 168.14 | 67.42 | 17.04 | 4.98 | 162% |

TABLE 12

Autotrophic fermentation of *C. autoethanogenum*.
Autotrophic culture (syngas headspace)

| | Concentration (mM) | | | | | |
|---|---|---|---|---|---|---|
| Hour | Fructose | Acetate | Ethanol | 2,3-Butanediol | Lactate | Carbon yield* |
| 0 | 0.00 | 0.00 | 0.00 | 0.00 | 0.16 | — |
| 25 | 0.00 | 1.84 | 0.00 | 0.00 | 0.13 | — |
| 41 | 0.00 | 8.24 | 1.48 | 0.00 | 0.13 | — |
| 65 | 0.00 | 41.96 | 6.72 | 0.21 | 0.04 | — |
| 90 | 0.00 | 38.55 | 10.56 | 0.30 | 0.13 | — |
| 113 | 0.00 | 39.52 | 12.44 | 0.31 | 0.13 | — |
| 138 | 0.00 | 37.94 | 19.51 | 0.69 | 0.20 | — |
| 164 | 0.00 | 25.02 | 39.80 | 3.27 | 0.55 | — |
| 185 | 0.00 | 69.78 | 26.19 | 5.00 | 0.13 | — |
| 209 | 0.00 | 72.45 | 25.86 | 5.12 | 0.12 | — |
| 233 | 0.00 | 67.61 | 32.90 | 5.29 | 0.19 | — |

*Carbon yield cannot be determined for autotrophic fermentations because there is no sugar substrate.

TABLE 13

Heterotrophic fermentation of *C. acetobutylicum*.
Heterotrophic culture (10 g/l fructose with N₂ headspace)

| | Concentration (mM) | | | | | | |
|---|---|---|---|---|---|---|---|
| Hour | Glucose/Fructose | Acetate | Butyrate | Ethanol | Butanol | Lactate | Acetoin | Carbon yield |
| 0 | 90.97 | 3.31 | 0.65 | 0.00 | 0.00 | 0.4 | 0.00 | — |
| 12 | 67.88 | 10.99 | 13.06 | 2.21 | 0.36 | 4.20 | 2.19 | 66% |
| 24 | 47.06 | 16.84 | 24.02 | 2.55 | 1.73 | 10.10 | 1.95 | 64% |
| 48 | 47.13 | 17.00 | 23.74 | 2.34 | 2.09 | 10.09 | 2.46 | 65% |

The results for the two acetogens exemplify the non-additive, i.e., synergistic nature of the mixotrophic fermentation. Combining the heterotrophic fermentation broth with the autotrophic fermentation broth, the mixotrophic fermentation broth is not achieved. For example, adding the endpoints of heterotrophic and autotrophic for *C. ljungdahlii*, the molar ratios of acetate, ethanol, 2,3-butanediol, and lactate are: 0.80, 0.18, 0.02, and 0.003, respectively. In comparison, the ratios for mixotrophic fermentation are 0.88, 0.06, 0.05, and 0.01, respectively. The fraction of both 2,3-butanediol and lactate increase, while the fraction of ethanol decreases. The same is true for *C. autoethanogenum*.

Additionally, the carbon efficiencies under mixotrophic fermentation demonstrate that both sugar and gases are being metabolized, since the efficiencies are >100%. Even under heterotrophic conditions for the two acetogens, the carbon efficiencies are greater than the theoretically possible 67%, demonstrating that some of the evolved $CO_2$ from glycolysis is being metabolized into bioproducts. In comparison, the carbon efficiencies for *C. acetobutylicum* are only ~65%, which is the maximum without being able to metabolize $CO_2$.

Example 8

To further demonstrate concurrent gas and sugar utilization, the acetogens *Clostridium ljungdahlii* DSM 13528 and *Clostridium autoethanogenum* DSM 10061 were again cultured under mixotrophic conditions: 10 g/l of fructose (first feedstock) with a headspace of the gas mixture of CO, $CO_2$, $H_2$, and $N_2$ (55%, 10%, 20%, 15%, respectively) (second feedstock) at 30 psig. In this case though, both CO and $CO_2$ were labeled with $^{13}C$, allowing the quantification of the amount of gas metabolized versus the amount of sugar, labeled with $^{12}C$, is metabolized. As a control, an autotrophic culture was also prepared with the $^{13}C$-labeled syngas at 30 psig. Two biological replicates for each strain were prepared, grown at 37° C. and shaken at 200 rpm.

Figure 2:
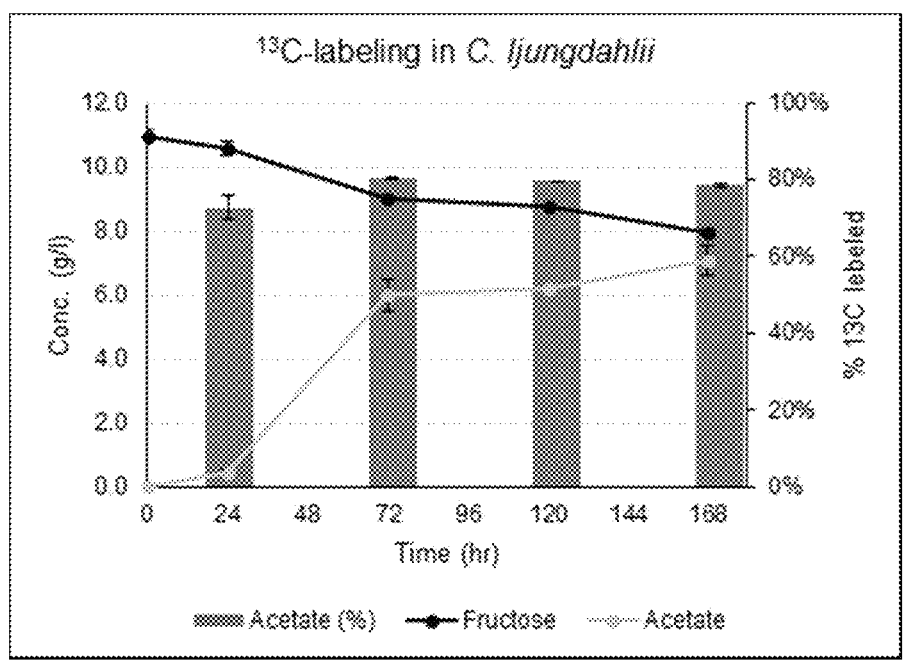
FIG. 2 shows the percentage of $^{13}C$ labeling of acetate in *C. ljungdahlii* over time.
Figure 3:
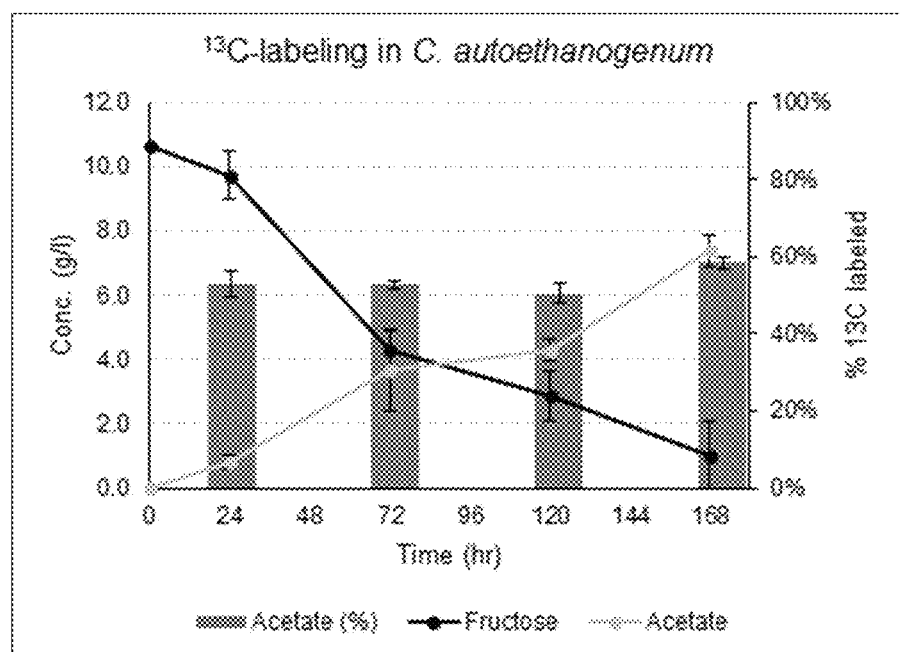
FIG. 3 shows the percentage of $^{13}C$ labeling of acetate in *C. autoethanogenum* over time.

FIG. 2 and FIG. 3 show the percentage of $^{13}C$ labeling of the metabolite acetate over time under mixotrophic conditions in *C. ljungdahlii* and *C. autoethanogenum*, respectively.

For *C. ljungdahlii*, between 73% to 80% of acetate, the primary metabolite, exhibited $^{13}C$-labeling over the course of the fermentation. Even at the earliest time point (t=24 hr), when there is still 10.5 g/l fructose present in the media, over 70% of acetate was derived from the labeled syngas rather than fructose. The majority of growth occurred during the first 72 hours. After which, the low pH of the culture begins to inhibit growth. *C. autoethanogenum* displayed a similar $^{13}C$-incorporation profile, with over 50% of acetate being labeled with $^{13}C$ even at 24 hr. In addition to acetate, *C. autoethanogenum* also produces ethanol, so that the pH does not drop as quickly, which allowed the culture consume the majority of fructose. The method for quantification of $^{13}C$-labeling prevents quantification of $^{13}C$-labeled ethanol.

Example 9

Figure 4:
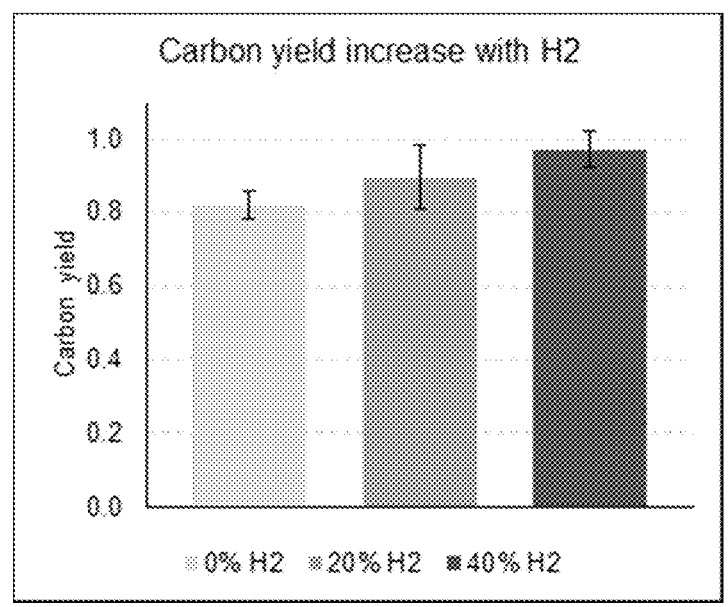
FIG. 4 shows carbon yield with increasing amounts of $H_2$ in the headspace in a *C. ljungdahlii* strain with a deleted secondary alcohol dehydrogenase gene (Clj ΔSADH) and transformed with a plasmid expressing the genes for thiolase, acetoacetate transferase subunit A (COAT A), acetoacetate transferase subunit B (COAT B), and acetoacetate decarboxylase (acetone strain).

The acetone strain created in Example 5 was grown on standard PETC medium with 5 g/l of fructose and with different amounts of $H_2$ in the headspace: 0%, 20% or 40% (in triplicate). As seen in FIG. 4, increasing the amount of $H_2$ in the headspace led to an increase in total carbon metabolized and converted into bioproducts. Carbon yield is the amount of carbon in the produced bioproducts divided by the amount of carbon metabolized.

The product distributions of these cultures shows that almost all $CO_2$ is metabolized into bioproducts.

Figure 5:
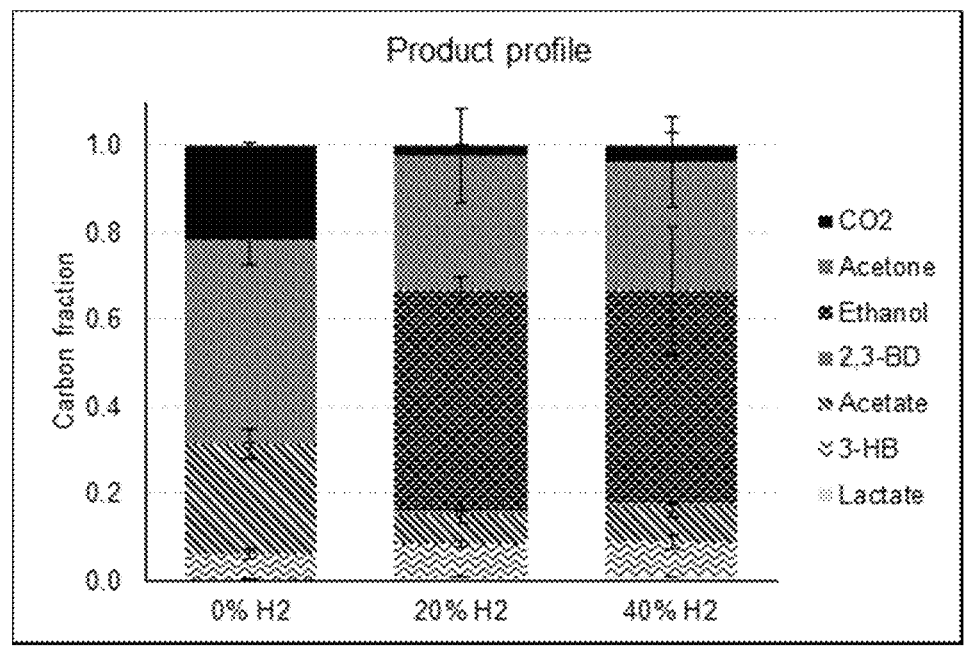
FIG. 5 shows product distributions of the acetone strain grown with increasing amounts of $H_2$ in the headspace. Carbon fraction is the amount of carbon in each bioproduct with the total being 1.0.

FIG. 5 shows distributions of the bioproducts produced by the acetone strain grown with increasing amounts of $H_2$ in the headspace. Carbon fraction is the amount of carbon in each bioproduct with the total being 1.0.

In addition to metabolizing almost all the $CO_2$, the increased reductant in the headspace led to an increased production of reduced products, particularly ethanol.

Example 10

A plasmid was constructed to overexpress a glucose-specific EIIABC gene from *C. acetobutylicum* ATCC 824 ($CA\_C_{0570}$). This plasmid was transformed into *C. ljungdahlii* DSM 13528 to make the strain Clj (pCAC-EIIABC). Four biological replicates of this strain were grown in 10 ml of PETC medium with 5 g/l of fructose and thiamphenicol (5 μg/ml). Once the cultures reached an $OD_{600}$ of 1.0, the cells were harvested, resuspended in 10 ml of PETC medium without any carbon source, and 1 ml (10% inoculum) was transferred to new tubes of 10 ml of PETC medium with 10 g/l of glucose and thiamphenicol (5 μg/m1). The average metabolite profile of these glucose-grown cultures is shown in Table 16.

TABLE 16

| | Concentration (g/l) | | | | Glucose metabolized (g/l) | Rate of consumption (g/hr/g cell mass) |
| --- | --- | --- | --- | --- | --- | --- |
| Day | Glucose | Fructose | Acetate | Ethanol | | |
| 0 | 9.19 | 0.00 | 0.05 | 0.70 | — | — |
| 3 | 7.59 | 0.00 | 2.95 | 0.17 | 1.60 | 0.07 |
| 7 | 6.05 | 0.00 | 4.42 | 0.19 | 3.15 | 0.05 |
| 11 | 5.41 | 0.00 | 5.28 | 0.19 | 3.78 | 0.02 |

After 11 days, the average amount of glucose consumed was 3.78 g/l. A plasmid control culture metabolized no glucose over this same time period. The strains also metabolized some ethanol from the antibiotic (~0.5 g/l), the majority of the carbon metabolized was glucose. The maximum rate of metabolism of glucose was 0.07 g/hr/g cell mass. This was calculated between Days 0 and 3, after the cultures reached their maximum cell density ($OD_{600}$≈1.0).

Example 11

A plasmid was constructed to overexpress a glucose-specific EIIABC gene from *C. saccharobutylicum* DSM 13864 (CLSA_c10070). This plasmid was transformed into *C. ljungdahlii* DSM 13528 to make the strain Clj (pCSB-EIIABC). Four biological replicates of this strain were grown in 10 ml of PETC medium with 5 g/l of fructose and thiamphenicol (5 μg/ml). Once the cultures reached an $OD_{600}$ of 1.0, the cells were harvested, resuspended in 10 ml of PETC medium without any carbon source, and 1 ml (10% inoculum) was transferred to new tubes of 10 ml of PETC medium with 10 g/l of glucose and thiamphenicol (5 μg/ml). The average metabolite profile of these glucose-grown cultures is shown in Table 17.

TABLE 17

| Day | Concentration (g/l) | | | | Glucose-metabolized (g/l) | Rate of consumption (g/hr/g cell mass) |
|---|---|---|---|---|---|---|
| | Glucose | Fructose | Acetate | Ethanol | | |
| 0 | 9.15 | 0.00 | 0.04 | 0.68 | — | — |
| 3 | 8.69 | 0.00 | 1.79 | 0.11 | 0.47 | 0.02 |
| 7 | 6.82 | 0.00 | 3.82 | 0.15 | 2.33 | 0.06 |
| 11 | 5.68 | 0.00 | 5.16 | 0.14 | 3.47 | 0.04 |

After 11 days, the average amount of glucose metabolized was 3.47 g/l. A plasmid control culture metabolized no glucose over this same time period. The strains also metabolized some ethanol from the antibiotic (~0.5 g/l), but as in Example 11, the majority of the carbon metabolized was glucose. The maximum rate of metabolism of glucose was 0.06 g/hr/g cell mass. This was calculated between Days 3 and 7, after the cultures reached their maximum cell density ($OD_{600} \approx 1.0$).

Example 12

Crotyl Alcohol Production in C. ljundgahlii

Wild-type C. ljungdahlii does not produce crotyl alcohol. Wild-type C. ljungdahlii was therefore engineered to produce crotyl alcohol. A plasmid, called pTHCA, over expressing the genes thl (CA_C2783), hbd (CA_C2708), crt (CA_C2712), and adhEl (CA_P0162) was transformed into strain C. ljungdahlii DSM 13528.

C. ljungdahlii DSM 13528 [WT] and C. ljungdahlii (pTHCA) [Clj (pTHCA)] were then grown in standard PETC medium with 5 g/l of fructose anaerobically at 37° C. for 6 days. Metabolite concentrations are presented in Table 18.

TABLE 18

End point metabolite concentrations of crotyl alcohol producing strains of C. ljungdahlii.

| Strain | Concentration of crotyl alcohol (mg/l) |
|---|---|
| WT | 0.0 |
| Clj (pTHCA) | 40.6 |

As can be seen from Table 18, C. ljungdahlii was genetically engineered to overexpress thl, hbd, crt, and adhEl, and thereby exhibited the ability to produce at least 40.6 mg/l of crotyl alcohol under the appropriate fermentation conditions.

The invention claimed is:

1. A mixotrophic fermentation method comprising
   (i) providing
      (a) an isolated naturally acetogenic organism selected from wild type *Clostridium ljungdahlii, Clostridium autoethanogenum,* and *Clostridium ragsdalei,* the native form of the organism having a glucose metabolism rate of less than 0.01 g/hr/g cell mass,
      (b) an acetogenic organism selected from *Clostridium ljungdahlii, Clostridium autoethanogenum,* and *Clostridium ragsdalei* which has been genetically modified to express a thiolase, CoA-transferase subunit A, CoA-transferase subunit B, acetoacetate decarboxylase, and secondary alcohol dehydrogenase, or
      (c) an acetogenic organism selected from *Clostridium ljungdahlii, Clostridium autoethanogenum,* and *Clostridium ragsdalei* which has been genetically modified to reduce expression of a secondary alcohol dehydrogenase or to delete from the genome a secondary alcohol dehydrogenase, and which has been genetically modified to express a thiolase, CoA-transferase subunit A, CoA-transferase subunit B, and acetoacetate decarboxylase;
   (ii) providing a first feedstock and a second feedstock wherein said first feedstock comprises a sugar that is metabolized by the native form of the organism at a rate of less than 0.01 g/hr/g cell mass; and wherein said second feedstock comprises CO, $CO_2$, carbonate, bicarbonate, $H_2$, glycerol, methanol, formate, urea, or a combination thereof; and
   culturing said organism in a fermentation medium, whereby both feedstocks are metabolized and a fermentation broth is formed, which broth comprises at least one bioproduct selected from acetone, isopropanol, acetate, or a combination thereof;
      wherein the method yields a greater amount of the at least one bioproduct than the combined amounts of the at least one bioproduct produced by heterotrophic and autotrophic fermentation with the same organism under the same conditions; and
      wherein the carbon yield, based on the total amount of carbon in produced bioproducts divided by the total amount of carbon metabolized from said first feedstock, is at least 50%.

2. A method according to claim 1, wherein the $^{13}C/^{12}C$ isotope ratio of the carbon present in the bioproduct is less than that of atmospheric $CO_2$.

3. A method according to claim 1, wherein said first feedstock and said second feedstock are present in the fermentation medium at the same time.

4. A method according to claim 1, wherein said fermentation medium comprises at least one of CO, $CO_2$, and hydrogen.

5. A method according to claim 1, wherein said fermentation medium comprises a steel mill produced CO composition.

6. A method according to claim 1, wherein the culturing is performed in whole or in part at a super-atmospheric pressure.

7. A method according to claim 1, wherein said at least one bioproduct is selected from acetone, isopropanol, or a combination thereof.

8. A method according to claim 1, wherein said at least one bioproduct is non-naturally occurring.

9. A method according to claim 1, wherein said second feedstock comprises CO, $CO_2$, carbonate, bicarbonate, methanol, or a combination thereof, and wherein the $^{13}C/^{12}C$ isotope ratio of the carbon present in said second feedstock is less than that of atmospheric $CO_2$.

10. A method according to claim 1, comprising providing said fermentation medium with a mixture of $CO_2$ and hydrogen at a molar ratio in the range from 1:0.1 to 1:5.

11. A method according to claim 10, further comprising steam reforming of a hydrocarbon to form said mixture of $CO_2$ and hydrogen.

12. A method according to claim 1, wherein the first feedstock comprises a sugar selected from glucose and sucrose, and the organism metabolizes $CO_2$ produced on metabolizing the sugar.

13. A method according to claim 1, wherein the first feedstock comprises a sugar selected from glucose and sucrose, the second feedstock comprises at least one of $H_2$ and methanol, and the organism metabolizes $CO_2$ produced on metabolizing the sugar.

14. A method according to claim 1, wherein said at least one bioproduct is acetone.

15. A method according to claim 14, wherein the first feedstock comprises a sugar selected from glucose and sucrose, and the organism metabolizes $CO_2$ produced on metabolizing the sugar.

16. A method according to claim 1, wherein said at least one bioproduct is acetate.

17. A method according to claim 1, wherein said at least one bioproduct is isopropanol.

18. A method according to claim 17, wherein the first feedstock comprises a sugar selected from glucose and sucrose, and the organism metabolizes $CO_2$ produced on metabolizing the sugar.

19. A method according to claim 1, wherein the metabolizing of the first feedstock does not inhibit the metabolizing of the second feedstock.

20. A method according to claim 1, wherein the first feedstock comprises a non-preferred sugar and wherein said second feedstock comprises CO, $CO_2$, carbonate, bicarbonate, $H_2$, glycerol, methanol, formate, urea, or a combination thereof.

21. A mixotrophic fermentation method comprising
   (i) providing an isolated naturally acetogenic organism of the species *Clostridium ljungdahlii,* wherein the organism has been genetically modified to express a thiolase, CoA-transferase subunit A, CoA-transferase subunit B, acetoacetate decarboxylase, and secondary alcohol dehydrogenase,
(ii) providing a fermentation medium comprising a first feedstock and a second feedstock wherein said first feedstock comprises a sugar and said second feedstock comprises CO, $CO_2$, $H_2$, or a combination thereof; and
(iii) culturing said organism in said fermentation medium, whereby both feedstocks are metabolized and a fermentation broth is formed, which fermentation broth comprises at least one bioproduct selected from isopropanol, acetone, and acetate;
wherein the method yields a greater amount of the at least one bioproduct than the combined amounts of the at least one bioproduct produced by heterotrophic and autotrophic fermentation with the same organism under the same conditions; and
wherein the carbon yield, based on the total amount of carbon in produced bioproducts divided by the total amount of carbon metabolized from said first feedstock, is at least 50%.

22. A mixotrophic fermentation method comprising
(i) providing an isolated naturally acetogenic organism of the species *Clostridium ljungdahlii,* wherein the organism has been genetically modified to reduce expression of a secondary alcohol dehydrogenase or to delete from the genome a secondary alcohol dehydrogenase, and genetically modified to express a thiolase, CoA-transferase subunit A, CoA-transferase subunit B, and acetoacetate decarboxylase;
(ii) providing a fermentation medium comprising a first feedstock and a second feedstock wherein said first feedstock comprises a sugar that is metabolized by the native form of the organism at a rate of less than 0.01 g/hr/g cell mass; and
wherein said second feedstock comprises CO, $CO_2$, $H_2$, or mixtures thereof; and
(iii) culturing said organism in said fermentation medium, whereby both feedstocks are metabolized and a fermentation broth is formed, which broth comprises at least one bioproduct comprising acetone;
wherein the method yields a greater amount of the at least one bioproduct than the combined amounts of the at least one bioproduct produced by heterotrophic and autotrophic fermentation with the same organism under the same conditions; and
wherein the carbon yield, based on the total amount of carbon in produced bioproducts divided by the total amount of carbon metabolized from said first feedstock, is at least 50%.

23. A mixotrophic fermentation method comprising
(i) providing
(a) an isolated naturally acetogenic organism selected from *Clostridium ljungdahlii* and *Clostridium autoethanogenum,* the native form of the organism having a glucose metabolism rate of less than 0.01 g/hr/g, cell mass, or
(b) an acetogenic organism selected from *Clostridium ljungdahlii, Clostridium autoethanogenum,* and *Clostridium ragsdalei* which has been genetically modified to express at least one component of a phosphotransferase system;
(ii) providing a first feedstock and a second feedstock wherein said first feedstock comprises a sugar; and wherein said second feedstock comprises CO, $CO_2$, $H_2$, or a combination thereof; and
(iii) culturing said organism in a fermentation medium, whereby both feedstocks are metabolized and a fermentation broth is formed, which broth comprises at least one bioproduct selected from acetate, ethanol, 2,3-butanediol, lactate, or a combination thereof;
wherein the method yields a greater amount of the at least one bioproduct than the combined amounts of the at least one bioproduct produced by heterotrophic and autotrophic fermentation with the same organism under the same conditions; and
wherein the carbon yield, based on the total amount of carbon in produced bioproducts divided by the total amount of carbon metabolized from said first feedstock, is at least 50%.

24. A mixotrophic fermentation method comprising
(i) providing an isolated naturally acetogenic organism of the species *Clostridium ljungdahlii,* wherein the organism has been genetically modified to express a thiolase, 3-hydroxybutyryl-CoA dehydrogenase, 3-hydroxybutyryl-CoA dehydratase, and acetaldehyde/alcohol dehydrogenase;
(ii) providing a fermentation medium comprising a first feedstock and a second feedstock wherein said first feedstock comprises a sugar that is metabolized by the native form of the organism at a rate of less than 0.01 g/hr/g cell mass; and
wherein said second feedstock comprises CO, $CO_2$, $H_2$, or mixtures thereof; and
(iii) culturing said organism in said fermentation medium, whereby both feedstocks are metabolized and a fermentation broth is formed, which broth comprises at least one bioproduct comprising crotyl alcohol;
wherein the method yields a greater amount of the at least one bioproduct than the combined amounts of the at least one bioproduct produced by heterotrophic and autotrophic fermentation with the same organism under the same conditions; and
wherein the carbon yield, based on the total amount of carbon in produced bioproducts divided b the total amount of carbon metabolized from said first feedstock, is at least 50%.

* * * * *

UNITED STATES PATENT AND TRADEMARK OFFICE
CERTIFICATE OF CORRECTION

PATENT NO. : 9,938,542 B2
APPLICATION NO. : 15/055045
DATED : April 10, 2018
INVENTOR(S) : Bryan P. Tracy et al.

Page 1 of 1

It is certified that error appears in the above-identified patent and that said Letters Patent is hereby corrected as shown below:

In the Claims

Column 134, Line 52 (Claim 24, Line 25), please change "divided b the total" to --divided by the total--.

Signed and Sealed this
Eighth Day of January, 2019

Andrei Iancu
*Director of the United States Patent and Trademark Office*